US007226930B2

(12) United States Patent
Hopper et al.

(10) Patent No.: US 7,226,930 B2
(45) Date of Patent: Jun. 5, 2007

(54) PHOSPHODIESTERASE 4 INHIBITORS

(75) Inventors: Allen Hopper, Glen Rock, NJ (US);
Erik Kuester, Franklin, NJ (US);
Robert Dunn, Towaco, NJ (US);
Richard Conticello, Ossining, NY (US)

(73) Assignee: Memory Pharmaceutical Corporation, Montvale, NJ (US)

( * ) Notice: Subject to any disclaimer, the term of this patent is extended or adjusted under 35 U.S.C. 154(b) by 448 days.

(21) Appl. No.: 10/825,611

(22) Filed: Apr. 16, 2004

(65) Prior Publication Data

US 2004/0229918 A1 Nov. 18, 2004

Related U.S. Application Data

(60) Provisional application No. 60/463,725, filed on Apr. 18, 2003.

(51) Int. Cl.
*A61K 31/437* (2006.01)
*A61K 31/4155* (2006.01)
*C07D 231/54* (2006.01)
*C07D 471/06* (2006.01)

(52) U.S. Cl. .................. 514/303; 514/406; 546/119; 548/361.1

(58) Field of Classification Search ............... 514/303, 514/406; 546/119; 548/361.1
See application file for complete search history.

(56) References Cited

U.S. PATENT DOCUMENTS

| | | | |
|---|---|---|---|
| 4,012,495 A | 3/1977 | Schmiechen et al. |
| 4,193,926 A | 3/1980 | Schmiechen et al. |
| 4,219,551 A | 8/1980 | Seidelmann et al. |
| 5,539,111 A | 7/1996 | Petzoldt et al. |
| 5,814,651 A | 9/1998 | Duplantier et al. |
| 5,846,514 A | 12/1998 | Foster et al. |
| 5,869,516 A | 2/1999 | Arlt et al. |
| 5,935,978 A | 8/1999 | Fenton et al. |
| 6,136,821 A | 10/2000 | Hersperger |
| 6,235,736 B1 | 5/2001 | Ina et al. |
| 6,258,833 B1 | 7/2001 | Martins et al. |
| 6,334,997 B1 | 1/2002 | Foster et al. |
| 6,372,777 B1 | 4/2002 | Martins et al. |
| 6,403,597 B1 | 6/2002 | Wilson et al. |
| 6,423,710 B1 | 7/2002 | Martins et al. |
| 6,495,154 B1 | 12/2002 | Tam et al. |

FOREIGN PATENT DOCUMENTS

| | | |
|---|---|---|
| EP | 1 251 126 | 10/2002 |
| JP | 10-72415 | 3/1998 |
| WO | WO 92/19594 | 11/1992 |
| WO | WO 93/07141 A1 | 4/1993 |
| WO | WO 93/25517 A1 | 12/1993 |
| WO | WO 94/14742 A1 | 7/1994 |
| WO | WO 95/28926 A1 | 11/1995 |
| WO | WO 95/35282 | 12/1995 |
| WO | WO 97/25312 | 7/1997 |
| WO | WO 97/49702 | 12/1997 |
| WO | WO 98/58901 A1 | 12/1998 |
| WO | WO 00/66562 | 11/2000 |
| WO | WO 01/40216 | 6/2001 |
| WO | WO 01/58895 | 8/2001 |
| WO | WO 01/68600 A2 | 9/2001 |
| WO | WO 02/45749 A2 | 6/2002 |
| WO | WO 03/087062 | 10/2003 |
| WO | WO 2004/007463 | 1/2004 |
| WO | WO 2004/094411 | 11/2004 |

OTHER PUBLICATIONS

Database Bellstein, XP002367781, J. Chem. Soc., Perkin Trans. 1, 1477-1500, 1977.
International Search Report Dated Sep. 13, 2004.
Written Opinion of the Int'l. Searching Authority dated Apr. 16, 2004.
Database Caplus 'Online!, Chemical Abstracts Service, Columbus, OH, US; XP002294352, Accession No. 1978:6818.
Database Caplus 'Online!, Chemical Abstracts Service, Columbus, OH, US; XP002294353, Accession No. 125:114541.
Database Beilstein, Beilstein Institute for Organic Chemistry, Frankfurt-Main, DE; XP002294354, Accession No. BRN: 7622210.
Malcolm A. Halcrow, et al., "Metal complexes of sterically hindered pyrazolylpyridines. The single crystal X-ray structure of [Cu(L¹)₂]BF₄(L¹ = 1-{pyrid-2-yl}-3-2',5'-dimethoxyphenyl}pyrazole)", Polyhedron, vol. 16, No. 24, pp. 4257-4264, 1997.
Japanese Patent Abstract No. 2001-039954, dated Feb. 13, 2001.
Nagakura et al., "Effects of a phosphodiesterase IV inhibitor rolipram on microsphere embolism-induced defects in memory function and cerebral cyclic AMP signal transduction system in rats," *British Journal of Pharmacology*, (2002) 135, 1783-1793.
Keller et al., "Synthesis and Structure-Activity Relationship of N-Arylrolipram Derivatives as Inhibitors of PDE4 Isozymes," *Chem. Pharm. Bull.*, 49(8) 1009-1017 (2001).
Martin, "PDE4 inhibitors—A review of the recent patent literature," *Idrugs*, 2001 4 (3):312-338.
Wang et al., "Expression, Purification, and Characterization of Human cAMP-Specific Phosphodiesterase (PDE4) Subtypes A, B, C, and D," *Biochemical and Biophysical Research Communications*, 234, 320-324 (1997).
Meyers et al., "The Synthesis of Aracemic 4-Substituted Pyrrolidinones and 3-Substituted Pyrrolidines. An Asymmetric Synthesis of (−)-Rolipram," *J. Org. Chem.*, 1993, 58, 36-42.
Crossland, J., "Rolipram," *Drugs Of The Future*, vol. 13, No. 1, 1988.
Langlois et al., "Synthesis of the Novel Antidepressant (R)-(−)-Rolipram," *Synthetic Communications*, 27 (18), 3133-3144 (1997).

(Continued)

*Primary Examiner*—Taofiq Solola
(74) *Attorney, Agent, or Firm*—Millen, White, Zelano, Branigan, P.C.

(57) ABSTRACT

Selective PDE4 inhibition is achieved by aryl and heteroaryl pyrazole compounds. The compounds exhibit improved PDE4 inhibition as compared to compounds such as rolipram and show selectivity with regard to inhibition of other classes of PDEs.

37 Claims, No Drawings

OTHER PUBLICATIONS

Robichaud et al., "Emesis induced by inhibitors of type IV cyclic nucleotide phosphodiesterase (PDE IV) in the ferret," *Neuropharmacology*, 38 (1999) 289-297.

Houslay et al., "The Multienzyme PDE4 Cyclic Adenosine Monophosphate-Specific Phosphodiesterase Family: Intracellular Targeting, Regulation, and Selective Inhibition by Compounds Exerting Anti-inflammatory and Antidepressant Actions," *Advance in Pharmacology*, vol. 44, pp. 225-342 (1998).

Zhang et al., "Inhibition Of Cyclic AMP Phosphodiesterase (PDE4) Reverses Memory Deficits Associated with NMDA Receptor Antagonism," *Neuropsychopharmacology*, 2000, 23, 198-204.

Zhang et al., "Effects of rolipram on scopolamine-induced impairment of working and reference memory in the radial-arm maze tests in rats," *Psychopharmacology DOI*, 10.1007/s002130000414 (2000).

Barad et al., "Rolipram, a type IV-specific phosphodiesterase inhibitor, facilitates the establishment of long-lasting long-term potentiation and improves memory," *Proc. Natl. Acad. Sci.*, USA, vol. 95, pp. 15020-15025, Dec. 1998.

Demnitz et al., "Enantiodivergent Synthesis of (R)- and (S)-Rolipram," *Molecules*, 1998, 3, 107-119.

Osby et al., "Rapid and Efficient Reduction of Aliphatic Nitro Compounds to Amines," *Tetrahedron Letters*, vol. 26, No. 52, pp. 6413-6416, 1985.

Küsters et al., "Influence of temperature on the enantioseparation of rolipram and structurally related racemates on Chiracel-OD," *Journal of Chromatography* A, 737, (1996) 333-337.

Christensen et al., "1,4-Cyclohexanecarboxylates: Potent and Selective Inhibitors of Phosophodiesterase 4 for the Treatment of Asthma," *J. Med. Chem*, 1998, 41, 821-835.

Krause et al., "Pharmacokinetics of rolipram in the rhesus and cynomolgus monkeys, the rat and the rabbit. Studies on species differences," *Xenobiotica*, 1988, vol. 18, No. 5, 561-571.

Lourenco et al., "Characterization of R-[$^{11}$C]rolipram for PET imaging phosphodiesterase-4: *in vivo* binding, metabolism, and dosimetry studies in rats," *Nuclear Medicine and Biology*, 28 (2001) 347-358.

Egawa et al., "Rolipram and its optical isomers, phosphodiesterase 4 inhibitors, attenuated the scopolamine-induced impairments of learning and memory in rats," *Jpn J Pharmacol*, Nov. 1997, 75 (3):275-81.

Schmiechen et al., "Close correlation between behavioural response and binding in vivo for inhibitors of the rolipram-sensitive phosphodiesterase," *Psychopharmacology*, (Berl) 1990; 102 (1): 17-20.

Marivet et al., "Inhibition of Cyclic Adenosine-3',5'-monophosphate Phosphodiesterase from Vascular Smooth Muscle by Rolipram Analogues," *J. Med. Chem.*, 1989, 32, 1450-1457.

Morgan et al., "Biochemical Pharmacology (1993)", 45(12), 2373-80, pp. 23-27, CAS Abstract Only.

PHOSPHODIESTERASE 4 INHIBITORS

This application claims the benefit of U.S. Provisional Application Ser. No. 60/463,725, filed Apr. 18, 2003, the entire disclosure of which is hereby incorporated.

This application is related to copending application Ser. No. 10/270,724, filed Oct. 16, 2002 (which claims the benefit of Ser. No. 60/329,314, filed Oct. 16, 2001), the entire disclosures of which are hereby incorporated.

FIELD OF THE INVENTION

The present invention relates generally to the field of phosphodiesterase 4 (PDE4) enzyme inhibition. More specifically, this invention relates to selective PDE4 inhibition by novel compounds, e.g., aryl and heteroaryl substituted pyrazole compounds, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE1 is stimulated by $Ca^{2+}$/calmodulin. PDE2 is cGMP-dependent, and is found in the heart and adrenals. PDE3 is cGMP-inhibited, and inhibition of this enzyme creates positive inotropic activity. PDE4 is cAMP specific, and its inhibition causes airway relaxation, anti-inflammatory and antidepressant activity. PDE5 appears to be important in regulating cGMP content in vascular smooth muscle, and therefore PDE5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [Wang et al., Expression, Purification, and Characterization of Human cAMP-Specific Phosphodiesterase (PDE4) Subtypes A, B, C, and D, *Biochem. Biophys. Res. Comm.*, 234, 320-324 (1997)]. In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful anti-inflammatory agents and therefore may be useful in treating diseases where inflammation is problematic such as asthma or arthritis. Further, rolipram improves the cognitive performance of rats and mice in learning paradigms.

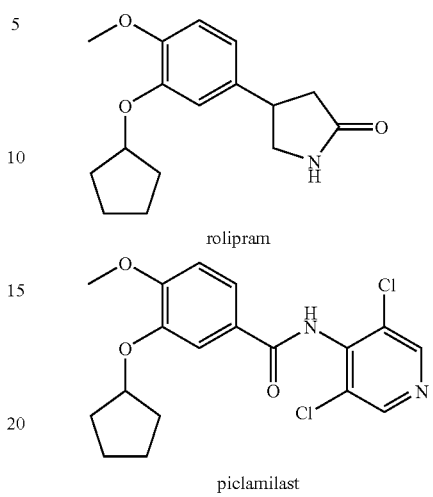

rolipram piclamilast

In addition to such compounds as rolipram, xanthine derivatives such as pentoxifylline, denbufylline, and theophylline inhibit PDE4 and have received attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an antidepressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9): 799-807 for a general review]. Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion, and stomach erosion. In humans, the primary side effect is nausea and emesis. Thus, there is a continuing need to develop selective PDE4 inhibitors with improved side effect profiles (e.g., are relatively non-emetic) while retaining therapeutic utility.

SUMMARY OF THE INVENTION

The present invention relates to novel compounds that inhibit, preferably selectively, PDE4 enzymes, and especially have improved side effect profiles, e.g., are relatively non-emetic (e.g., as compared to the previously discussed prior art compounds). In particular, the present invention relates to aryl and heteroaryl substituted pyrazole compounds. The compounds of this invention at the same time facilitate entry into cells, especially cells of the nervous system.

Still further, the present invention provides methods for synthesizing compounds with such activity and selectivity, as well as methods of and corresponding pharmaceutical compositions for treating a patient, e.g., mammals, including humans, in need of PDE inhibition. Treatment is preferably for a disease state that involves elevated intracellular PDE4 levels or decreased cAMP levels, e.g., involving neurological syndromes, especially those states associated with depression and/or memory impairment, most especially major depression and/or long term memory impairment. In particular, such depression and/or memory impairment is due at least in part to catabolism of intracellular cAMP levels by PDE4 enzymes or where such an impaired condition can be improved by increasing cAMP levels. In a preferred aspect, the compounds of the inventions improve such diseases by inhibiting PDE4 enzymes at doses that do not induce emesis or other side effects.

DETAILED DESCRIPTION OF THE INVENTION

The present invention relates to selective PDE4 inhibition by novel compounds, e.g., aryl and heteroaryl substituted pyrazole compounds, methods of preparing such compounds, compositions containing such compounds, and methods of use thereof.

The present invention includes compounds selected from Formulas I, II, III, IV, V, VI, VII or VIII:

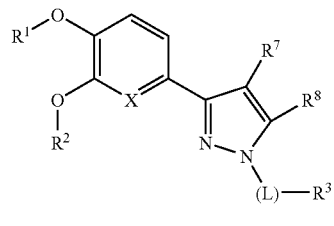

I

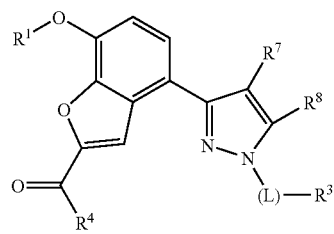

II

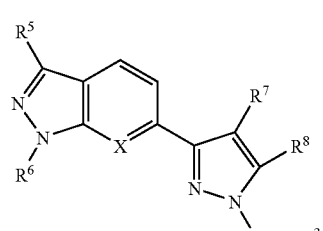

III

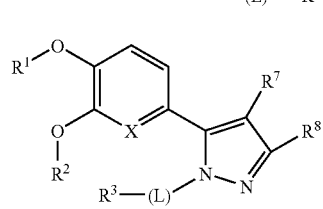

IV

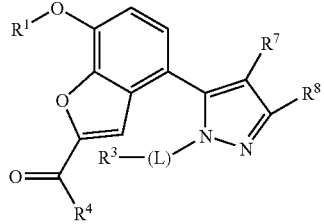

V

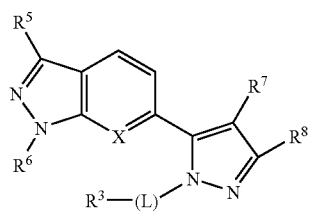

VI

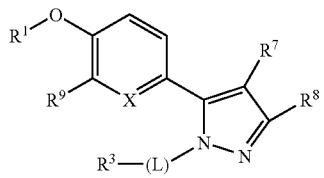

VII

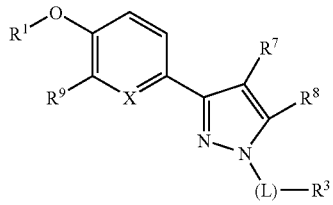

VIII wherein

X is CH or N;

L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen (preferably F), hydroxy, cyano or combinations thereof; $(CH_2)_n$CONH; $(CH_2)_n$CON($C_{1-6}$-alkyl); $(CH_2)_n$NHCO; $(CH_2)_n$CONHSO$_2$; $(CH_2)_n$SO$_2$NH; $(CH_2)_n$SO$_2$; or $(CH_2)_n$CO$_2$ (e.g., a bond, $CH_2$CONH, $SO_2$, $CH_2CO_2$, $CH_2CO$)

n is 0 to 3;

$R^1$ is alkyl having 1 to 4 carbon atoms, which is unsubstituted or substituted one or more times by halogen (e.g., $CH_3$, $CHF_2$);

$R^2$ is H,
  alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups (e.g., $CH_3$, $CHF_2$),
  cycloalkyl having 3 to 8 carbon atoms, which is unsubstituted or substituted one or more times by halogen, oxo, alkyl having 1 to 4 carbon atoms or combinations thereof (e.g., cyclopentyl),
  a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof (e.g., tetrahydrofuranyl), aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof (e.g., benzyl, difluorobenzyl), a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof, arylalkenyl having 8 to 16 carbon atoms, wherein the alkenyl portion has up to 5 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or cycloalkylalkyl having 4 to 16 carbon atoms (e.g., cyclopentylethyl and cyclopropylmethyl), which is unsubstituted or substituted one or more times by halogen, oxo, alkyl or combinations thereof;

$R^3$ is H, alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups (e.g., $C_2H_5$, $CH(CH_3)_2$, n-propyl, n-butyl, t.-butyl), cycloalkyl having 3 to 8 carbon atoms, which is unsubstituted or substituted one or more times by halogen, oxo, alkyl, or combinations thereof (e.g., cyclopentyl, cyclohexyl), aryl having 6 to 14 carbon atoms, which is unsubstituted or substituted one or more times by halogen, alkyl, hydroxy, alkoxy, halogenated alkyl, halogenated alkoxy (e.g., $OCF_3$), nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy (e.g., acetoxy), acylamido (e.g., acetamido), imidazolyl, pyridinyl, morpholinyl, piperadinyl, piperazinyl, tetrazolyl, alkylsulphonimide (e.g., $CH_3SO_2$—NHCO—), arylsulphonimide (e.g., $C_6H_5SO_2$—NHCO—) or combinations thereof (e.g., phenyl, bromophenyl, cyanophenyl, nitrophenyl, fluorophenyl, difluorophenyl, trifluoromethoxyphenyl, methylphenyl, dimethylphenyl, methoxyphenyl), heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, tetrazolyl, alkylsulphonimide, arylsulphonimide, aryl, oxo, acylamido (e.g., acetamido), or combinations thereof (e.g., pyridyl, methylpyridyl, benzothiaolyl), arylalkyl having 7 to 16 carbon atoms, which is unsubstituted or substituted, preferably in the aryl portion, one or more times by halogen, alkyl, hydroxy, alkoxy, halogenated alkyl (e.g. $CF_3$), halogenated alkoxy (e.g. $OCF_3$), nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy (e.g., acetoxy), acylamido (e.g., acetamido), tetrazolyl, alkylsulphonimide, arylsulphonimide, or combinations thereof and/or substituted in the alkyl portion by halogen, oxo, cyano, or combinations thereof (e.g., benzyl, methylbenzyl, t.-butylbenzyl, methoxybenzyl, dimethoxybenzyl, fluorobenzyl, difluorobenzyl, trifluoromethylbenzyl, trifluoromethoxybenzyl, chlorobenzyl, aminobenzyl, nitrobenzyl, methoxycarbonylbenzyl, methylsulfonylbenzyl, phenethyl, phenpropyl), a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof (e.g., pyridylmethyl),
cycloalkylalkyl having 4 to 16 carbon atoms (e.g., cyclopentylethyl and cyclopropylmethyl), which is unsubstituted or substituted one or more times by halogen, oxo, alkyl or combinations thereof, or
alkoxyalkyl having 3 to 8 carbon atoms;

$R^4$ is alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups (e.g., $CH_3$);

$R^5$ is H,
alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups (e.g., $CH_3$, $C_2H_5$);

$R^6$ is H,
alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups,
cycloalkyl having 3 to 8 carbon atoms, which is unsubstituted or substituted one or more times by halogen, oxo, alkyl, or combinations thereof (e.g., cyclopentyl),
cycloalkylalkyl having 4 to 16 carbon atoms (e.g., cyclopentylethyl and cyclopropylmethyl), which is unsubstituted or substituted one or more times by halogen, oxo, alkyl or combinations thereof,
aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl (e.g., $CH_3$, $C_2H_5$, $CF_3$, hydroxymethyl, 2-(2-hydroxy)propyl, hydroxymethyl), carboxy, alkoxycarbonyl having 2 to 6 carbon atoms (e.g., ethoxycarbonyl), —CO-alkyl having 2 to 6 carbon atoms (e.g., $CH_3CO$), or phenyl; and $R^9$ is halogen (e.g., F);

and pharmaceutically acceptable salts thereof.

In accordance with the method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound selected from Formulas I, II, III, V, V, VI, VII or VIII:

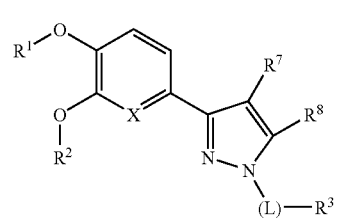

I

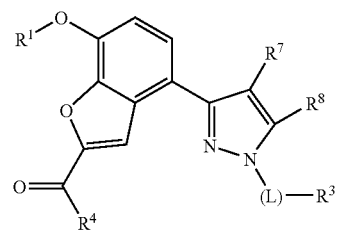

II

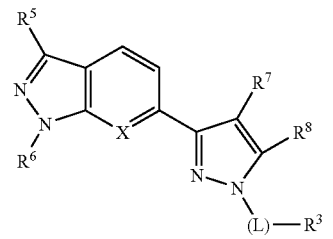

III

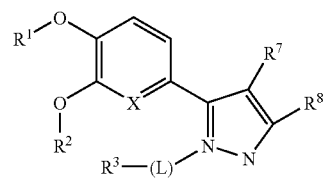

IV

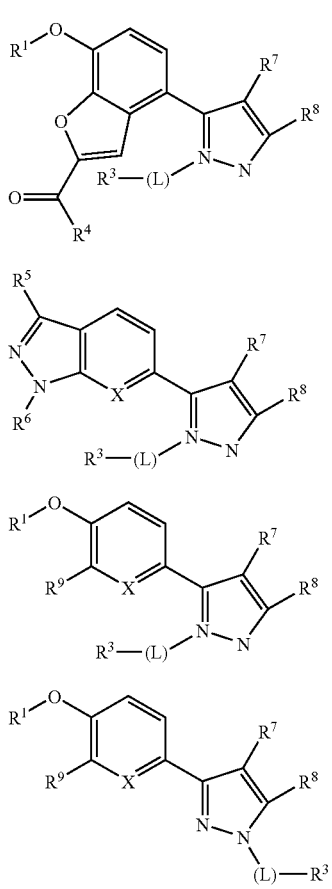

wherein
- X is CH or N;
- L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen (preferably F), hydroxy, cyano or combinations thereof; $(CH_2)_n$CONH; $(CH_2)_n$CON($C_{1-6}$-alkyl); $(CH_2)_n$NHCO; $(CH_2)_n$CONHSO$_2$; $(CH_2)_n$SO$_2$NH; $(CH_2)_n$SO$_2$; or $(CH_2)_n$CO$_2$ (e.g., a bond, $CH_2$CONH, $SO_2$, $CH_2$CO$_2$, $CH_2$CO)
- n is 0 to 3;
- $R^1$ is alkyl having 1 to 4 carbon atoms, which is unsubstituted or substituted one or more times by halogen (e.g., $CH_3$, $CHF_2$);
- $R^2$ is H,
  - alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups (e.g., $CH_3$, $CHF_2$),
  - cycloalkyl having 3 to 8 carbon atoms, which is unsubstituted or substituted one or more times by halogen, oxo, alkyl having 1 to 4 carbon atoms or combinations thereof (e.g., cyclopentyl),
  - a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof (e.g., tetrahydrofuranyl),
  - aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
  - arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof (e.g., benzyl, difluorobenzyl),
  - a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof,
  - arylalkenyl having 8 to 16 carbon atoms, wherein the alkenyl portion has up to 5 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof,
  - a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or
  - cycloalkylalkyl having 4 to 16 carbon atoms (e.g., cyclopentylethyl and cyclopropylmethyl), which is unsubstituted or substituted one or more times by halogen, oxo, alkyl or combinations thereof;
- $R^3$ is H,
  - alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups (e.g., $C_2H_5$, $CH(CH_3)_2$, n-propyl, n-butyl, t.-butyl),
  - cycloalkyl having 3 to 8 carbon atoms, which is unsubstituted or substituted one or more times by halogen, oxo, alkyl, or combinations thereof (e.g., cyclopentyl, cyclohexyl), aryl having 6 to 14 carbon atoms, which is unsubstituted or substituted one or more times by halogen, alkyl, hydroxy, alkoxy, halogenated alkyl, halogenated alkoxy (e.g., OCF$_3$), nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy (e.g., acetoxy), acylamido (e.g., acetamido), imidazolyl, pyridinyl, morpholinyl, piperadinyl, piperazinyl, tetrazolyl, alkylsulphonimide (e.g., CH$_3$SO$_2$—NHCO—), arylsulphonimide (e.g., C$_6$H$_5$SO$_2$—NHCO—) or combinations thereof (e.g., phenyl, bromophenyl, cyanophenyl, nitrophenyl, fluorophenyl, difluorophenyl, trifluoromethoxyphenyl, methylphenyl, dimethylphenyl, methoxyphenyl), heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, tetrazolyl, alkylsulphonimide, arylsulphonimide, aryl, oxo, acylamido (e.g., acetamido), or combinations thereof (e.g., pyridyl, methylpyridyl, benzothiaolyl), arylalkyl having 7 to 16 carbon atoms, which is unsubstituted or substituted, preferably in the aryl portion, one or more times by halogen, alkyl, hydroxy, alkoxy, halogenated alkyl (e.g. CF$_3$), halogenated alkoxy (e.g. OCF$_3$), nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy (e.g., acetoxy), acylamido (e.g., acetamido), tetrazolyl, alkylsulphonimide, arylsulphonimide, or combinations thereof and/or substituted in the alkyl portion by halogen, oxo, cyano, or combinations thereof (e.g., benzyl, methylbenzyl, t.-butylbenzyl, methoxybenzyl, dimethoxybenzyl, fluorobenzyl, difluorobenzyl, trifluoromethylbenzyl, trifluoromethoxybenzyl, chlorobenzyl, aminobenzyl, nitrobenzyl, methoxycarbonylbenzyl, methylsulfonylbenzyl, phenethyl, phenpropyl), a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof (e.g., pyridylmethyl), cycloalkylalkyl having 4 to 16 carbon atoms (e.g., cyclopentylethyl and cyclopropylmethyl), which is unsubstituted or substituted one or more times by halogen, oxo, alkyl or combinations thereof, or alkoxyalkyl having 3 to 8 carbon atoms;

$R^4$ is alkyl having 1 to 6 carbon atoms, which is unsubstituted or substituted one or more times by halogen, oxo, or combinations thereof wherein optionally one or more —CH$_2$CH$_2$— groups are replaced in each case by —CH=CH— or —C≡C— groups (e.g., CH$_3$);

$R^5$ is H,
alkyl having 1 to 6 carbon atoms, which is unsubstituted or substituted one or more times by halogen, oxo, or combinations thereof wherein optionally one or more —CH$_2$CH$_2$— groups are replaced in each case by —CH=CH— or —C≡C— groups (e.g., CH$_3$, C$_2$H$_5$);

$R^6$ is H,
alkyl having 1 to 6 carbon atoms, which is unsubstituted or substituted one or more times by halogen, oxo, or combinations thereof wherein optionally one or more —CH$_2$CH$_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof (e.g., cyclopentyl), cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/ or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl (e.g., $CH_3$, $C_2H_5$, $CF_3$, hydroxymethyl, 2-(2-hydroxy)propyl, hydroxymethyl), carboxy, alkoxycarbonyl having 2 to 6 carbon atoms (e.g., ethoxycarbonyl), —CO-alkyl having 2 to 6 carbon atoms (e.g., $CH_3CO$), or phenyl; and $R^9$ is halogen (e.g., F);

and pharmaceutically acceptable salts thereof.

According to a further compound aspect, the present invention includes compounds selected from Formulas I, II, III, VI, V, or VI:

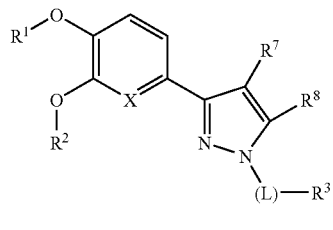

I

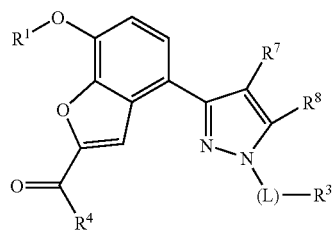

II

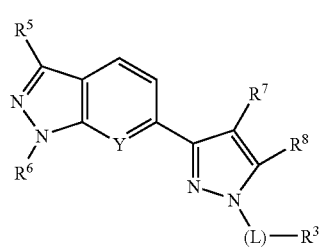

III

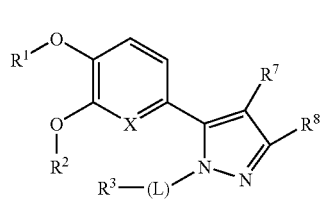

IV

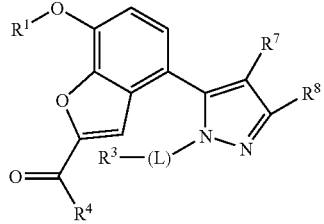

V

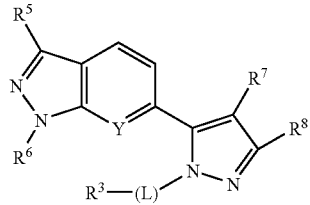

VI wherein

X is CH or N;

Y is CH or N;

L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen (preferably F), hydroxy, cyano or combinations thereof; $(CH_2)_n$CONH; $(CH_2)_n$NHCO; $(CH_2)_n$CONHSO$_2$; $(CH_2)_n$SO$_2$NH; $(CH_2)_n$SO$_2$; or $(CH_2)_n$CO$_2$;

n is 0 to 3;

$R^1$ is alkyl having 1 to 4 carbon atoms, which is unsubstituted or substituted one or more times by halogen;

$R^2$ is H, alkyl having 2 to 8 carbon atoms wherein optionally one or more —$CH_2CH_2$— groups are replaced in each case by —CH=CH— or —C≡C— groups, alkyl having 1 to 8 carbon atoms, which is substituted one or more times by halogen, oxo or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl having 1 to 4 carbon atoms or combinations thereof, a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof, arylalkenyl having 8 to 16 carbon atoms, wherein the alkenyl portion has up to 5 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or cycloalkylalkyl having 4 to 16 carbon atoms (e.g., cyclopentylethyl and cyclopropylmethyl), which is unsubstituted or substituted one or more times by halogen, oxo, alkyl or combinations thereof;

$R^3$ is H, alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, aryl having 6 to 14 carbon atoms, which is unsubstituted or substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy), or combinations thereof, heterocyclic group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof (e.g., pyridyl, methylpyridyl, azaindolyl), arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, or alkoxyalkyl having 3 to 8 carbon atoms;

$R^4$ is alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups;

$R^5$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups;

$R^6$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

and pharmaceutically acceptable salts thereof.

According to a further method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound selected from Formulas I, II, III, IV, V, or VI:

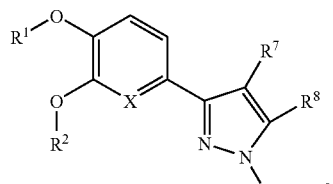

I

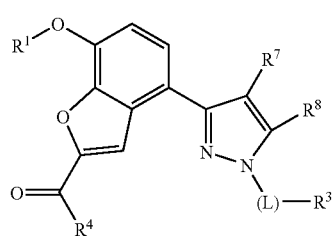

II

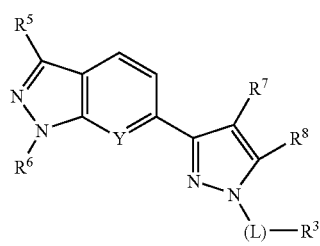

III

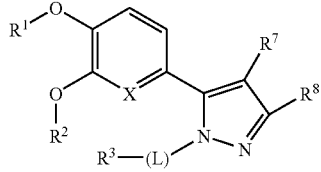

IV

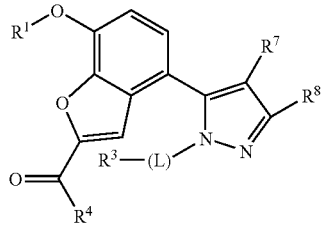

V

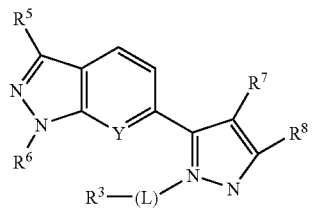

VI wherein
X is CH or N;
Y is CH or N;
L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen (preferably F), hydroxy, cyano or combinations thereof; $(CH_2)_n$CONH; $(CH_2)_n$NHCO; $(CH_2)_n$CONHSO$_2$; $(CH_2)_n$SO$_2$NH; $(CH_2)_n$SO$_2$; or $(CH_2)_n$CO$_2$;
n is 0 to 3;
$R^1$ is alkyl having 1 to 4 carbon atoms, which is unsubstituted or substituted one or more times by halogen;
$R^2$ is H,
  alkyl having 2 to 8 carbon atoms wherein optionally one or more —$CH_2CH_2$— groups are replaced in each case by —CH=CH— or —C≡C— groups,
  alkyl having 1 to 8 carbon atoms, which is substituted one or more times by halogen, oxo or combinations thereof wherein optionally one or more —$CH_2CH_2$— groups are replaced in each case by —CH=CH— or —C≡C— groups,
  cycloalkyl having 3 to 8 carbon atoms, which is unsubstituted or substituted one or more times by halogen, oxo, alkyl having 1 to 4 carbon atoms or combinations thereof,
  a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof,
  aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof, arylalkenyl having 8 to 16 carbon atoms, wherein the alkenyl portion has up to 5 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or cycloalkylalkyl having 4 to 16 carbon atoms (e.g., cyclopentylethyl and cyclopropylmethyl), which is unsubstituted or substituted one or more times by halogen, oxo, alkyl or combinations thereof;

$R^3$ is H,
alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, aryl having 6 to 14 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy), or combinations thereof, heterocyclic group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, or alkoxyalkyl having 3 to 8 carbon atoms;

$R^4$ is alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups;

$R^5$ is H,
alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups;

$R^6$ is H,
alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

and pharmaceutically acceptable salts thereof.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes, but is not limited to, inflammatory diseases. These compounds may also function as antidepressants, or be useful in treating cognitive and negative symptoms of schizophrenia.

Assays for determining PDE4 inhibiting activity, selectivity of PDE4 inhibiting activity, and selectivity of inhibiting PDE4 isoenzymes are known within the art. See, e.g., U.S. Pat. No. 6,136,821, the disclosure of which is incorporated herein by reference.

Halogen herein refers to F, Cl, Br, and I. Preferred halogens are F and Cl.

Alkyl means a straight-chain or branched-chain aliphatic hydrocarbon radical. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

These alkyl radicals can optionally have one or more —$CH_2CH_2$— groups replaced in each case by —CH=CH— or —C≡C— groups. Suitable alkenyl or alkynyl groups are 1-propenyl, 2-propenyl, 1-propynyl, 1-butenyl, 2-butenyl, 3-butenyl, 1-butynyl, 1,3-butadienyl, and 3-methyl-2-butenyl.

In the arylalkyl groups, heterocyclic-alkyl groups, cycloalkyl-alkyl groups and alkoxyalkyl groups, "alkyl" refers to a divalent alkylene group having in general up to about 13 carbon atoms. In the case of the arylalkyl group, the "alkyl" portion has preferably 2 to 10 carbon atoms. In the heterocyclic-alkyl groups, the "alkyl" portion preferably has 1 to 12 carbon atoms. In the alkoxyalkyl groups, the "alkyl" portion preferably has 2 to 7 carbon atoms. In the cycloalkylalkyl groups, the "alkyl" portion preferably has 1 to 13 carbon atoms.

In the cases where alkyl is a substituent (e.g., alkyl substituents on aryl and heterocyclic groups) or is part of a substituent (e.g., in the alkylamino, dialkylamino, hydroxyalkyl, hydroxyalkoxy, alkylthio, alkylsulphinyl, and alkylsulphonyl substituents for aryl), the alkyl portion preferably has 1 to 12 carbon atoms, especially 1 to 8 carbon atoms, in particular 1 to 4 carbon atoms.

Alkoxy means alkyl-O— groups in which the alkyl portion has 1 to 8 carbon atoms, and which can be substituted, for example, by halogens. Suitable alkoxy groups include methoxy, ethoxy, propoxy, isopropoxy, isobutoxy, sec-butoxy, pentoxy, hexoxy, heptoxy, octoxy, and trifluoromethoxy. Preferred alkoxy groups are methoxy and ethoxy.

Similarly, alkoxycarbonyl means an alkyl-O—CO— group in which the alkyl portion has 1 to 8 carbon atoms.

Alkenyl refers to straight-chain or branched-chain aliphatic radicals containing 2 to 12 carbon atoms in which one or more —$CH_2$—$CH_2$— structures is replaced by —CH=CH—. Suitable alkenyl groups are ethenyl, 1-propenyl, 2-methylethenyl, 1-butene, 2-butene, 1-pentenyl, and 2-pentenyl. In the arylalkenyl groups, alkenyl refers to an alkyenylene group having preferably 2 to 5 carbon atoms.

Cycloalkyl means a monocyclic, bicyclic or tricyclic saturated hydrocarbon radical having 3 to 8 carbon atoms, preferably 4 to 6 carbon atoms, more preferably 5 carbon atoms. Suitable cycloalkyl groups include cyclopropyl, cyclobutyl, cyclopentyl, cyclohexyl, cycloheptyl, cyclooctyl, and norbornyl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, and bicyclo[4.2.0]octyl.

The cycloalkyl group can be substituted by halogens, oxo and/or alkyl. Halogens and/or alkyl groups are preferred substituents.

Cycloalkylalkyl refers to a cycloalkyl-alkyl-radical in which the cycloalkyl and alkyl portions are in accordance with the previous descriptions. Suitable examples include cyclopentylethyl and cyclopropylmethyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Arylalkyl refers to an aryl-alkyl-radical in which the aryl and alkyl portions are in accordance with the previous descriptions. Suitable examples include 1-phenethyl, 2-phenethyl, phenpropyl, phenbutyl, phenpentyl, and naphthylenemethyl.

Arylalkenyl refers to an aryl-alkenyl-radical in which the aryl and alkenyl portions are in accordance with the previous descriptions of aryl and alkenyl. Suitable examples include 3-aryl-2-propenyl.

Heterocyclic groups refer to saturated, partially saturated and fully unsaturated heterocyclic groups having one or two rings and a total number of 5 to 10 ring atoms wherein at least one of the ring atoms is an N, O or S atom. Preferably, the heterocyclic group contains 1 to 3, especially 1 or 2, hetero-ring atoms selected from N, O and S. Suitable saturated and partially saturated heterocyclic groups include, but are not limited to tetrahydrofuranyl, tetrahydrothienyl, pyrrolidinyl, isoxazolinyl and the like. Suitable heteroaryl groups include but are not limited to furyl, thienyl, pyrrolyl, pyrazolyl, imidazolyl, pyridyl, pyrimidinyl, indolyl, quinolinyl, naphthyridinyl, azaindolyl (e.g., 7-azaindolyl), 1,2,3,4,-tetrahydroisoquinolyl, and the like. Preferred heterocyclic and heteroaryl groups include terahydrofuranyl, tetrahydropyranyl, 2-thienyl, 3-thienyl, 2-, 3- or 4-pyridyl, 2-, 3-, 4-, 5-, 6-, 7- or 8-quinolinyl, 7-azaindolyl, and 1-, 3-, 4-, 5, -6, -7- or 8-isoquinolinyl.

Substituted heterocyclic groups refer to the heterocyclic groups described above which are substituted in one or more places by halogen, aryl, alkyl, alkoxy, cyano, halogenated alkyl (e.g., trifluoromethyl), nitro, oxo, amino, alkylamino, and dialkylamino.

Heterocyclic-alkyl refers to a heterocyclic-alkyl-group wherein the heterocyclic and alkyl portions are in accordance with the previous discussions. Suitable examples are pyridylmethyl, thienylmethyl, pyrimidinylmethyl, pyrazinylmethyl, isoquinolinylmethyl, pyridylethyl and thienylethyl.

Partially unsaturated carbocyclic structures are non-aromatic monocyclic or bicyclic structures containing 5 to 14 carbon atoms, preferably 6 to 10 carbon atoms, wherein the ring structure(s) contains at least one C=C bond. Suitable examples are cyclopentenyl, cyclohexenyl, tetrahydronaphthenyl and indan-2-yl.

Acyl refers to alkanoyl radicals having 1 to 13 carbon atoms in which the alkyl portion can be substituted by halogen, hydroxy, carboxy, alkyl, aryl and/or alkoxy; or aroyl radicals having 7 to 15 carbon atoms in which the aryl portion can be substituted by halogen, alkyl, alkoxy, nitro, carboxy and/or hydroxy. Suitable acyl groups include formyl, acetyl, propionyl, butanoyl and benzoyl.

Substituted radicals preferably have 1 to 3 substituents, especially 1 or 2 substituents.

$R^1$ is preferably alkyl having 1 to 2 carbon atoms, which is unsubstituted or substituted, and more preferably 1 carbon atom. For $R^1$, the substituted alkyl groups are preferably substituted one or more times by halogen, especially F and Cl. More preferably, $R^1$ is $CH_3$ or $CF_2H$.

$R^2$ is preferably alkyl having 1 to 4 carbon atoms. For $R^2$, the substituted alkyl groups are preferably substituted one or more times by halogen, especially F and Cl. Preferably, $R^2$ is alkyl having 1 to 4 carbons which is unsubstituted or substituted with one or more F atoms.

$R^2$ can also be preferably cycloalkylalkyl group, wherein the "alkyl" portion preferably has 1 to 2 carbon atoms. $R^2$ is also preferably a cycloalkyl, which has 4 to 7 atoms. $R^2$ is also preferably a saturated heterocyclic group with 5 to 7 atoms and containing 1 or 2 hetero-ring atoms selected from O and S. More preferably, $R^2$ is a saturated heterocyclic group with 5 ring atoms containing 1 hetero-ring atom selected from O and S. $R^2$ is also preferably a benzyl group.

In particular, $R^2$ is preferably alkyl, halogenated alkyl, cycloalkyl which is substituted or unsubstituted, cycloalkylalkyl which is substituted or unsubstituted, tetrahydrofuranyl, or arylalkyl which is substituted or unsubstituted. More preferably, $R_2$ is $CH_3$, $C_2H_5$, isopropyl, $CF_2H$, cyclobutyl, cyclopentyl, cyclopropylmethyl, or 3-tetrahydrofuranyl.

$R^3$ can also be preferably an aromatic carbocyclic radical preferably containing 6 to 14 carbon atoms. More preferably, $R^3$ has 6 carbon atoms and is phenyl. $R^3$ is preferably phenyl substituted with one or more halogen (preferably fluorine), cyano, nitro, amino, alkyl (preferably methyl), alkoxy (preferably methoxy) or carboxy (e.g., phenyl, bromophenyl, nitrophenyl, fluorophenyl, methoxyphenyl, carboxyphenyl, trifluoromethoxyphenyl, dimethylphenyl).

More preferably, $R^3$ is 4-carboxyphenyl, 2,3-difluorophenyl, 4-methylphenyl, 4-tert.-butylphenyl, 4-methoxyphenyl, 3,4-difluorophenyl, or 4-fluorophenyl.

$R^3$ can also preferably be a cycloalkyl group, and more preferably cyclohexyl or cyclopentyl. $R^3$ can also preferably be an alkyl group, more preferably ethyl, $CH(CH_3)_2$, n-propyl, n-butyl, or t-butyl.

$R^3$ is also preferably a heterocyclic group, more preferably thiazolyl, pyridyl or benzothiazolyl, which in each case is substituted or unsubstituted.

In accordance with a further preference, $R^3$ is arylalkyl such as benzyl or phenethyl, which in each case is substituted or unsubstituted. In particular, $R^3$ is an arylalkyl selected from benzyl, methylbenzyl, t.-butylbenzyl, methoxybenzyl, dimethoxybenzyl, carboxybenzyl, fluorobenzyl, difluorobenzyl, trifluoromethylbenzyl, trifluoromethoxybenzyl, chlorobenzyl, nitrobenzyl, methoxycarbonylbenzyl, and phenethyl.

$R^4$ is preferably alkyl having 1 to 3 carbon atoms, and more preferably $R^4$ is $CH_3$. $R^4$ is preferably a substituted alkyl group having 1 to 3 carbon atoms and is preferably substituted one or more times by halogen, especially F and Cl.

$R^5$ is preferably alkyl having 1 to 3 carbon atoms. More preferably, $R^5$ is $CH_3$ or $CH_2CH_3$.

$R^6$ preferably is cycloalkyl having 4 to 7 carbon atoms, and more preferably 5 carbon atoms and is cyclopentyl.

$R^7$ and $R^8$ are each preferably H. $R^8$ can also preferably be alkyl, fluorinated alkyl, hydroxylalkyl, carboxy, alkoxycarbonyl having 2 to 6 carbon atoms (e.g., ethoxycarbonyl), —CO-alkyl having 2 to 6 carbon atoms (e.g., $CH_3CO$), or phenyl. For example, $R^8$ can be H, $CH_3$, $C_2H_5$, $CF_3$, hydroxymethyl, 2-(2-hydroxy)propyl), carboxy, ethoxycarbonyl, $CH_3CO$, or phenyl.

X is preferably CH.

L is preferably a bond, $CH_2$, $CH_2CH_2$, $CH_2CO$, $CH_2CO_2$, or $CH_2CONH$.

The subscript n is preferably 0 or 1.

In addition, preferred PDE4 inhibitors in accordance with the invention are compounds described by subformulas Ia-Im, IIa-IIh, IIIa-IIIg, IVa-IVm, Va-Vh, VIa-VIg, and VIIa-VIId, which correspond to Formulas I, II, III, IV, V, VI, or VII but exhibit the following preferred groups:

Ia or IVa
  $R^1$ is $CH_3$ or $CF_2H$.
Ib or IVb
  $R^1$ is $CH_3$ or $CF_2H$; and
  $R^2$ is alkyl, cycloalkyl, cycloalkylalkyl, a heterocyclic group, or arylalkyl, which in each case is substituted or unsubstituted.

Ic or IVc
  R$^1$ is CH$_3$ or CF$_2$H; and
  R$^2$ is CF$_2$H, cyclopropylmethyl, cyclopentyl, 3-tetrahydrofuranyl (preferably 3-(3R)-tetrahydrofuranyl), or benzyl.
Id or IVd
  R$^1$ is CH$_3$ or CF$_2$H; and
  R$^2$ is CF$_2$H, cyclopropylmethyl, cyclopentyl, or 3-tetrahydrofuranyl(preferably 3-(3R)-tetrahydrofuranyl).
Ie or IVe
  R$^1$ is CH$_3$ or CF$_2$H; and
  R$^3$ is aryl, heterocyclic, alkyl, or cycloalkyl.
If or IVf
  R$^1$ is CH$_3$ or CF$_2$H;
  R$^3$ is aryl, heterocyclic, alkyl, or cycloalkyl;
  L is a bond, CH$_2$, CH$_2$CH$_2$, or CH$_2$CO.
Ig or IVg
  R$^1$ is CH$_3$ or CF$_2$H; and
  R$^3$ is H, isopropoxy, 2-(6-methyl-pyridyl), 2-cyanophenyl, 2,3-difluorophenyl, 2-methylphenyl, 4-nitrophenyl, 4-aminophenyl, phenyl, pyridyl (e.g., 4-pyridyl), cyclohexyl, cyclopentyl, ethyl, t-butyl, tetrahydroisoquinolyl, 7-azaindolyl, or 4-methylsulfonylphenyl.
Ih or IVh
  R$^1$ is CH$_3$ or CF$_2$H;
  R$_2$ is H, isopropoxy, CF$_2$H, cyclopropylmethyl, cyclopentyl, 3-tetrahydrofuranyl (preferably 3-(3R)-tetrahydrofuranyl), 2,3-difluorobenzyl, or benzyl; and
  R$^3$ is 2-(6-methyl-pyridyl), 2-cyanophenyl, 2,3-difluorophenyl, 2-methylphenyl, 4-nitrophenyl, 4-aminophenyl, phenyl, pyridyl (e.g., 4-pyridyl), cyclohexyl, cyclopentyl, ethyl, t-butyl, tetrahydroisoquinolyl, 7-azaindolyl, or 4-methylsulfonylphenyl.
Ii or IVi
  R$^1$ is CH$_3$ or CF$_2$H;
  R$_2$ is CF$_2$H, cyclopropylmethyl, cyclopentyl, 3-tetrahydrofuranyl (preferably 3-(3R)-tetrahydrofuranyl), 2,3-difluorobenzyl, or benzyl;
  R$^3$ is H, isopropoxy, 2-(6-methyl-pyridyl), 2-cyanophenyl, 2,3-difluorophenyl, 2-methylphenyl, 4-nitrophenyl, 4-aminophenyl, phenyl, pyridyl (e.g., 4-pyridyl), cyclohexyl, cyclopentyl, ethyl, t-butyl, tetrahydroisoquinolyl, 7-azaindolyl, or 4-methylsulfonylphenyl;
  X is CH; and
  L is CH$_2$, CH$_2$CH$_2$, CH$_2$CH$_2$CH$_2$, CH$_2$CO, CH$_2$CO$_2$, SO$_2$, CH$_2$CONH, CO$_2$ or CH$_2$SO$_2$.
Ij or IVj'
  R$^1$ is CH$_3$ or CF$_2$H;
  R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl; and
  L is a bond, CH$_2$, CH$_2$CH$_2$, or CH$_2$CONH.
Ik or IVk,
  R$^1$ is CH$_3$ or CF$_2$H;
  R$_2$ is H, isopropoxy, CF$_2$H, cyclopropylmethyl, cyclopentyl, 3-tetrahydrofuranyl (preferably 3-(3R)-tetrahydrofuranyl), 2,3-difluorobenzyl, or benzyl;
  R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl; and
  L is a bond, CH$_2$, CH$_2$CH$_2$, or CH$_2$CONH.
Im or IVm
  R$^1$ is CH$_3$ or CF$_2$H;
  R$_2$ is CF$_2$H, cyclopropylmethyl, cyclopentyl, 3-tetrahydrofuranyl (preferably 3-(3R)-tetrahydrofuranyl), 2,3-difluorobenzyl, or benzyl;
  R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl;
  L is a bond, CH$_2$, CH$_2$CH$_2$, or CH$_2$CONH; and
  X is CH.
IIa or Va R$^1$ is CH$_3$ or CF$_2$H.
IIb or Vb R$^1$ is CH$_3$ or CF$_2$H; and
  R$^3$ is aryl, heterocyclic, alkyl, or cycloalkyl.
IIc or Vc R$^1$ is CH$_3$ or CF$_2$H; and
  R$^3$ is 2-(6-methyl-pyridyl), 2-cyanophenyl, 2,3-difluorophenyl, 2-methylphenyl, 4-nitrophenyl, 4-aminophenyl, phenyl, pyridyl (e.g., 4-pyridyl), cyclohexyl, cyclopentyl, ethyl, t-butyl, tetrahydroisoquinolyl, 7-azaindolyl, or 4-methylsulfonylphenyl.
IId or Vd R$^1$ is CH$_3$ or CF$_2$H; and
  R$^4$ is CH$_3$.
IIe or Ve R$^1$ is CH$_3$ or CF$_2$H;
  R$^3$ is 2-(6-methyl-pyridyl), 2-cyanophenyl, 2,3-difluorophenyl, 2-methylphenyl, 4-nitrophenyl, 4-aminophenyl, phenyl, pyridyl (e.g., 4-pyridyl), cyclohexyl, cyclopentyl, ethyl, t-butyl, tetrahydroisoquinolyl, 7-azaindolyl, or 4-methylsulfonylphenyl; and
  R$^4$ is CH$_3$.
IIf or Vf R$^1$ is CH$_3$ or CF$_2$H;
  R$^3$ is 2-(6-methyl-pyridyl), 2-cyanophenyl, 2,3-difluorophenyl, 2-methylphenyl, 4-nitrophenyl, 4-aminophenyl, phenyl, pyridyl (e.g., 4-pyridyl), cyclohexyl, cyclopentyl, ethyl, t-butyl, tetrahydroisoquinolyl, 7-azaindolyl, or 4-methylsulfonylphenyl;
  R$^4$ is CH$_3$; and
  L is CH$_2$, CH$_2$CH$_2$, CH$_2$CH$_2$CH$_2$, CH$_2$CO, CH$_2$CO$_2$, SO$_2$, or CH$_2$CONH.
IIg or Vg R$^1$ is CH$_3$ or CF$_2$H;
  R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl; and
  L is a bond, CH$_2$, CH$_2$CH$_2$, or CH$_2$CONH.
IIh or Vh R$^1$ is CH$_3$ or CF$_2$H;
  R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl;

L is a bond, CH$_2$, CH$_2$CH$_2$, or CH$_2$CONH; and
R$^4$ is CH$_3$.

IIa or VIa R$^3$ is aryl, heterocyclic, alkyl, or cycloalkyl.

IIIb or VIb R$^5$ is alkyl having 1 to 3 carbon atoms.

IIIc or VIc R$^6$ is cycloalkyl having 4 to 7 carbon atoms.

IIId or VId R$^3$ is aryl, heterocyclic, alkyl, or cycloalkyl;
R$^5$ is CH$_2$CH$_3$; and
R$^6$ is cyclopentyl.

IIIe or VIe R$^3$ is aryl, heterocyclic, alkyl, or cycloalkyl;
R$^5$ is CH$_2$CH$_3$;
R$^6$ is cyclopentyl;
X is CH; and
L is a bond, CH$_2$, CH$_2$CH$_2$, CH$_2$CH$_2$CH$_2$, CH$_2$CO, CH$_2$CO$_2$, SO$_2$, or CH$_2$CONH.

IIIf or VIf R$^3$ is 4-methoxyphenyl or 2-pyridylmethyl;
R$^5$ is CH$_2$CH$_3$;
R$^6$ is cyclopentyl;
X is CH; and
L is a bond, CH$_2$, CH$_2$CH$_2$, CH$_2$CH$_2$CH$_2$, CH$_2$CO, CH$_2$CO$_2$, SO$_2$, or CH$_2$CONH.

IIIg or VIg R$^3$ is 4-methoxyphenyl or 2-pyridylmethyl;
R$^5$ is CH$_2$CH$_3$;
R$^6$ is cyclopentyl;
X is CH; and
L is a bond or CH$_2$.

VIIa or VIIIa R$^1$ is CH$_3$;
R$^2$ is F; and
R$^3$ is substituted or unsubstituted aryl or arylalkyl.

VIIb or VIIIb R$^1$ is CH$_3$;
X is CH;
R$^2$ is F;
R$^3$ is substituted or unsubstituted phenyl or benzyl;
L is a bond; and
R$^7$ and R$^8$ are each H VIIc or VIIIc R$^1$ is CH$_3$;
R$^2$ is F;
R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl; and
L is a bond, CH$_2$, CH$_2$CH$_2$, or CH$_2$CONH.

VIId or VIIId R$^1$ is CH$_3$;
X is CH;
R$^2$ is F;
R$^3$ is phenyl, benzyl, phenethyl, cyclohexyl, 2-methoxyphenyl, 3-methoxyphenyl, 4-methoxyphenyl, 4-trifluoromethoxyphenyl, 4-bromophenyl, 4-methylbenzyl, 4-t-butylbenzyl, 2-methoxybenzyl, 3-methoxybenzyl, 3,5-dimethoxybenzyl, 3-fluorobenzyl, 2,6-difluorobenzyl, 4-fluorobenzyl, 3,4-difluorobenzyl, or 4-carboxybenzyl;
L is a bond, CH$_2$, CH$_2$CH$_2$, or CH$_2$CONH; and
R$^7$ and R$^8$ are each H.

According to preferred compounds of the invention, 5-aryl-1-substituted pyrazoles and 5-heteroaryl-1-substituted pyrazoles (e.g. Formulas IV, V, and VI) are generally preferred over 3-aryl-1-substituted pyrazoles and 3-heteroaryl-1-substituted pyrazoles (e.g. Formulas I, II, and III).

According to a further preferred compound aspect of the invention, the compounds of Formulas I, II, III, IV, V, VI, VII and VIII are selected from:

3-(3-Cyclopentyloxy-4-methoxyphenyl)pyrazole [which can also be called 3-(3-Cyclopentyloxy-4-methoxyphenyl)-1H-pyrazole];

3-(3-Cyclopentyloxy-4-methoxyphenyl)-1-(2-methylbenzyl)pyrazole [which can also be called 3-(3-Cyclopentyloxy-4-methoxyphenyl)-1-(2-methylbenzyl)-1H-pyrazole];

3-(3-Cyclopentyloxy-4-methoxyphenyl)-1-(2,3-difluorobenzyl)pyrazole [which can also be called 3-(3-Cyclopentyloxy-4-methoxyphenyl)-1-(2,3-difluorobenzyl)-1H-pyrazole];

3-(3-Cyclopentyloxy-4-methoxyphenyl)-1-(4-nitrobenzyl)pyrazole [which can also be called 3-(3-Cyclopentyloxy-4-methoxyphenyl)-1-(4-nitrobenzyl)-1H-pyrazole];

3-(4-Methoxy-3-(3R)-tetrahydrofuryloxyphenyl)-1-(2-methylbenzyl)pyrazole [which can also be called 3-[4-Methoxy-3-(3R)-tetrahydrofuranyloxyphenyl]-1-(2-methylbenzyl)-1H-pyrazole];

1-(2,3-Difluorobenzyl)-3-(4-methoxy-3-(3R)-tetrahydrofuryloxyphenyl)pyrazole [which can also be called 1-(2,3-Difluorobenzyl)-3-[4-methoxy-3-(3R)-tetrahydrofuranyloxyphenyl]-1H-pyrazole];

1-(4-Aminobenzyl)-3-(3-cyclopentyloxy-4-methoxyphenyl)pyrazole [which can also be called 1-(4-Aminobenzyl)-3-(3-cyclopentyloxy-4-methoxyphenyl)-1H-pyrazole];

3-(4-Methoxy-3-(3R)-tetrahydrofuryloxyphenyl)pyrazole [which can also be called 3-[4-Methoxy-3-(3R)-tetrahydrofuranyloxyphenyl]-1H-pyrazole];

3-(4-Methoxy-3-(3R)-tetrahydrofuryloxyphenyl)-1-(4-nitrobenzyl)pyrazole [which can also be called 3-[4-Methoxy-3-(3R)-tetrahydrofuranyloxyphenyl]-1-(4-nitrobenzyl)-1H-pyrazole];

1-(4-Aminobenzyl)-3-(4-methoxy-3-(3R)-tetrahydrofuryloxyphenyl)pyrazole [which can also be called 1-(4-Aminobenzyl)-3-[4-methoxy-3-(3R)-tetrahydrofuranyloxyphenyl]-1H-pyrazole];

3-(4-Difluoromethoxy-3-(3R)-tetrahydrofuryloxyphenyl)-1-(N-(2-methylphenyl)aminocarbonylmethyl)pyrazole [which can also be called 2-{3-[4-Difluoromethoxy-3-(3R)-tetrahydrofuranyloxyphenyl]-pyrazol-1-yl}-N-(2,-methylphenyl)acetamide];

3-[3,4-Bis(difluoromethoxy)phenyl]pyrazole [which can also be called 3-[3,4-Bis(difluoromethoxy)phenyl]-1H-pyrazole];

3-(4-Difluoromethoxy-3-(3R)-tetrahydrofuryloxyphenyl)pyrazole [which can also be called 3-[4-Difluoromethoxy-3-(3R)-tetrahydrofuranyloxyphenyl]-1H-pyrazole];

3-(4-Difluoromethoxy-3-(3R)-tetrahydrofuryloxyphenyl)-1-(N-(2,3-difluorophenyl)aminocarbonylmethyl)pyrazole [which can also be called 2-{3-[4-Difluoromethoxy-3-(3R)-tetrahydrofuranyloxyphenyl]-pyrazol-1-yl}-N-(2,3-difluorophenyl)acetamide];

3-[3,4-Bis(difluoromethoxy)phenyl]-1-(N-(2,3-difluorophenyl)aminocarbonyl-methyl)pyrazole [which can also be called 2-{3-[3,4-Bis(difluoromethoxy)-phenyl]-pyrazol-1-yl}-N-(2,3-difluorophenyl)acetamide];

3-(4-Difluoromethoxy-3-(3R)-tetrahydrofuryloxyphenyl)-1-(N-(2-(6-methylpyridyl))aminocarbonylmethyl)pyrazole [which can also be called 2-{3-[4-Difluoromethoxy-3-(3R)-tetrahydrofuranyloxyphenyl]-pyrazol-1-yl}-N-[2-(6-methylpyridyl)]acetamide];

1-(N-(2-Cyanophenyl)aminocarbonylmethyl)-3-(4-difluoromethoxy-3-(3R)-tetrahydrofuryloxyphenyl)pyrazole [which can also be called 1-N-(2-cyanophenyl)-2-{3-[4-difluoromethoxy-3-(3R)-tetrahydrofuranyloxyphenyl]-pyrazol-1-yl}acetamide];

3-(4-Difluoromethoxy-3-(3R)-tetrahydrofuryloxyphenyl)-1-(4-nitrobenzyl)pyrazole [which can also be called 3-[4-

Difluoromethoxy-3-(3R)-tetrahydrofuranyloxyphenyl]-1-(4-nitrobenzyl)-1H-pyrazole];

3-(4-Difluoromethoxy-3-(3R)-tetrahydrofuryloxyphenyl)-1-(2-methylbenzyl)pyrazole [which can also be called 3-[4-Difluoromethoxy-3-(3R)-tetrahydrofuranyloxyphenyl]-1-(2-methylbenzyl)-1H-pyrazole];

1-(2,3-Difluorobenzyl)-3-(4-difluoromethoxy-3-(3R)-tetrahydrofuryloxyphenyl)pyrazole [which can also be called 1-(2,3-Difluorobenzyl)-3-[4-difluoromethoxy-3-(3R)-tetrahydrofuranyloxyphenyl]-1H-pyrazole];

3-(2-Acetyl-7-methoxybenzofuran-4-yl)pyrazole [which can also be called 3-(2-Acetyl-7-methoxybenzofuran-4-yl)-1H-pyrazole];

1-(4-Aminobenzyl)-3-(4-difluoromethoxy-3-(3R)-tetrahydrofuryloxyphenyl)pyrazole [which can also be called 1-(4-Aminobenzyl)-3-[4-difluoromethoxy-3-(3R)-tetrahydrofuranyloxyphenyl]-1H-pyrazole];

1-(2,3-Difluorobenzyl)-3-(4-methoxy-3-(3S)-tetrahydrofuryloxyphenyl)pyrazole [which can also be called 1-(2,3-Difluorobenzyl)-3-[4-methoxy-3-(3S)-tetrahydrofuranyloxyphenyl]-1H-pyrazole];

1-Cyclohexylmethyl-3-(4-methoxy-3-(3R)-tetrahydrofuryloxyphenyl)pyrazole [which can also be called 1-Cyclohexylmethyl-3-[4-methoxy-3-(3R)-tetrahydrofuranyloxyphenyl]-1H-pyrazole];

3-(4-Methoxy-3-(3R)-tetrahydrofuryloxyphenyl)-1-(3-phenpropyl)pyrazole [which can also be called 3-[4-Methoxy-3-(3R)-tetrahydrofuranyloxyphenyl]-1-(3-phenpropyl)-1H-pyrazole];

3-(4-Methoxy-3-(3R)-tetrahydrofuryloxyphenyl)-1-(4-pyridylmethyl)pyrazole [which can also be called 3-[4-Methoxy-3-(3R)-tetrahydrofuranyloxyphenyl]-1-(4-pyridylmethyl)-1H-pyrazole];

1-Ethylsulfonyl-3-(4-methoxy-3-(3R)-tetrahydrofuryloxyphenyl)pyrazole [which can also be called 1-Ethylsulfonyl-3-[4-methoxy-3-(3R)-tetrahydrofuranyloxyphenyl]-1H-pyrazole];

3-(4-Methoxy-3-(3R)-tetrahydrofuryloxyphenyl)-1-(1-propyl)pyrazole [which can also be called 3-[4-Methoxy-3-(3R)-tetrahydrofuranyloxyphenyl]-1-(1-propyl)-1H-pyrazole];

1-Benzylsulfonyl-3-(4-methoxy-3-(3R)-tetrahydrofuryloxyphenyl)pyrazole [which can also be called 1-Benzylsulfonyl-3-[4-methoxy-3-(3R)-tetrahydrofuranyloxyphenyl]-1H-pyrazole];

3-(4-Methoxy-3-(3R)-tetrahydrofuryloxyphenyl)-1-(2-pyridylmethyl)pyrazole [which can also be called 3-[4-Methoxy-3-(3R)-tetrahydrofuranyloxyphenyl]-1-(2-pyridylmethyl)-1H-pyrazole];

3-[(1-Cyclopentyl-3-ethylindazol)-6-yl]pyrazole [which can also be called 3-[(1-Cyclopentyl-3-ethylindazol)-6-yl]-1H-pyrazole];

3-(4-Methoxy-3-(3R)-tetrahydrofuryloxyphenyl)pyrazole-1-ylacetic acid [which can also be called 2-{3-[4-Methoxy-3-(3R)-tetrahydrofuranyloxyphenyl]-1H-pyrazol-1-yl}acetic acid];

3-(3-Benzyloxy-4-methoxyphenyl)pyrazole [which can also be called 3-(3-Benzyloxy-4-methoxyphenyl)-1H-pyrazole];

3-(4-Difluoromethoxy-3-(3R)-tetrahydrofuryloxyphenyl)pyrazole-1-ylacetic acid [which can also be called 2-{3-[4-Difluoromethoxy-3-(3R)-tetrahydrofuranyloxyphenyl]pyrazole-1-yl}acetic acid]

1-Cyclohexylmethyl-5-(4-methoxy-3-(3R)-tetrahydrofuryloxyphenyl)pyrazole [which can also be called 1-Cyclohexylmethyl-5-[4-methoxy-3-(3R)-tetrahydrofuranyloxyphenyl]-1H-pyrazole];

3-(3-Benzyloxy-4-methoxyphenyl)-1-(2,3-difluorobenzyl)pyrazole [which can also be called 3-(3-Benzyloxy-4-methoxyphenyl)-1-(2,3-difluorobenzyl)-1H-pyrazole];

3-(4-Methoxy-3-(3R)-tetrahydrofuryloxyphenyl)-1-[N-(1,2,3,4-tetrahydroisoquinolyl)carbonylmethyl]pyrazole [which can also be called 3-[4-Methoxy-3-(3R)-tetrahydrofuranyloxyphenyl]-1-[N-(1,2,3,4-tetrahydroisoquinolyl)carbonylmethyl]-1H-pyrazole];

1-[N-(7-Azaindolyl)carbonylmethyl]-3-(4-methoxy-3-(3R)-tetrahydrofuryloxyphenyl)pyrazole [which can also be called 1-[N-(7-Azaindolyl)carbonylmethyl]-3-[4-methoxy-3-(3R)-tetrahydrofuranyloxyphenyl]-1H-pyrazole];

3-(2-Acetyl-7-methoxybenzofuran-4-yl)-1-(2,3-difluorobenzyl)pyrazole [which can also be called 3-(2-Acetyl-7-methoxybenzofuran-4-yl)-1-(2,3-difluorobenzyl)-1H-pyrazole];

3-(2-Acetyl-7-methoxybenzofuran-4-yl)-1-(4-methylsulfonylbenzyl)pyrazole [which can also be called 3-(2-Acetyl-7-methoxybenzofuran-4-yl)-1-(4-methylsulfonylbenzyl)-1H-pyrazole];

1-(2,3-Difluorobenzyl)-3-[3-(2,3-difluorobenzyloxy)-4-methoxyphenyl]pyrazole [which can also be called 1-(2,3-Difluorobenzyl)-3-[3-(2,3-difluorobenzyloxy)-4-methoxyphenyl]-1H-pyrazole];

3-[3-(2,3-Difluorobenzyloxy)-4-methoxyphenyl]pyrazole [which can also be called 3-[3-(2,3-Difluorobenzyloxy)-4-methoxyphenyl]-1H-pyrazole];

1-(2,3-Difluorobenzyl)-3-(3-hydroxy-4-methoxyphenyl)pyrazole [which can also be called 1-(2,3-Difluorobenzyl)-3-(3-hydroxy-4-methoxyphenyl)-1H-pyrazole];

3-(2-Acetyl-7-methoxybenzofuran-4-yl)-1-(2-methylbenzyl)pyrazole [which can also be called 3-(2-Acetyl-7-methoxybenzofuran-4-yl)-1-(2-methylbenzyl)-1H-pyrazole];

3-(4-Methoxy-3-(3R)-tetrahydrofuryloxyphenyl)-1-(2-phenethyl)pyrazole [which can also be called 3-[4-Methoxy-3-(3R)-tetrahydrofuranyloxyphenyl]-1-(2-phenethyl)-1H-pyrazole];

1-(Acetophenone-2-yl)-3-(4-methoxy-3-(3R)-tetrahydrofuryloxyphenyl)pyrazole [which can also be called 2-{3-[4-methoxy-3-(3R)-tetrahydrofuranyloxyphenyl]-pyrazol-1-yl}-1-phenyl-1-ethanone];

1-Benzyl-3-(4-methoxy-3-(3R)-tetrahydrofuryloxyphenyl)pyrazole [which can also be called 1-Benzyl-3-[4-methoxy-3-(3R)-tetrahydrofuranyloxyphenyl]-1H-pyrazole];

1-Cyclopentyl-3-(4-methoxy-3-(3R)-tetrahydrofuryloxyphenyl)pyrazole [which can also be called 1-Cyclopentyl-3-[4-methoxy-3-(3R)-tetrahydrofuranyloxyphenyl]-1H-pyrazole];

3-[(1-Cyclopentyl-3-ethylindazol)-6-yl]-1-(2,3-difluorobenzyl)-1H-pyrazole;

3-[(1-Cyclopentyl-3-ethylindazol)-6-yl]-1-(4-carboxyphenyl)-1H-pyrazole;

3-[(1-Cyclopentyl-3-ethylindazol)-6-yl]-1-(4-methoxyphenyl)-1H-pyrazole;

3-[(1-Cyclopentyl-3-ethylindazol)-6-yl])-1-(2-methylbenzyl)pyrazole [which can also be called 3-[(1-Cyclopentyl-3-ethylindazol)-6-yl])-1-(2-methylbenzyl)-1H-pyrazole];

3-[(1-Cyclopentyl-3-ethylindazol)-6-yl])-1-(4-methylsulfonylbenzyl)pyrazole [which can also be called 3-[(1-Cyclopentyl-3-ethylindazol)-6-yl])-1-(4-methylsulfonylbenzyl)-1H-pyrazole];

3-[(1-Cyclopentyl-3-ethylindazol)-6-yl])-1-(2-pyridylmethyl)pyrazole [which can also be called 3-[(1-Cyclopentyl-3-ethylindazol)-6-yl])-1-(2-pyridylmethyl)-1H-pyrazole;

5-[(1-Cyclopentyl-3-ethylindazol)-6-yl])-1-(2-pyridylmethyl)-1H-pyrazole;
3-[4-Methoxy-3-(3R)-tetrahydrofuranyloxyphenyl]-1-[2-(6-methylpyridyl)-1H-pyrazole;
1-Cyclohexylmethyl-5-(4-methoxy-3-(3S)-tetrahydrofuryloxyphenyl)pyrazole [which can also be called 1-Cyclohexylmethyl-5-[4-methoxy-3-(3S)-tetrahydrofuranyloxyphenyl]-1H-pyrazole];
1-Cyclohexylmethyl-3-(4-methoxy-3-(3S)-tetrahydrofuryloxyphenyl)pyrazole [which can also be called 1-Cyclohexylmethyl-3-[4-methoxy-3-(3S)-tetrahydrofuranyloxyphenyl]-1H-pyrazole];
3-(3,4-Dimethoxyphenyl)-1-(tert-butyloxycarbonyl)pyrazole [which can also be called tert-Butyl [3-(3,4-Dimethoxyphenyl)-pyrazol-1-yl]carboxylate];
3-(4-Methoxy-3-(3R)-tetrahydrofuryloxyphenyl)-1-(methylsulfonylbenzyl)pyrazole [which can also be called 3-[4-Methoxy-3-(3R)-tetrahydrofuranyloxyphenyl]-1-(methylsulfonylbenzyl)-1H-pyrazole];
Isopropyl 2-{5-[4-methoxy-3-(3R)-tetrahydrofuranyloxyphenyl]-pyrazol-1-yl}acetate;
1-(2,3-Difluorobenzyl)-5-[4-methoxy-3-(3R)-tetrahydrofuranyl-oxyphenyl]-1H-pyrazole;
5-(3-Cyclopentyloxy-4-methoxyphenyl)-3-methyl-1-phenyl-1H-pyrazole;
1-Benzyl-5-[4-methoxy-3-(3R)-tetrahydrofuranyloxyphenyl]-3-trifluoromethyl-1H-pyrazole;
5-[4-Methoxy-3-(3R)-tetrahydrofuranyloxyphenyl]-1-(4-trifluoromethoxybenzyl)-1H-pyrazole;
5-[4-Methoxy-3-(3R)-tetrahydrofuranyloxyphenyl]-1-phenyl-3-trifluoromethyl-1H-pyrazole;
Ethyl[5-(4-methoxy-3-(3R)-tetrahydrofuranyloxyphenyl)-3-trifluoromethyl-1H-pyrazol-1-yl]acetate;
[5-(4-Methoxy-3-(3R)-tetrahydrofuranyloxyphenyl)-3-trifluoromethyl-1H-pyrazol-1-yl]acetic acid;
Isopropyl[5-(4-methoxy-3-(3R)-tetrahydrofuranyloxyphenyl)-3-trifluoromethyl-1H-pyrazol-1-yl]acetate;
1-(2,3-Difluorobenzyl)-5-(3,4-dimethoxyphenyl)-1H-pyrazole;
N-(3-Fluorophenyl)-2-{5-[4-methoxy-3-(3R)-tetrahydrofuranyloxyphenyl]-3-trifluoromethyl-pyrazol-1-yl}acetamide;
N-(5-Methylthiazol-2-yl)-2-{5-[4-methoxy-3-(3R)-tetrahydrofuranyloxyphenyl]-3-trifluoromethyl-pyrazol-1-yl}acetamide;
5-[4-Methoxy-3-(3R)-tetrahydrofuranyloxyphenyl]-1-(4-methylbenzyl)-1H-pyrazole;
1-(4-tert-Butylbenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-trifluoromethylbenzyl)-1H-pyrazole;
1-(3,4-Difluorobenzyl)-5-[4-methoxy-3-(3R)-tetrahydrofuranyloxyphenyl]-1H-pyrazole;
1-(2-Fluorobenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(3-nitrobenzyl)-1H-pyrazole;
5-[4-Methoxy-3-(3R)-tetrahydrofuranyloxyphenyl]-1-(4-methoxycarbonylbenzyl)-1H-pyrazole;
1-Benzyl-5-[4-methoxy-3-(3R)-tetrahydrofuranyloxyphenyl]-3-methyl-1H-pyrazole;
5-[4-Methoxy-3-(3R)-tetrahydrofuranyloxyphenyl]-3-methyl-1-phenyl-1H-pyrazole;
1-(3-Fluorobenzyl)-5-[4-methoxy-3-(3R)-tetrahydrofuranyloxyphenyl]-1H-pyrazole;
1-(3,5-Dimethoxybenzyl)-5-[4-methoxy-3-(3R)-tetrahydrofuranyloxyphenyl]-1H-pyrazole;
1-Cyclohexyl-5-[4-methoxy-3-(3R)-tetrahydrofuranyloxyphenyl]-3-methyl-1H-pyrazole;
1-(3-Fluorobenzyl)-5-[4-methoxy-3-(3R)-tetrahydrofuranyloxyphenyl]-3-trifluoromethyl-1H-pyrazole;
5-[4-Methoxy-3-(3R)-tetrahydrofuranyloxyphenyl]-1-phenyl-1H-pyrazole;
1-Cyclohexyl-5-[4-methoxy-3-(3R)-tetrahydrofuranyloxyphenyl]-1H-pyrazole;
Ethyl 1-Benzyl-5-[4-methoxy-3-(3R)-tetrahydrofuranyloxyphenyl]-1H-pyrazole-3-carboxylate;
1-Benzyl-5-[4-methoxy-3-(3R)-tetrahydrofuranyloxyphenyl]-1H-pyrazole;
1-(3-Methoxybenzyl)-5-[4-methoxy-3-(3R)-tetrahydrofuranyloxyphenyl]-1H-pyrazole;
1-(4-Fluorobenzyl)-5-[4-methoxy-3-(3R)-tetrahydrofuranyloxyphenyl]-1H-pyrazole;
1-(2-Methoxybenzyl)-5-[4-methoxy-3-(3R)-tetrahydrofuranyloxyphenyl]-3-methyl-1H-pyrazole;
1-(1-Butyl)-5-[4-methoxy-3-(3R)-tetrahydrofuranyloxyphenyl]-3-methyl-1H-pyrazole;
1-(2-Fluorophenyl)-5-[4-methoxy-3-(3R)-tetrahydrofuranyloxyphenyl]-3-methyl-1H-pyrazole;
1-(4-Chlorophenyl)-5-[4-methoxy-3-(3R)-tetrahydrofuranyloxyphenyl]-3-methyl-1H-pyrazole;
[5-(4-Methoxy-3-(3R)-tetrahydrofuranyloxyphenyl)-1H-pyrazol-1-yl]acetic acid;
N-Cyclopropyl-2-{5-[4-methoxy-3-(3R)-tetrahydrofuranyloxyphenyl]-pyrazol-1-yl}acetamide;
N-Isopropyl-2-{5-[4-methoxy-3-(3R)-tetrahydrofuranyloxyphenyl]-pyrazol-1-yl}acetamide;
3-Ethyl-5-[4-methoxy-3-(3R)-tetrahydrofuranyloxyphenyl]-1-(2-methoxybenzyl)-1H-pyrazole;
1-Cyclohexyl-3-ethyl-5-[4-methoxy-3-(3R)-tetrahydrofuranyloxyphenyl]-1H-pyrazole;
1-Benzyl-3-ethyl-5-[4-methoxy-3-(3R)-tetrahydrofuranyloxyphenyl]-1H-pyrazole;
Ethyl 3-ethyl-[5-(4-methoxy-3-(3R)-tetrahydrofuranyloxyphenyl)-1H-pyrazol-1-yl]acetate;
5-[4-Methoxy-3-(3R)-tetrahydrofuranyloxyphenyl]-1-(4-methoxyphenyl)-1H-pyrazole;
5-[4-Methoxy-3-(3R)-tetrahydrofuranyloxyphenyl]-1-(2-phenylethyl)-1H-pyrazole;
1-Benzyl-5-[4-methoxy-3-(3R)-tetrahydrofuranyloxyphenyl]-1H-pyrazole-3-carboxylic acid;
1-(2,3-Dimethylphenyl)-3-ethyl-5-[4-methoxy-3-(3R)-tetrahydrofuranyloxyphenyl]-1H-pyrazole;
1-(4-Fluorophenyl)-5-[4-methoxy-3-(3R)-tetrahydrofuranyloxyphenyl]-1H-pyrazole;
1-(3,4-Dimethylphenyl)-3-ethyl-5-[4-methoxy-3-(3R)-tetrahydrofuranyloxyphenyl]-1H-pyrazole;
3-Ethyl-5-[4-methoxy-3-(3R)-tetrahydrofuranyloxyphenyl]-1-(2-methylphenyl)-1H-pyrazole;
1-(2-Benzothiazolyl)-5-[4-methoxy-3-(3R)-tetrahydrofuranyloxyphenyl]-3-methyl-1H-pyrazole;
1-(3,4-Dimethylphenyl)-5-[4-methoxy-3-(3R)-tetrahydrofuranyloxyphenyl]-3-methyl-1H-pyrazole;
2-{5-[4-Methoxy-3-(3R)-tetrahydrofuranyloxyphenyl]-pyrazol-1-yl}-N-phenylacetamide;
N,N-Diethyl-2-{5-[4-methoxy-3-(3R)-tetrahydrofuranyloxyphenyl]-pyrazol-1-yl}acetamide;
1-(2,3-Dimethylphenyl)-5-[4-methoxy-3-(3R)-tetrahydrofuranyloxyphenyl]-3-methyl-1H-pyrazole;
1-{1-Benzyl-5-[4-methoxy-3-(3R)-tetrahydrofuranyloxyphenyl]-1H-pyrazol-3-yl}ethanone;
2-{1-Benzyl-5-[4-methoxy-3-(3R)-tetrahydrofuranyloxyphenyl]-1H-pyrazol-3-yl}ethanone;

{1-Benzyl-5-[4-methoxy-3-(3R)-tetrahydrofuranyloxyphenyl]-1H-pyrazol-3-yl}methanone;
1-(4-Bromophenyl)-5-[4-methoxy-3-(3R)-tetrahydrofuranyloxyphenyl]-1H-pyrazole;
5-[4-Methoxy-3-(3R)-tetrahydrofuranyloxyphenyl]-3-methyl-1-(3-nitrophenyl)-1H-pyrazole;
5-[4-Methoxy-3-(3R)-tetrahydrofuranyloxyphenyl]-3-methyl-1-(2-methylphenyl)-1H-pyrazole;
1-(3,4-Difluorobenzyl)-5-(3-fluoro-4-methoxyphenyl)-1H-pyrazole;
5-(3-Fluoro-4-methoxyphenyl) 1-(4-methoxycarbonylbenzyl)-1H-pyrazole;
1-(2,6-Difluorobenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-trifluoromethoxyphenyl)-1H-pyrazole;
5-[4-Methoxy-3-(3R)-tetrahydrofuranyloxyphenyl]-1-(2-pyridyl)-1H-pyrazole;
1-(2-Benzothiazolyl)-5-[4-methoxy-3-(3R)-tetrahydrofuranyloxyphenyl]-1H-pyrazole;
1-(4-Fluorobenzyl)-5-(3-fluoro-4-methoxyphenyl)-1H-pyrazole;
5-[4-Methoxy-3-(3R)-tetrahydrofuranyloxyphenyl]-3-methyl-1-(2-phenylethyl)-1H-pyrazole;
5-[4-Methoxy-3-(3R)-tetrahydrofuranyloxyphenyl]-3-methyl-1-(4-trifluoromethoxyphenyl)-1H-pyrazole;
5-[4-Methoxy-3-(3R)-tetrahydrofuranyloxyphenyl]-3-methyl-1-(2-quinoxalinyl)-1H-pyrazole;
5-[4-Methoxy-3-(3R)-tetrahydrofuranyloxyphenyl]-1-[4-(4-morpholinyl)phenyl]-1H-pyrazole;
5-(3-Fluoro-4-methoxyphenyl)-1-(4-methoxyphenyl)-1H-pyrazole;
1-Benzyl-5-(3-fluoro-4-methoxyphenyl)-1H-pyrazole;
1-(2-Methoxyphenyl)-5-[4-methoxy-3-(3R)-tetrahydrofuranyloxyphenyl]-1H-pyrazole;
1-[2-(6-Fluoropyridyl)]-5-[4-methoxy-3-(3R)-tetrahydrofuranyloxyphenyl]-1H-pyrazole;
1-(4-Carboxybenzyl)-5-[4-methoxy-3-(3R)-tetrahydrofuranyloxyphenyl]-1H-pyrazole;
Ethyl 2-{5-[4-methoxy-3-(3R)-tetrahydrofuranyloxyphenyl]pyrazol-1-yl}acetate;
1-(2-Hydroxyethyl)-5-[4-methoxy-3-(3R)-tetrahydrofuranyloxyphenyl]-1H-pyrazole;
1-(2-Methoxyethyl)-5-[4-methoxy-3-(3R)-tetrahydrofuranyloxyphenyl]-1H-pyrazole;
1-(2-Cyclopropylmethoxyethyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-methoxyphenyl)-3-methyl-1H-pyrazole;
5-[4-Methoxy-3-(3R)-tetrahydrofuranyloxyphenyl]-1-(2-methoxycarbonyl-3-thienyl)-3-methyl-1H-pyrazole;
1-[2-(6-Fluoropyridyl)]-5-[4-methoxy-3-(3R)-tetrahydrofuranyloxyphenyl]-3-methyl-1H-pyrazole;
5-[4-Methoxy-3-(3R)-tetrahydrofuranyloxyphenyl]-3-methyl-1-(2-pyridyl)-1H-pyrazole;
1-[2-(6-Chloropyridyl)]-5-[4-methoxy-3-(3R)-tetrahydrofuranyloxyphenyl]-3-methyl-1H-pyrazole;
1-(4-Carboxyphenyl)-5-[4-methoxy-3-(3R)-tetrahydrofuranyloxyphenyl]-1H-pyrazole;
1-(4-Carboxybenzyl)-5-(3-fluoro-4-methoxyphenyl)-1H-pyrazole;
5-(3,4-Dimethoxyphenyl)-1-(4-fluorobenzyl)-1H-pyrazole;
5-(3,4-Dimethoxyphenyl)-1-(4-methoxyphenyl)-1H-pyrazole;

and physiologically acceptable salts thereof, wherein in each case the compound can be in the form of a mixture of enantiomers such as the racemate or a mixture of diastereomers, or can be in the form of a single enantiomer or a single diastereomer.

According to a further compound aspect of the invention, the compounds of formulas I, II, III, IV, V, and VI are selected from:

3-(3-Cyclopentyloxy-4-methoxyphenyl)pyrazole
3-(3-Cyclopentyloxy-4-methoxyphenyl)-1-(2-methylbenzyl)pyrazole
3-(3-Cyclopentyloxy-4-methoxyphenyl)-1-(2,3-difluorobenzyl)pyrazole
3-(3-Cyclopentyloxy-4-methoxyphenyl)-1-(4-nitrobenzyl)pyrazole
3-(4-Methoxy-3-(3R)-tetrahydrofuryloxyphenyl)-1-(2-methylbenzyl)pyrazole
1-(2,3-Difluorobenzyl)-3-(4-methoxy-3-(3R)-tetrahydrofuryloxyphenyl)pyrazole
1-(4-Aminobenzyl)-3-(3-cyclopentyloxy-4-methoxyphenyl)pyrazole
3-(4-Methoxy-3-(3R)-tetrahydrofuryloxyphenyl)pyrazole
3-(4-Methoxy-3-(3R)-tetrahydrofuryloxyphenyl)-1-(4-nitrobenzyl)pyrazole
1-(4-Aminobenzyl)-3-(4-methoxy-3-(3R)-tetrahydrofuryloxyphenyl)pyrazole
3-(4-Difluoromethoxy-3-(3R)-tetrahydrofuryloxyphenyl)-1-(N-(2-methylphenyl)aminocarbonylmethyl)pyrazole
3-[3,4-Bis(difluoromethoxy)phenyl]pyrazole
3-(4-Difluoromethoxy-3-(3R)-tetrahydrofuryloxyphenyl)pyrazole
3-(4-Difluoromethoxy-3-(3R)-tetrahydrofuryloxyphenyl)-1-(N-(2,3-difluorophenyl)aminocarbonylmethyl)pyrazole
3-[3,4-Bis(difluoromethoxy)phenyl]-1-(N-(2,3-difluorophenyl)aminocarbonylmethyl)pyrazole
3-(4-Difluoromethoxy-3-(3R)-tetrahydrofuryloxyphenyl)-1-(N-(2-(6-methylpyridyl))aminocarbonylmethyl)pyrazole
1-(N-(2-cyanophenyl)aminocarbonylmethyl)-3-(4-difluoromethoxy-3-(3R)-tetrahydrofuryloxyphenyl)pyrazole
3-(4-Difluoromethoxy-3-(3R)-tetrahydrofuryloxyphenyl)-1-(4-nitrobenzyl)pyrazole
3-(4-Difluoromethoxy-3-(3R)-tetrahydrofuryloxyphenyl)-1-(2-methylbenzyl)pyrazole
1-(2,3-Difluorobenzyl)-3-(4-difluoromethoxy-3-(3R)-tetrahydrofuryloxyphenyl)pyrazole
3-(2-Acetyl-7-methoxybenzofuran-4-yl)pyrazole
1-(4-Aminobenzyl)-3-(4-difluoromethoxy-3-(3R)-tetrahydrofuryloxyphenyl)pyrazole,
1-(2,3-Difluorobenzyl)-3-(4-methoxy-3-(3S)-tetrahydrofuryloxyphenyl)pyrazole,
1-Cyclohexylmethyl-3-(4-methoxy-3-(3R)-tetrahydrofuryloxyphenyl)pyrazole,
3-(4-Methoxy-3-(3R)-tetrahydrofuryloxyphenyl)-1-(3-phenpropyl)pyrazole,
3-(4-Methoxy-3-(3R)-tetrahydrofuryloxyphenyl)-1-(4-pyridylmethyl)pyrazole,
1-Ethylsulfonyl-3-(4-methoxy-3-(3R)-tetrahydrofuryloxyphenyl)pyrazole,
3-(4-Methoxy-3-(3R)-tetrahydrofuryloxyphenyl)-1-(1-propyl)pyrazole,
1-Benzylsulfonyl-3-(4-methoxy-3-(3R)-tetrahydrofuryloxyphenyl)pyrazole,
3-(4-Methoxy-3-(3R)-tetrahydrofuryloxyphenyl)-1-(2-pyridylmethyl)pyrazole,
3-[(1-Cyclopentyl-3-ethylindazole)-6-yl]pyrazole,
3-(4-Methoxy-3-(3R)-tetrahydrofuryloxyphenyl)pyrazole-1-ylacetic acid,
3-(3-Benzyloxy-4-methoxyphenyl)pyrazole, 3-(4-Difluoromethoxy-3-(3R)-tetrahydrofuryloxyphenyl)pyrazole-1-ylacetic acid,
1-Cyclohexylmethyl-5-(4-methoxy-3-(3R)-tetrahydrofuryloxyphenyl)pyrazole,
3-(3-Benzyloxy-4-methoxyphenyl)-1-(2,3-difluorobenzyl)pyrazole,
3-(4-Methoxy-3-(3R)-tetrahydrofuryloxyphenyl)-1-[N-(1,2,3,4-tetrahydroisoquinolyl)carbonylmethyl]pyrazole,
1-[N-(7-Azaindolyl)carbonylmethyl]-3-(4-methoxy-3-(3R)-tetrahydrofuryloxyphenyl)pyrazole,
3-(2-Acetyl-7-methoxybenzofuran-4-yl)-1-(2,3-difluorobenzyl)pyrazole,
3-(2-Acetyl-7-methoxybenzofuran-4-yl)-1-(4-methylsulfonylbenzyl)pyrazole,
1-(2,3-Difluorobenzyl)-3-[3-(2,3-difluorobenzyloxy)-4-methoxyphenyl]pyrazole,
3-[3-(2,3-Difluorobenzyloxy)-4-methoxyphenyl]pyrazole,
1-(2,3-Difluorobenzyl)-3-(3-hydroxy-4-methoxyphenyl)pyrazole,
3-(2-Acetyl-7-methoxybenzofuran-4-yl)-1-(2-methylbenzyl)pyrazole,
3-(4-Methoxy-3-(3R)-tetrahydrofuryloxyphenyl)-1-(2-phenethyl)pyrazole,
1-(Acetophenone-2-yl)-3-(4-methoxy-3-(3R)-tetrahydrofuryloxyphenyl)pyrazole,
1-Benzyl-3-(4-methoxy-3-(3R)-tetrahydrofuryloxyphenyl)pyrazole,
1-Cyclopentyl-3-(4-methoxy-3-(3R)-tetrahydrofuryloxyphenyl)pyrazole,
3-[(1-Cyclopentyl-3-ethylindazole)-6-yl]-1-(2,3-difluorophenyl)pyrazole,
3-[(1-Cyclopentyl-3-ethylindazole)-6-yl])-1-(2-methylbenzyl)pyrazole,
3-[(1-Cyclopentyl-3-ethylindazole)-6-yl])-1-(4-methylsulfonylbenzyl)pyrazole,
3-[(1-Cyclopentyl-3-ethylindazole)-6-yl])-1-(2-pyridylmethyl)pyrazole,
3-(4-Methoxy-3-(3R)-tetrahydrofuryloxyphenyl)-1-pyrazole,
1-Cyclohexylmethyl-5-(4-methoxy-3-(3S)-tetrahydrofuryloxyphenyl)pyrazole,
1-Cyclohexylmethyl-3-(4-methoxy-3-(3S)-tetrahydrofuryloxyphenyl)pyrazole,
3-(3,4-Dimethoxyphenyl)-1-(tert-butyloxycarbonyl)pyrazole,
3-(4-Methoxy-3-(3R)-tetrahydrofuryloxyphenyl)-1-(methylsulfonylbenzyl)pyrazole,
1-Isopropyloxycarbonylmethyl-5-(4-methoxy-3-(3R)-tetrahydrofuranylphenyl)pyrazole,
1-(2,3-Difluorobenzyl)-5-(4-methoxy-3-(3R)-tetrahydrofuranylphenyl)pyrazole, or physiologically acceptable salts thereof, wherein in each case the compound can be in the form of a mixture of enantiomers such as the racemate or a mixture of diastereomers, or can be in the form of a single enantiomer or a single diastereomer.

According to further compound aspect of the invention, the compound of formulas I, II, III, IV, V, or VI is selected from:
3-(3-Cyclopentyloxy-4-methoxyphenyl)-1-(2,3-difluorobenzyl)pyrazole
1-(2,3-Difluorobenzyl)-3-(4-methoxy-3-(3R)-tetrahydrofuryloxyphenyl)pyrazole
1-(4-Aminobenzyl)-3-(3-cyclopentyloxy-4-methoxyphenyl)pyrazole
3-(4-Difluoromethoxy-3-(3R)-tetrahydrofuryloxyphenyl)-1-(N-(2,3-difluorophenyl)aminocarbonylmethyl)pyrazole
3-(4-Difluoromethoxy-3-(3R)-tetrahydrofuryloxyphenyl)-1-(N-(2-(6-methylpyridyl))aminocarbonylmethyl)pyrazole
1-(N-(2-cyanophenyl)aminocarbonylmethyl)-3-(4-difluoromethoxy-3-(3R)-tetrahydrofuryloxyphenyl)pyrazole
3-(4-Difluoromethoxy-3-(3R)-tetrahydrofuryloxyphenyl)-1-(4-nitrobenzyl)pyrazole
1-(2,3-Difluorobenzyl)-3-(4-difluoromethoxy-3-(3R)-tetrahydrofuryloxyphenyl)pyrazole
3-(2-Acetyl-7-methoxybenzofuran-4-yl)pyrazole,
3-[(1-Cyclopentyl-3-ethylindazole)-6-yl]pyrazole,
1-Cyclohexylmethyl-5-(4-methoxy-3-(3R)-tetrahydrofuryloxyphenyl)pyrazole,
3-(2-Acetyl-7-methoxybenzofuran-4-yl)-1-(4-methylsulfonylbenzyl)pyrazole,
3-[(1-Cyclopentyl-3-ethylindazole)-6-yl]-1-(2,3-difluorophenyl)pyrazole,
3-[(1-Cyclopentyl-3-ethylindazole)-6-yl])-1-(4-methylsulfonylbenzyl)pyrazole,
3-[(1-Cyclopentyl-3-ethylindazole)-6-yl])-1-(2-pyridylmethyl)pyrazole,
1-Isopropyloxycarbonylmethyl-5-(4-methoxy-3-(3R)-tetrahydrofuranylphenyl)pyrazole,
1-(2,3-Difluorobenzyl)-5-(4-methoxy-3-(3R)-tetrahydrofuranylphenyl)pyrazole, or physiologically acceptable salts thereof, wherein in each case the compound can be in the form of a mixture of enantiomers such as the racemate, or a mixture of diastereomers, or can be in the form of a single enantiomer or a single diastereomer.

According to a further preferred method aspect of the invention, the compounds of Formulas I, II, III, IV, V, VI, VII and VIII are selected from:
3-(3-Cyclopentyloxy-4-methoxyphenyl)pyrazole [which can also be called 3-(3-Cyclopentyloxy-4-methoxyphenyl)-1H-pyrazole];
3-(3-Cyclopentyloxy-4-methoxyphenyl)-1-(2-methylbenzyl)pyrazole [which can also be called 3-(3-Cyclopentyloxy-4-methoxyphenyl)-1-(2-methylbenzyl)-1H-pyrazole];
3-(3-Cyclopentyloxy-4-methoxyphenyl)-1-(2,3-difluorobenzyl)pyrazole [which can also be called 3-(3-Cyclopentyloxy-4-methoxyphenyl)-1-(2,3-difluorobenzyl)-1H-pyrazole];
3-(3-Cyclopentyloxy-4-methoxyphenyl)-1-(4-nitrobenzyl)pyrazole [which can also be called 3-(3-Cyclopentyloxy-4-methoxyphenyl)-1-(4-nitrobenzyl)-1H-pyrazole];
3-(4-Methoxy-3-(3R)-tetrahydrofuryloxyphenyl)-1-(2-methylbenzyl)pyrazole [which can also be called 3-[4-Methoxy-3-(3R)-tetrahydrofuranyloxyphenyl]-1-(2-methylbenzyl)-1H-pyrazole];
1-(2,3-Difluorobenzyl)-3-(4-methoxy-3-(3R)-tetrahydrofuryloxyphenyl)pyrazole [which can also be called 1-(2,3-Difluorobenzyl)-3-[4-methoxy-3-(3R)-tetrahydrofuranyloxyphenyl]-1H-pyrazole];
1-(4-Aminobenzyl)-3-(3-cyclopentyloxy-4-methoxyphenyl)pyrazole [which can also be called 1-(4-Aminobenzyl)-3-(3-cyclopentyloxy-4-methoxyphenyl)-1H-pyrazole];
3-(4-Methoxy-3-(3R)-tetrahydrofuryloxyphenyl)pyrazole [which can also be called 3-[4-Methoxy-3-(3R)-tetrahydrofuranyloxyphenyl]-1H-pyrazole];

3-(4-Methoxy-3-(3R)-tetrahydrofuryloxyphenyl)-1-(4-nitrobenzyl)pyrazole [which can also be called 3-[4-Methoxy-3-(3R)-tetrahydrofuranyloxyphenyl]-1-(4-nitrobenzyl)-1H-pyrazole];

1-(4-Aminobenzyl)-3-(4-methoxy-3-(3R)-tetrahydrofuryloxyphenyl)pyrazole [which can also be called 1-(4-Aminobenzyl)-3-[4-methoxy-3-(3R)-tetrahydrofuranyloxyphenyl]-1H-pyrazole];

3-(4-Difluoromethoxy-3-(3R)-tetrahydrofuryloxyphenyl)-1-(N-(2-methylphenyl)aminocarbonylmethyl)pyrazole [which can also be called 2-{3-[4-Difluoromethoxy-3-(3R)-tetrahydrofuranyloxyphenyl]-pyrazol-1-yl}-N-(2,-methylphenyl)acetamide];

3-[3,4-Bis(difluoromethoxy)phenyl]pyrazole [which can also be called 3-[3,4-Bis(difluoromethoxy)phenyl]-1H-pyrazole];

3-(4-Difluoromethoxy-3-(3R)-tetrahydrofuryloxyphenyl)pyrazole [which can also be called 3-[4-Difluoromethoxy-3-(3R)-tetrahydrofuranyloxyphenyl]-1H-pyrazole];

3-(4-Difluoromethoxy-3-(3R)-tetrahydrofuryloxyphenyl)-1-(N-(2,3-difluorophenyl)aminocarbonylmethyl)pyrazole [which can also be called 2-{3-[4-Difluoromethoxy-3-(3R)-tetrahydrofuranyloxyphenyl]-pyrazol-1-yl}-N-(2,3-difluorophenyl)acetamide];

3-[3,4-Bis(difluoromethoxy)phenyl]-1-(N-(2,3-difluorophenyl)aminocarbonyl-methyl)pyrazole [which can also be called 2-{3-[3,4-Bis(difluoromethoxy)-phenyl]-pyrazol-1-yl}-N-(2,3-difluorophenyl)acetamide];

3-(4-Difluoromethoxy-3-(3R)-tetrahydrofuryloxyphenyl)-1-(N-(2-(6-methylpyridyl))aminocarbonylmethyl)pyrazole [which can be called 2-{3-[4-Difluoromethoxy-3-(3R)-tetrahydrofuranyloxyphenyl]-pyrazol-1-yl}-N-[2-(6-methylpyridyl)]acetamide];

1-(N-(2-Cyanophenyl)aminocarbonylmethyl)-3-(4-difluoromethoxy-3-(3R)-tetrahydrofuryloxyphenyl)pyrazole [which can also be called 1-N-(2-cyanophenyl)-2-{3-[4-difluoromethoxy-3-(3R)-tetrahydrofuranyloxyphenyl]-pyrazol-1-yl}acetamide];

3-(4-Difluoromethoxy-3-(3R)-tetrahydrofuryloxyphenyl)-1-(4-nitrobenzyl)pyrazole [which can also be called 3-[4-Difluoromethoxy-3-(3R)-tetrahydrofuranyloxyphenyl]-1-(4-nitrobenzyl)-1H-pyrazole];

3-(4-Difluoromethoxy-3-(3R)-tetrahydrofuryloxyphenyl)-1-(2-methylbenzyl)pyrazole [which can also be called 3-[4-Difluoromethoxy-3-(3R)-tetrahydrofuranyloxyphenyl]-1-(2-methylbenzyl)-1H-pyrazole];

1-(2,3-Difluorobenzyl)-3-(4-difluoromethoxy-3-(3R)-tetrahydrofuryloxyphenyl)pyrazole [which can also be called 1-(2,3-Difluorobenzyl)-3-[4-difluoromethoxy-3-(3R)-tetrahydrofuranyloxyphenyl]-1H-pyrazole];

3-(2-Acetyl-7-methoxybenzofuran-4-yl)pyrazole [which can also be called 3-(2-Acetyl-7-methoxybenzofuran-4-yl)-1H-pyrazole];

1-(4-Aminobenzyl)-3-(4-difluoromethoxy-3-(3R)-tetrahydrofuryloxyphenyl)pyrazole [which can also be called 1-(4-Aminobenzyl)-3-[4-difluoromethoxy-3-(3R)-tetrahydrofuranyloxyphenyl]-1H-pyrazole];

1-(2,3-Difluorobenzyl)-3-(4-methoxy-3-(3S)-tetrahydrofuryloxyphenyl)pyrazole [which can also be called 1-(2,3-Difluorobenzyl)-3-[4-methoxy-3-(3S)-tetrahydrofuranyloxyphenyl]-1H-pyrazole];

1-Cyclohexylmethyl-3-(4-methoxy-3-(3R)-tetrahydrofuryloxyphenyl)pyrazole [which can also be called 1-Cyclohexylmethyl-3-[4-methoxy-3-(3R)-tetrahydrofuranyloxyphenyl]-1H-pyrazole];

3-(4-Methoxy-3-(3R)-tetrahydrofuryloxyphenyl)-1-(3-phenpropyl)pyrazole [which can also be called 3-[4-Methoxy-3-(3R)-tetrahydrofuranyloxyphenyl]-1-(3-phenpropyl)-1H-pyrazole];

3-(4-Methoxy-3-(3R)-tetrahydrofuryloxyphenyl)-1-(4-pyridylmethyl)pyrazole [which can also be called 3-[4-Methoxy-3-(3R)-tetrahydrofuranyloxyphenyl]-1-(4-pyridylmethyl)-1H-pyrazole];

1-Ethylsulfonyl-3-(4-methoxy-3-(3R)-tetrahydrofuryloxyphenyl)pyrazole [which can also be called 1-Ethylsulfonyl-3-[4-methoxy-3-(3R)-tetrahydrofuranyloxyphenyl]-1H-pyrazole];

3-(4-Methoxy-3-(3R)-tetrahydrofuryloxyphenyl)-1-(1-propyl)pyrazole [which can also be called 3-[4-Methoxy-3-(3R)-tetrahydrofuranyloxyphenyl]-1-(1-propyl)-1H-pyrazole];

1-Benzylsulfonyl-3-(4-methoxy-3-(3R)-tetrahydrofuryloxyphenyl)pyrazole [which can also be called 1-Benzylsulfonyl-3-[4-methoxy-3-(3R)-tetrahydrofuranyloxyphenyl]-1H-pyrazole];

3-(4-Methoxy-3-(3R)-tetrahydrofuryloxyphenyl)-1-(2-pyridylmethyl)pyrazole [which can also be called 3-[4-Methoxy-3-(3R)-tetrahydrofuranyloxyphenyl]-1-(2-pyridylmethyl)-1H-pyrazole];

3-[(1-Cyclopentyl-3-ethylindazol)-6-yl]pyrazole [which can also be called 3-[(1-Cyclopentyl-3-ethylindazol)-6-yl]-1H-pyrazole];

3-(4-Methoxy-3-(3R)-tetrahydrofuryloxyphenyl)pyrazole-1-ylacetic acid [which can also be called 2-{3-[4-Methoxy-3-(3R)-tetrahydrofuranyloxyphenyl]-1H-pyrazol-1-yl}acetic acid];

3-(3-Benzyloxy-4-methoxyphenyl)pyrazole [which can also be called 3-(3-Benzyloxy-4-methoxyphenyl)-1H-pyrazole];

3-(4-Difluoromethoxy-3-(3R)-tetrahydrofuryloxyphenyl)pyrazole-1-ylacetic acid [which can also be called 2-{3-[4-Difluoromethoxy-3-(3R)-tetrahydrofuranyloxyphenyl]pyrazole-1-yl}acetic acid]

1-Cyclohexylmethyl-5-(4-methoxy-3-(3R)-tetrahydrofuryloxyphenyl)pyrazole [which can also be called 1-Cyclohexylmethyl-5-[4-methoxy-3-(3R)-tetrahydrofuranyloxyphenyl]-1H-pyrazole];

3-(3-Benzyloxy-4-methoxyphenyl)-1-(2,3-difluorobenzyl)pyrazole [which can also be called 3-(3-Benzyloxy-4-methoxyphenyl)-1-(2,3-difluorobenzyl)-1H-pyrazole];

3-(4-Methoxy-3-(3R)-tetrahydrofuryloxyphenyl)-1-[N-(1,2,3,4-tetrahydroisoquinolyl)carbonylmethyl]pyrazole [which can also be called 3-[4-Methoxy-3-(3R)-tetrahydrofuranyloxyphenyl]-1-[N-(1,2,3,4-tetrahydroisoquinolyl)carbonylmethyl]-1H-pyrazole];

1-[N-(7-Azaindolyl)carbonylmethyl]-3-(4-methoxy-3-(3R)-tetrahydrofuryloxyphenyl)pyrazole [which can also be called 1-[N-(7-Azaindolyl)carbonylmethyl]-3-[4-methoxy-3-(3R)-tetrahydrofuranyloxyphenyl]-1H-pyrazole];

3-(2-Acetyl-7-methoxybenzofuran-4-yl)-1-(2,3-difluorobenzyl)pyrazole [which can also be called 3-(2-Acetyl-7-methoxybenzofuran-4-yl)-1-(2,3-difluorobenzyl)-1H-pyrazole];

3-(2-Acetyl-7-methoxybenzofuran-4-yl)-1-(4-methylsulfonylbenzyl)pyrazole [which can also be called 3-(2-Acetyl-7-methoxybenzofuran-4-yl)-1-(4-methylsulfonylbenzyl)-1H-pyrazole];

1-(2,3-Difluorobenzyl)-3-[3-(2,3-difluorobenzyloxy)-4-methoxyphenyl]pyrazole [which can also be called 1-(2,3-Difluorobenzyl)-3-[3-(2,3-difluorobenzyloxy)-4-methoxyphenyl]-1H-pyrazole];

3-[3-(2,3-Difluorobenzyloxy)-4-methoxyphenyl]pyrazole [which can also be called 3-[3-(2,3-Difluorobenzyloxy)-4-methoxyphenyl]-1H-pyrazole];
1-(2,3-Difluorobenzyl)-3-(3-hydroxy-4-methoxyphenyl)pyrazole [which can also be called 1-(2,3-Difluorobenzyl)-3-(3-hydroxy-4-methoxyphenyl)-1H-pyrazole];
3-(2-Acetyl-7-methoxybenzofuran-4-yl)-1-(2-methylbenzyl)pyrazole [which can also be called 3-(2-Acetyl-7-methoxybenzofuran-4-yl)-1-(2-methylbenzyl)-1H-pyrazole];
3-(4-Methoxy-3-(3R)-tetrahydrofuryloxyphenyl)-1-(2-phenethyl)pyrazole [which can also be called 3-[4-Methoxy-3-(3R)-tetrahydrofuranyloxyphenyl]-1-(2-phenethyl)-1H-pyrazole];
1-(Acetophenone-2-yl)-3-(4-methoxy-3-(3R)-tetrahydrofuryloxyphenyl)pyrazole [which can also be called 2-{3-[4-methoxy-3-(3R)-tetrahydrofuranyloxyphenyl]-pyrazol-1-yl}-1-phenyl-1-ethanone];
1-Benzyl-3-(4-methoxy-3-(3R)-tetrahydrofuryloxyphenyl)pyrazole [which can also be called 1-Benzyl-3-[4-methoxy-3-(3R)-tetrahydrofuranyloxyphenyl]-1H-pyrazole];
1-Cyclopentyl-3-(4-methoxy-3-(3R)-tetrahydrofuryloxyphenyl)pyrazole [which can also be called 1-Cyclopentyl-3-[4-methoxy-3-(3R)-tetrahydrofuranyloxyphenyl]-1H-pyrazole];
3-[(1-Cyclopentyl-3-ethylindazol)-6-yl]-1-(2,3-difluorobenzyl)-1H-pyrazole;
3-[(1-Cyclopentyl-3-ethylindazol)-6-yl]-1-(4-carboxyphenyl)-1H-pyrazole;
3-[(1-Cyclopentyl-3-ethylindazol)-6-yl]-1-(4-methoxyphenyl)-1H-pyrazole;
3-[(1-Cyclopentyl-3-ethylindazol)-6-yl]-1-(2-methylbenzyl)pyrazole [which can also be called 3-[(1-Cyclopentyl-3-ethylindazol)-6-yl])-1-(2-methylbenzyl)-1H-pyrazole];
3-[(1-Cyclopentyl-3-ethylindazol)-6-yl]-1-(4-methylsulfonylbenzyl)pyrazole [which can also be called 3-[(1-Cyclopentyl-3-ethylindazol)-6-yl])-1-(4-methylsulfonylbenzyl)-1H-pyrazole];
3-[(1-Cyclopentyl-3-ethylindazol)-6-yl])-1-(2-pyridylmethyl)pyrazole [which can also be called 3-[(1-Cyclopentyl-3-ethylindazol)-6-yl])-1-(2-pyridylmethyl)-1H-pyrazole];
5-[(1-Cyclopentyl-3-ethylindazol)-6-yl])-1-(2-pyridylmethyl)-1H-pyrazole;
3-[4-Methoxy-3-(3R)-tetrahydrofuranyloxyphenyl]-1-[2-(6-methylpyridyl)-1H-pyrazole;
1-Cyclohexylmethyl-5-(4-methoxy-3-(3S)-tetrahydrofuryloxyphenyl)pyrazole [which can also be called 1-Cyclohexylmethyl-5-[4-methoxy-3-(3S)-tetrahydrofuranyloxyphenyl]-1H-pyrazole];
1-Cyclohexylmethyl-3-(4-methoxy-3-(3S)-tetrahydrofuryloxyphenyl)pyrazole [which can also be called 1-Cyclohexylmethyl-3-[4-methoxy-3-(3S)-tetrahydrofuranyloxyphenyl]-1H-pyrazole];
3-(3,4-Dimethoxyphenyl)-1-(tert-butyloxycarbonyl)pyrazole [which can also be called tert-Butyl [3-(3,4-Dimethoxyphenyl)-pyrazol-1-yl]carboxylate];
3-(4-Methoxy-3-(3R)-tetrahydrofuryloxyphenyl)-1-(methylsulfonylbenzyl)pyrazole [which can also be called 3-[4-Methoxy-3-(3R)-tetrahydrofuranyloxyphenyl]-1-(methylsulfonylbenzyl)-1H-pyrazole];
Isopropyl 2-{5-[4-methoxy-3-(3R)-tetrahydrofuranyloxyphenyl]-pyrazol-1-yl}acetate;
1-(2,3-Difluorobenzyl)-5-[4-methoxy-3-(3R)-tetrahydrofuranyl-oxyphenyl]-1H-pyrazole;
5-(3-Cyclopentyloxy-4-methoxyphenyl)-3-methyl-1-phenyl-1H-pyrazole;
1-Benzyl-5-[4-methoxy-3-(3R)-tetrahydrofuranyloxyphenyl]-3-trifluoromethyl-1H-pyrazole;
5-[4-Methoxy-3-(3R)-tetrahydrofuranyloxyphenyl]-1-(4-trifluoromethoxybenzyl)-1H-pyrazole;
5-[4-Methoxy-3-(3R)-tetrahydrofuranyloxyphenyl]-1-phenyl-3-trifluoromethyl-1H-pyrazole;
Ethyl[5-(4-methoxy-3-(3R)-tetrahydrofuranyloxyphenyl)-3-trifluoromethyl-1H-pyrazol-1-yl]acetate;
[5-(4-Methoxy-3-(3R)-tetrahydrofuranyloxyphenyl)-3-trifluoromethyl-1H-pyrazol-1-yl]acetic acid;
Isopropyl[5-(4-methoxy-3-(3R)-tetrahydrofuranyloxyphenyl)-3-trifluoromethyl-1H-pyrazol-1-yl]acetate;
1-(2,3-Difluorobenzyl)-5-(3,4-dimethoxyphenyl)-1H-pyrazole;
N-(3-Fluorophenyl)-2-{5-[4-methoxy-3-(3R)-tetrahydrofuranyloxyphenyl]-3-trifluoromethyl-pyrazol-1-yl}acetamide;
N-(5-Methylthiazol-2-yl)-2-{5-[4-methoxy-3-(3R)-tetrahydrofuranyloxyphenyl]-3-trifluoromethyl-pyrazol-1-yl}acetamide;
5-[4-Methoxy-3-(3R)-tetrahydrofuranyloxyphenyl]-1-(4-methylbenzyl)-1H-pyrazole;
1-(4-tert-Butylbenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-trifluoromethylbenzyl)-1H-pyrazole;
1-(3,4-Difluorobenzyl)-5-[4-methoxy-3-(3R)-tetrahydrofuranyloxyphenyl]-1H-pyrazole;
1-(2-Fluorobenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(3-nitrobenzyl)-1H-pyrazole;
5-[4-Methoxy-3-(3R)-tetrahydrofuranyloxyphenyl]-1-(4-methoxycarbonylbenzyl)-1H-pyrazole;
1-Benzyl-5-[4-methoxy-3-(3R)-tetrahydrofuranyloxyphenyl]-3-methyl-1H-pyrazole;
5-[4-Methoxy-3-(3R)-tetrahydrofuranyloxyphenyl]-3-methyl-1-phenyl-1H-pyrazole;
1-(3-Fluorobenzyl)-5-[4-methoxy-3-(3R)-tetrahydrofuranyloxyphenyl]-1H-pyrazole;
1-(3,5-Dimethoxybenzyl)-5-[4-methoxy-3-(3R)-tetrahydrofuranyloxyphenyl]-1H-pyrazole;
1-Cyclohexyl-5-[4-methoxy-3-(3R)-tetrahydrofuranyloxyphenyl]-3-methyl-1H-pyrazole;
1-(3-Fluorobenzyl)-5-[4-methoxy-3-(3R)-tetrahydrofuranyloxyphenyl]-3-trifluoromethyl-1H-pyrazole;
5-[4-Methoxy-3-(3R)-tetrahydrofuranyloxyphenyl]-1-phenyl-1H-pyrazole;
1-Cyclohexyl-5-[4-methoxy-3-(3R)-tetrahydrofuranyloxyphenyl]-1H-pyrazole;
Ethyl 1-Benzyl-5-[4-methoxy-3-(3R)-tetrahydrofuranyloxyphenyl]-1H-pyrazole-3-carboxylate;
1-Benzyl-5-[4-methoxy-3-(3R)-tetrahydrofuranyloxyphenyl]-1H-pyrazole;
1-(3-Methoxybenzyl)-5-[4-methoxy-3-(3R)-tetrahydrofuranyloxyphenyl]-1H-pyrazole;
1-(4-Fluorobenzyl)-5-[4-methoxy-3-(3R)-tetrahydrofuranyloxyphenyl]-1H-pyrazole;
1-(2-Methoxybenzyl)-5-[4-methoxy-3-(3R)-tetrahydrofuranyloxyphenyl]-3-methyl-1H-pyrazole;
1-(1-Butyl)-5-[4-methoxy-3-(3R)-tetrahydrofuranyloxyphenyl]-3-methyl-1H-pyrazole;
1-(2-Fluorophenyl)-5-[4-methoxy-3-(3R)-tetrahydrofuranyloxyphenyl]-3-methyl-1H-pyrazole;
1-(4-Chlorophenyl)-5-[4-methoxy-3-(3R)-tetrahydrofuranyloxyphenyl]-3-methyl-1H-pyrazole;

[5-(4-Methoxy-3-(3R)-tetrahydrofuranyloxyphenyl)-1H-pyrazol-1-yl]acetic acid;
N-Cyclopropyl-2-{5-[4-methoxy-3-(3R)-tetrahydrofuranyloxyphenyl]-pyrazol-1-yl}acetamide;
N-Isopropyl-2-{5-[4-methoxy-3-(3R)-tetrahydrofuranyloxyphenyl]-pyrazol-1-yl}acetamide;
3-Ethyl-5-[4-methoxy-3-(3R)-tetrahydrofuranyloxyphenyl]-1-(2-methoxybenzyl)-1H-pyrazole;
1-Cyclohexyl-3-ethyl-5-[4-methoxy-3-(3R)-tetrahydrofuranyloxyphenyl]-1H-pyrazole;
1-Benzyl-3-ethyl-5-[4-methoxy-3-(3R)-tetrahydrofuranyloxyphenyl]-1H-pyrazole;
Ethyl 3-ethyl-5-(4-methoxy-3-(3R)-tetrahydrofuranyloxyphenyl)-1H-pyrazol-1-yl]acetate;
5-[4-Methoxy-3-(3R)-tetrahydrofuranyloxyphenyl]-1-(4-methoxyphenyl)-1H-pyrazole;
5-[4-Methoxy-3-(3R)-tetrahydrofuranyloxyphenyl]-1-(2-phenylethyl)-1H-pyrazole;
1-Benzyl-5-[4-methoxy-3-(3R)-tetrahydrofuranyloxyphenyl]-1H-pyrazole-3-carboxylic acid;
1-(2,3-Dimethylphenyl)-3-ethyl-5-[4-methoxy-3-(3R)-tetrahydrofuranyloxyphenyl]-1H-pyrazole;
1-(4-Fluorophenyl)-5-[4-methoxy-3-(3R)-tetrahydrofuranyloxyphenyl]-1H-pyrazole;
1-(3,4-Dimethylphenyl)-3-ethyl-5-[4-methoxy-3-(3R)-tetrahydrofuranyloxyphenyl]-1H-pyrazole;
3-Ethyl-5-[4-methoxy-3-(3R)-tetrahydrofuranyloxyphenyl]-1-(2-methylphenyl)-1H-pyrazole;
1-(2-Benzothiazolyl)-5-[4-methoxy-3-(3R)-tetrahydrofuranyloxyphenyl]-3-methyl-1H-pyrazole;
1-(3,4-Dimethylphenyl)-5-[4-methoxy-3-(3R)-tetrahydrofuranyloxyphenyl]-3-methyl-1H-pyrazole;
2-{5-[4-Methoxy-3-(3R)-tetrahydrofuranyloxyphenyl]-pyrazol-1-yl}-N-phenylacetamide;
N,N-Diethyl-2-{5-[4-methoxy-3-(3R)-tetrahydrofuranyloxyphenyl]-pyrazol-1-yl}acetamide;
1-(2,3-Dimethylphenyl)-5-[4-methoxy-3-(3R)-tetrahydrofuranyloxyphenyl]-3-methyl-1H-pyrazole;
1-{1-Benzyl-5-[4-methoxy-3-(3R)-tetrahydrofuranyloxyphenyl]-1H-pyrazol-3-yl}ethanone;
2-{1-Benzyl-5-[4-methoxy-3-(3R)-tetrahydrofuranyloxyphenyl]-1H-pyrazol-3-yl}ethanone;
{1-Benzyl-5-[4-methoxy-3-(3R)-tetrahydrofuranyloxyphenyl]-1H-pyrazol-3-yl}methanone;
1-(4-Bromophenyl)-5-[4-methoxy-3-(3R)-tetrahydrofuranyloxyphenyl]-1H-pyrazole;
5-[4-Methoxy-3-(3R)-tetrahydrofuranyloxyphenyl]-3-methyl-1-(3-nitrophenyl)-1H-pyrazole;
5-[4-Methoxy-3-(3R)-tetrahydrofuranyloxyphenyl]-3-methyl-1-(2-methylphenyl)-1H-pyrazole;
1-(3,4-Difluorobenzyl)-5-(3-fluoro-4-methoxyphenyl)-1H-pyrazole;
5-(3-Fluoro-4-methoxyphenyl) 1-(4-methoxycarbonylbenzyl)-1H-pyrazole;
1-(2,6-Difluorobenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-trifluoromethoxyphenyl)-1H-pyrazole;
5-[4-Methoxy-3-(3R)-tetrahydrofuranyloxyphenyl]-1-(2-pyridyl)-1H-pyrazole;
1-(2-Benzothiazolyl)-5-[4-methoxy-3-(3R)-tetrahydrofuranyloxyphenyl]-1H-pyrazole;
1-(4-Fluorobenzyl)-5-(3-fluoro-4-methoxyphenyl)-1H-pyrazole;
5-[4-Methoxy-3-(3R)-tetrahydrofuranyloxyphenyl]-3-methyl-1-(2-phenylethyl)-1H-pyrazole;
5-[4-Methoxy-3-(3R)-tetrahydrofuranyloxyphenyl]-3-methyl-1-(4-trifluoromethoxyphenyl)-1H-pyrazole;
5-[4-Methoxy-3-(3R)-tetrahydrofuranyloxyphenyl]-3-methyl-1-(2-quinoxalinyl)-1H-pyrazole;
5-[4-Methoxy-3-(3R)-tetrahydrofuranyloxyphenyl]-1-[4-(4-morpholinyl)phenyl]-1H-pyrazole;
5-(3-Fluoro-4-methoxyphenyl)-1-(4-methoxyphenyl)-1H-pyrazole;
1-Benzyl-5-(3-fluoro-4-methoxyphenyl)-1H-pyrazole;
1-(2-Methoxyphenyl)-5-[4-methoxy-3-(3R)-tetrahydrofuranyloxyphenyl]-1H-pyrazole;
1-[2-(6-Fluoropyridyl)]-5-[4-methoxy-3-(3R)-tetrahydrofuranyloxyphenyl]-1H-pyrazole;
1-(4-Carboxybenzyl)-5-[4-methoxy-3-(3R)-tetrahydrofuranyloxyphenyl]-1H-pyrazole;
Ethyl 2-{5-[4-methoxy-3-(3R)-tetrahydrofuranyloxyphenyl]pyrazol-1-yl}acetate;
1-(2-Hydroxyethyl)-5-[4-methoxy-3-(3R)-tetrahydrofuranyloxyphenyl]-1H-pyrazole;
1-(2-Methoxyethyl)-5-[4-methoxy-3-(3R)-tetrahydrofuranyloxyphenyl]-1H-pyrazole;
1-(2-Cyclopropylmethoxyethyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-methoxyphenyl)-3-methyl-1H-pyrazole;
5-[4-Methoxy-3-(3R)-tetrahydrofuranyloxyphenyl]-1-(2-methoxycarbonyl-3-thienyl)-3-methyl-1H-pyrazole;
1-[2-(6-Fluoropyridyl)]-5-[4-methoxy-3-(3R)-tetrahydrofuranyloxyphenyl]-3-methyl-1 H-pyrazole;
5-[4-Methoxy-3-(3R)-tetrahydrofuranyloxyphenyl]-3-methyl-1-(2-pyridyl)-1H-pyrazole;
1-[2-(6-Chloropyridyl)]-5-[4-methoxy-3-(3R)-tetrahydrofuranyloxyphenyl]-3-methyl-1H-pyrazole;
1-(4-Carboxyphenyl)-5-[4-methoxy-3-(3R)-tetrahydrofuranyloxyphenyl]-1H-pyrazole;
1-(4-Carboxybenzyl)-5-(3-fluoro-4-methoxyphenyl)-1H-pyrazole;
5-(3,4-Dimethoxyphenyl)-1-(4-fluorobenzyl)-1H-pyrazole;
5-(3,4-Dimethoxyphenyl)-1-(4-methoxyphenyl)-1H-pyrazole;

and physiologically acceptable salts thereof, wherein in each case the compound can be in the form of a mixture of enantiomers such as the racemate or a mixture of diastereomers, or can be in the form of a single enantiomer or a single diastereomer.

According to a further method aspect of the invention, the compounds of formulas I, II, III, IV, V, and VI are selected from:

3-(3-Cyclopentyloxy-4-methoxyphenyl)pyrazole
3-(3-Cyclopentyloxy-4-methoxyphenyl)-1-(2-methylbenzyl)pyrazole
3-(3-Cyclopentyloxy-4-methoxyphenyl)-1-(2,3-difluorobenzyl)pyrazole
3-(3-Cyclopentyloxy-4-methoxyphenyl)-1-(4-nitrobenzyl)pyrazole
3-(4-Methoxy-3-(3R)-tetrahydrofuryloxyphenyl)-1-(2-methylbenzyl)pyrazole
1-(2,3-Difluorobenzyl)-3-(4-methoxy-3-(3R)-tetrahydrofuryloxyphenyl)pyrazole
1-(4-Aminobenzyl)-3-(3-cyclopentyloxy-4-methoxyphenyl)pyrazole
3-(4-Methoxy-3-(3R)-tetrahydrofuryloxyphenyl)pyrazole
3-(4-Methoxy-3-(3R)-tetrahydrofuryloxyphenyl)-1-(4-nitrobenzyl)pyrazole
1-(4-Aminobenzyl)-3-(4-methoxy-3-(3R)-tetrahydrofuryloxyphenyl)pyrazole 3-(4-Difluoromethoxy-3-(3R)-tetrahydrofuryloxyphenyl)-1-(N-(2-methylphenyl)aminocarbonylmethyl)pyrazole
3-[3,4-Bis(difluoromethoxy)phenyl]pyrazole
3-(4-Difluoromethoxy-3-(3R)-tetrahydrofuryloxyphenyl)pyrazole
3-(4-Difluoromethoxy-3-(3R)-tetrahydrofuryloxyphenyl)-1-(N-(2,3-difluorophenyl)aminocarbonylmethyl)pyrazole
3-[3,4-Bis(difluoromethoxy)phenyl]-1-(N-(2,3-difluorophenyl)aminocarbonylmethyl)pyrazole
3-(4-Difluoromethoxy-3-(3R)-tetrahydrofuryloxyphenyl)-1-(N-(2-(6-methylpyridyl))aminocarbonylmethyl)pyrazole
1-(N-(2-cyanophenyl)aminocarbonylmethyl)-3-(4-difluoromethoxy-3-(3R)-tetrahydrofuryloxyphenyl)pyrazole
3-(4-Difluoromethoxy-3-(3R)-tetrahydrofuryloxyphenyl)-1-(4-nitrobenzyl)pyrazole
3-(4-Difluoromethoxy-3-(3R)-tetrahydrofuryloxyphenyl)-1-(2-methylbenzyl)pyrazole
1-(2,3-Difluorobenzyl)-3-(4-difluoromethoxy-3-(3R)-tetrahydrofuryloxyphenyl)pyrazole
3-(2-Acetyl-7-methoxybenzofuran-4-yl)pyrazole
1-(4-Aminobenzyl)-3-(4-difluoromethoxy-3-(3R)-tetrahydrofuryloxyphenyl)pyrazole,
1-(2,3-Difluorobenzyl)-3-(4-methoxy-3-(3S)-tetrahydrofuryloxyphenyl)pyrazole,
1-Cyclohexylmethyl-3-(4-methoxy-3-(3R)-tetrahydrofuryloxyphenyl)pyrazole,
3-(4-Methoxy-3-(3R)-tetrahydrofuryloxyphenyl)-1-(3-phenpropyl)pyrazole,
3-(4-Methoxy-3-(3R)-tetrahydrofuryloxyphenyl)-1-(4-pyridylmethyl)pyrazole,
1-Ethylsulfonyl-3-(4-methoxy-3-(3R)-tetrahydrofuryloxyphenyl)pyrazole,
3-(4-Methoxy-3-(3R)-tetrahydrofuryloxyphenyl)-1-(1-propyl)pyrazole,
1-Benzylsulfonyl-3-(4-methoxy-3-(3R)-tetrahydrofuryloxyphenyl)pyrazole,
3-(4-Methoxy-3-(3R)-tetrahydrofuryloxyphenyl)-1-(2-pyridylmethyl)pyrazole,
3-[(1-Cyclopentyl-3-ethylindazole)-6-yl]pyrazole,
3-(4-Methoxy-3-(3R)-tetrahydrofuryloxyphenyl)pyrazole-1-ylacetic acid,
3-(3-Benzyloxy-4-methoxyphenyl)pyrazole,
3-(4-Difluoromethoxy-3-(3R)-tetrahydrofuryloxyphenyl)pyrazole-1-ylacetic acid,
1-Cyclohexylmethyl-5-(4-methoxy-3-(3R)-tetrahydrofuryloxyphenyl)pyrazole,
3-(3-Benzyloxy-4-methoxyphenyl)-1-(2,3-difluorobenzyl)pyrazole,
3-(4-Methoxy-3-(3R)-tetrahydrofuryloxyphenyl)-1-[N-(1,2,3,4-tetrahydroisoquinolyl)carbonylmethyl]pyrazole,
1-[N-(7-Azaindolyl)carbonylmethyl]-3-(4-methoxy-3-(3R)-tetrahydrofuryloxyphenyl)pyrazole,
3-(2-Acetyl-7-methoxybenzofuran-4-yl)-1-(2,3-difluorobenzyl)pyrazole,
3-(2-Acetyl-7-methoxybenzofuran-4-yl)-1-(4-methylsulfonylbenzyl)pyrazole,
1-(2,3-Difluorobenzyl)-3-[3-(2,3-difluorobenzyloxy)-4-methoxyphenyl]pyrazole,
3-[3-(2,3-Difluorobenzyloxy)-4-methoxyphenyl]pyrazole,
1-(2,3-Difluorobenzyl)-3-(3-hydroxy-4-methoxyphenyl)pyrazole,
3-(2-Acetyl-7-methoxybenzofuran-4-yl)-1-(2-methylbenzyl)pyrazole,
3-(4-Methoxy-3-(3R)-tetrahydrofuryloxyphenyl)-1-(2-phenethyl)pyrazole,
1-(Acetophenone-2-yl)-3-(4-methoxy-3-(3R)-tetrahydrofuryloxyphenyl)pyrazole,
1-Benzyl-3-(4-methoxy-3-(3R)-tetrahydrofuryloxyphenyl)pyrazole,
1-Cyclopentyl-3-(4-methoxy-3-(3R)-tetrahydrofuryloxyphenyl)pyrazole,
3-[(1-Cyclopentyl-3-ethylindazole)-6-yl]-1-(2,3-difluorophenyl)pyrazole,
3-[(1-Cyclopentyl-3-ethylindazole)-6-yl])-1-(2-methylbenzyl)pyrazole,
3-[(1-Cyclopentyl-3-ethylindazole)-6-yl])-1-(4-methylsulfonylbenzyl)pyrazole,
3-[(1-Cyclopentyl-3-ethylindazole)-6-yl])-1-(2-pyridylmethyl)pyrazole,
3-(4-Methoxy-3-(3R)-tetrahydrofuryloxyphenyl)-1-pyrazole,
1-Cyclohexylmethyl-5-(4-methoxy-3-(3S)-tetrahydrofuryloxyphenyl)pyrazole,
1-Cyclohexylmethyl-3-(4-methoxy-3-(3S)-tetrahydrofuryloxyphenyl)pyrazole,
3-(3,4-Dimethoxyphenyl)-1-(tert-butyloxycarbonyl)pyrazole,
3-(4-Methoxy-3-(3R)-tetrahydrofuryloxyphenyl)-1-(methylsulfonylbenzyl)pyrazole,
1-Isopropyloxycarbonylmethyl-5-(4-methoxy-3-(3R)-tetrahydrofuranylphenyl)pyrazole,
1-(2,3-Difluorobenzyl)-5-(4-methoxy-3-(3R)-tetrahydrofuranylphenyl)pyrazole, and physiologically acceptable salts thereof, wherein in each case the compound can be in the form of a mixture of enantiomers such as the racemate or a mixture of diastereomers, or can be in the form of a single enantiomer or a single diastereomer.

According to further method aspect of the invention, the compound of formulas I, II, III, IV, V, or VI is selected from:
3-(3-Cyclopentyloxy-4-methoxyphenyl)-1-(2,3-difluorobenzyl)pyrazole
1-(2,3-Difluorobenzyl)-3-(4-methoxy-3-(3R)-tetrahydrofuryloxyphenyl)pyrazole
1-(4-Aminobenzyl)-3-(3-cyclopentyloxy-4-methoxyphenyl)pyrazole
3-(4-Difluoromethoxy-3-(3R)-tetrahydrofuryloxyphenyl)-1-(N-(2,3-difluorophenyl)aminocarbonylmethyl)pyrazole
3-(4-Difluoromethoxy-3-(3R)-tetrahydrofuryloxyphenyl)-1-(N-(2-(6-methylpyridyl))aminocarbonylmethyl)pyrazole
1-(N-(2-cyanophenyl)aminocarbonylmethyl)-3-(4-difluoromethoxy-3-(3R)-tetrahydrofuryloxyphenyl)pyrazole
3-(4-Difluoromethoxy-3-(3R)-tetrahydrofuryloxyphenyl)-1-(4-nitrobenzyl)pyrazole
1-(2,3-Difluorobenzyl)-3-(4-difluoromethoxy-3-(3R)-tetrahydrofuryloxyphenyl)pyrazole
3-(2-Acetyl-7-methoxybenzofuran-4-yl)pyrazole,
3-[(1-Cyclopentyl-3-ethylindazole)-6-yl]pyrazole,
1-Cyclohexylmethyl-5-(4-methoxy-3-(3R)-tetrahydrofuryloxyphenyl)pyrazole,
3-(2-Acetyl-7-methoxybenzofuran-4-yl)-1-(4-methylsulfonylbenzyl)pyrazole,
3-[(1-Cyclopentyl-3-ethylindazole)-6-yl]-1-(2,3-difluorophenyl)pyrazole,
3-[(1-Cyclopentyl-3-ethylindazole)-6-yl])-1-(4-methylsulfonylbenzyl)pyrazole,
3-[(1-Cyclopentyl-3-ethylindazole)-6-yl])-1-(2-pyridylmethyl)pyrazole,
1-Isopropyloxycarbonylmethyl-5-(4-methoxy-3-(3R)-tetrahydrofuranylphenyl)pyrazole, 1-(2,3-Difluorobenzyl)-5-(4-methoxy-3-(3R)-tetrahydrofuranylphenyl)pyrazole, and physiologically acceptable salts thereof, wherein in each case the compound can be in the form of a mixture of enantiomers such as the racemate, or a mixture of diastereomers, or can be in the form of a single enantiomer or a single diastereomer.

Preferred aspects include pharmaceutical compositions comprising a compound of this invention and a pharmaceutically acceptable carrier and, optionally, another active agent as discussed below. A further preferred aspect includes a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating a psychiatric or neurological syndrome, e.g., depression and loss of memory, especially major depression and long-term memory, cognitive impairment or decline, memory impairment, etc.; a method of treating a disease state modulated by PDE4 activity, in a mammal, e.g., a human, e.g., those disease states mentioned herein.

Methods of the invention include, but are not limited to, methods of enhancing cognition in a patient in whom such enhancement is desired, methods of treating a patient suffering from cognition impairment or decline, methods of treating a patient having a disease involving decreased cAMP levels, methods of inhibiting PDE4 enzyme activity in a patient, methods of treating a patient suffering from memory impairment due to neurodegenerative disease, methods of treating a patient suffering from depression, methods of treating a patient suffering from an allergic or inflammatory disease. All methods comprise administering to the patient an effective amount of a compound of the invention. Preferably, the patient is human.

The compounds of the present invention may be prepared conventionally. Some of the known processes that can be used are described below. All starting materials are known or can be conventionally prepared from known starting materials.

Preparation of Starting Materials:

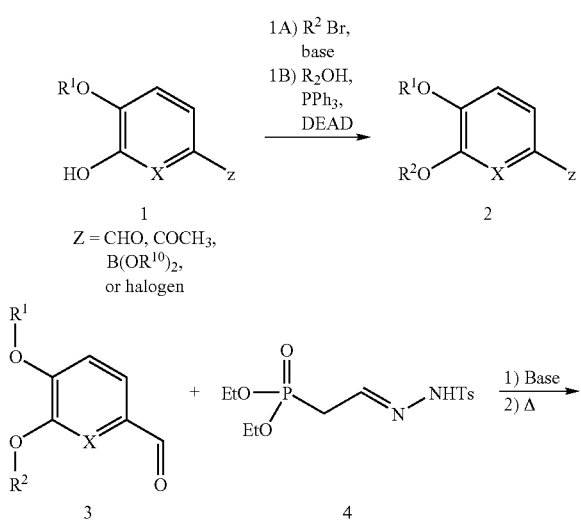

-continued

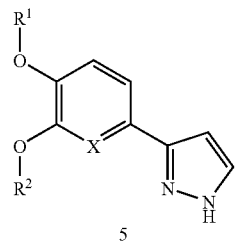

The starting materials for Formulas I and IV are prepared as shown in Scheme 1. Thus, appropriately substituted benzaldehydes 3(X=CH, N) are subjected to Horner-Wadsworth-Emmons conditions with phosphonate 2. The resulting olefin is not isolated, but heated to induce cyclization [Almirante, N.; Cerri, A.; Fedrizzi, G.; Marazzi, G.; Santagostino, M. Tetrahedron Lett. 1998, 39, 3287-3290] to provide the corresponding pyrazoles 5.

Alternatively, 3-substituted pyrazoles can be made from beta-ketoaldehydes and hydrazine [Murray, W.; Wachter, M.; Barton, D.; Forenro-Kelly, Y. Synthesis, 1991, 18] or from various palladium couplings using a pyrazole aptly substituted in the 3 position, for example with a bromine or a boron. [Cacchi, S.; Fabrizi, G.; Carnaio, A. Syn. Lett. 1997, 959-961].

Substitution on the pyrazole nitrogen is accomplished by treatment of the pyrazole 5 with an appropriate base such as NaH, LDA or $K_2CO_3$ in a polar aprotic solvent. This is followed by the addition of electrophile $R^3$-L-X', where X' is a suitable leaving group such as a halogen or sulfonate (Cl, Br, methanesulfonyl, etc.). A mixture of substituted pyrazoles 6a and 6b are obtained with the major isomer being the 1.3-disubstituted pyrazoles (6a). These isomers can be separated by HPLC.

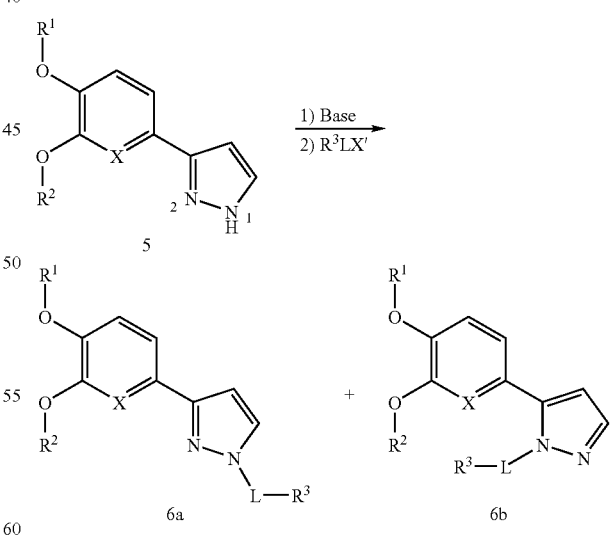

Reaction of pyrazole 5 with alkyl bromoacetate (preferably t-butyl bromoacetate) gives pyrazole substituted acetate esters. These esters are saponified to acetic acid derivatives 6a and 6b (L=$CH_2CO$, $R^3$=H) by treatment with either an acid, such as trifluoroacetic acid, or use of a base, such as sodium hydroxide. Treatment of the resultant acetic acid products with thionyl chloride or oxalyl chloride generates the corresponding acid chloride. Subsequent reaction with a nucleophile such as an amine (e.g., aniline) gives the acetamide derivatives 6a and 6b (e.g., L=CH$_2$CONH, R$^3$=phenyl). Similarly, the acetic acid derivative (L=CH$_2$CO$_2$, R$_3$=H) can be treated with HBTU or a suitable coupling reagent (i.e., DCC, HOBT, etc) and an amine compound to give the desired acetamide analogues 6a and 6b.

Alternatively, (Scheme 3) compounds of the type 6a where R$^2$=arylalkyl, alkyl, cycloalkyl, heteroalkyl, cycloalkylalkyl, heterocyclic or heterocyclic-alkyl groups can be prepared by either Mitsunobu reaction between phenol 7b and an appropriate alcohol (R$^2$OH) or alkylation with a suitable electrophile, R$^2$-X' (X' is a suitable leaving group such as a halogen or sulfonate (Cl, Br, methanesulfonyl etc.)), and an appropriate base (i.e., K$_2$CO$_3$, NaH, NaOH). (R$^2$=arylalkyl, alkyl, cycloalkyl, heteroalkyl, cycloalkylalkyl, heterocyclic and heterocyclic-alkyl groups.)

3-Aryloxy and 3-heteroaryloxy pyrazole derivatives of the type 6a (i.e., where R$^2$ is aryl or heteroaryl) are prepared by cross coupling reaction of phenol 7b with aryl boronic acids using a copper catalyst in the presence of an amine base. Suitable copper catalysts include copper diacetate, copper (II) chloride, etc. Generally, halogenated solvents are utilized, such as chloroform, dichloromethane, 1,2-dichloroethane, and the like. Commonly used bases include triethylamine, diisopropylethylamine, and pyrrolidine. Alternatively, 3-aryloxy and 3-heteroaryloxy pyrazole compounds can be synthesized in an analogous method as described previously for 3-phenyloxyrolipram, which utilizes an Ullman type coupling reaction starting with iodobenzene and 3-hydroxyrolipram [Schmiechen, R.; Horowski, R.; Palenschat, D.; Paschelke, G.; Wachtel, H.; Kehr, W., 4-(polyalkoxyphenyl)-2-pyrrolidones, U.S. Pat. No. 4,193,926, filed Mar. 18, 1980]. The other regioisomer 6b may be formed in an analogous manner.

Scheme 3

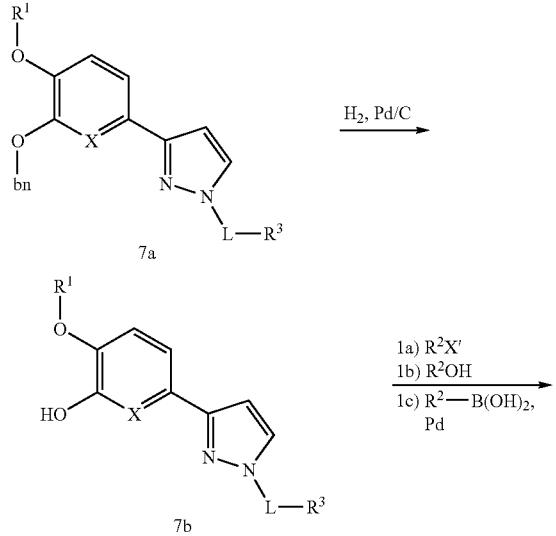

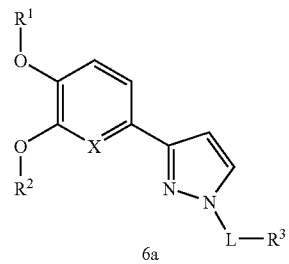

Compounds of Formulas II and V are synthesized in a similar manner starting from aldehyde 8. For these reactions, the ketone should be protected before pyrazole formation and can be deprotected afterwards. Suitable protecting groups include, but are not limited to, ketals and cyclic ketals.

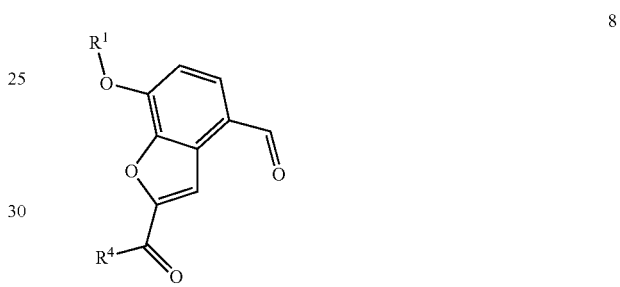

Compounds of Formulas III and VI are synthesized in a similar manner starting from aldehyde 9. [Marfat, A., et al., "Indazole Derivatives and Their Use as Inhibitors of Phosphodiesterase Type IV and the Production of Tumor Necrosis Factor TNF, U.S. Pat. No. 6,262,040.]

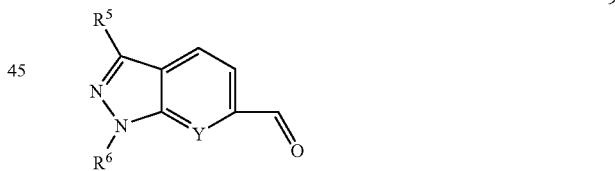

Synthesis of 1,5-pyrazoles
  A. Cross-Coupling Reactions

Alternatively, the 1,5-disubstituted compounds of Formula IV through VIA can be prepared from 1-hydroxypyrazole 10 (Scheme 4) (Eskildsen, J., Vedso, P., Begtrup, M., Synthesis, 2001, 1053-1056. Eskildsen, J., Kristensen, J., Vedso, P., Begtrup, M., J. Org. Chem, 2001, 66, 8654-8656. Paulson, A. S., Eskildsen J., Vedso, P., Begtrup, M., J. Org. Chem., 2002, 67, 3904-3907). Thus, warming a solution of 1-hydroxypyrazole 10 with an electrophile such as a benzyl bromide or α-bromoacetate in CHCl$_3$ to 60 to 100° C. provides 2-substituted-pyrazol-1-oxides 11. Subsequent treatment with POCl$_3$ or POBr$_3$ in a halogenated solvent such as CHCl$_3$ yields 5-halo-1-substituted pyrazoles 12. Such 5-halo-1-substituted pyrazoles can undergo cross-coupling type reaction with aryl boronic acids 2 (z=B(OH)$_2$) or can be metalated (e.g., halogen-magnesium exchange, transmetalation with $ZnCl_2$) for a Negishi-type reaction with an aryl halide 2 (Z=halogen).

Scheme 4

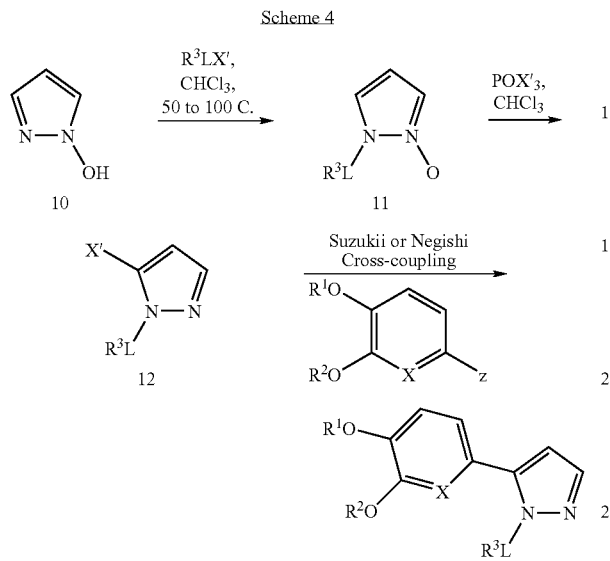

Alternatively, 1,5-disubstituted pyrazoles 6b can be prepared from 2-aryldithianes 13 in a three step synthesis. Thus, dithiane intermediate 13 can be prepared by reaction of aldehyde 3 with propane dithiol and a Lewis acid catalyst such as $BF_3$—$Et_2O$ in an aprotic solvent (Hatch, R. P., Shringarpure, J., Weinreb, S. M., J. Org. Chem., 1978, 43, 4172-4177). Subsequent reaction of the alkyl lithium produced dithiane anion with appropriately substituted epoxides provides 2,2-disubstituted dithianes 14. Oxidation of alcohol 14 to the protected β-keto dithiane followed by treatment with an appropriately substituted hydrazine salt provides 1,5-disubstitued pyrazoles 6b.

Scheme 5

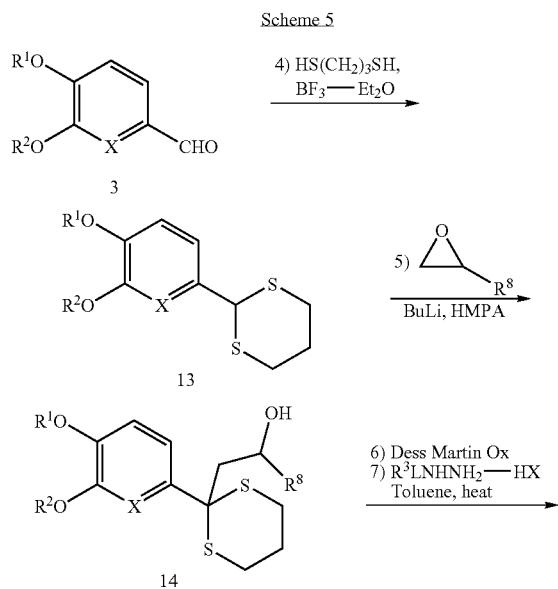

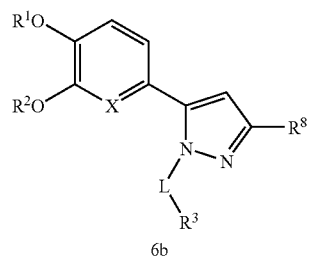

Another method to prepare 1,5-disubstituted pyrazoles of type 6b is through condensation reaction between 1,3-diketo derivative 16 and a substituted hydrazine (Reference: Nakamura, Toshio, et al., *J. Med Chem*, 2003, 46, 5416; Penning, T. D., et al, *J. Med. Chem.*, 1997, 40, 1347-1365.) The selectivity of this reaction for 1,5 versus 1,3-disubstituted pyrazoles varies pending the substitution at $R^8$. Formation of the 1,5-disubstituted pyrazoles are favored when $R^8$ is an electron withdrawing group such as carboxylate or trifluoromethyl, or a small group such as hydrogen. Starting 1,3-diketo derivatives 16 are prepared from acetophenone derivatives 15 by reaction with sodium hydride and an appropriately substituted ethyl acetate.

Scheme 6

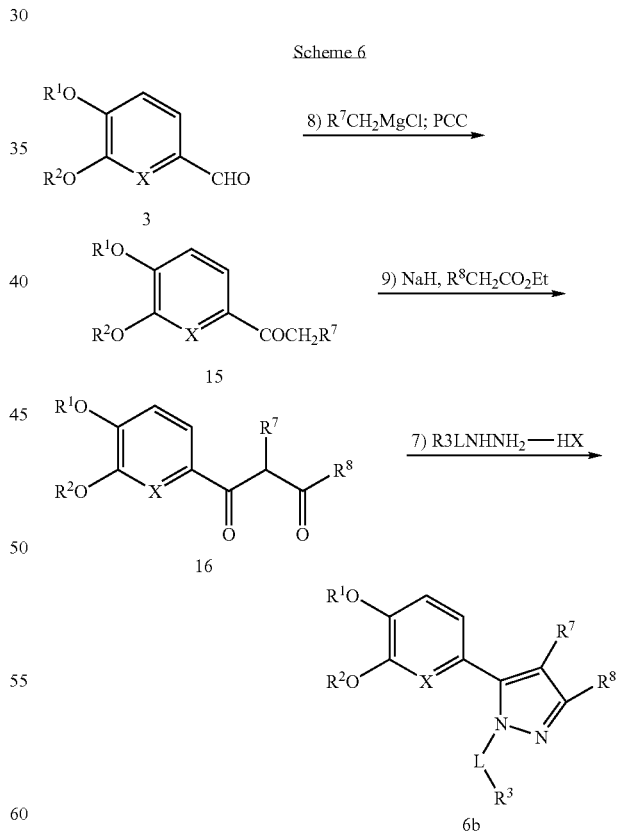

In a similar fashion, enamines of the type 17 undergo reaction with appropriately substituted hydrazines to provide target pyrazoles 6b. (Reference Yang, Ji, et al., *J. Med. Chem.* 2004, 47(6), 1547)

Scheme 7

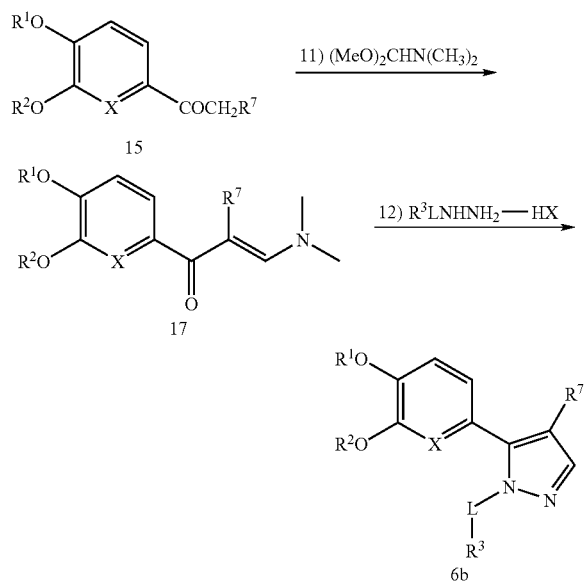

Compounds of Formula VIII can also be prepared using the general procedure described above.

One of ordinary skill in the art will recognize that some of the compounds of Formulas I, II, III, IV, V, VI, VIA and VIII can exist in different geometrical isomeric forms. In addition, some of the compounds of the present invention possess one or more asymmetric atoms and are thus capable of existing in the form of optical isomers, as well as in the form of racemic or nonracemic mixtures thereof, and in the form of diastereomers and diastereomeric mixtures inter alia. For example, in the 3-tetrahydrofuranyl structure ($R^2$), the carbon atom at the 3-ring position will be chiral. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereomeric salts using an optically active acid or base or formation of covalent diastereomers.

Examples of appropriate acids are tartaric, diacetyltartaric, dibenzoyltartaric, ditoluoyltartaric and camphorsulfonic acid. Mixtures of diastereomers can be separated into their individual diastereomers on the basis of their physical and/or chemical differences by methods known to those skilled in the art, for example, by chromatography or fractional crystallization. The optically active bases or acids are then liberated from the separated diastereomeric salts.

A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I-VIII can likewise be obtained by utilizing optically active starting materials in chiral syntheses processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The Synthesis of Radiolabeled Compounds via Organometallic Intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

The present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of one or more compounds of Formulas I, II, III, IV, V, VI, VIA or VIII containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of selective PDE4 inhibition, the compounds of the present invention can be administered to anyone requiring PDE4 inhibition. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, ampakines NMDA-R modulators, mGluR modulators, and cholinesterase inhibitors (e.g., donepezil, rivastigimine, and galanthamine). In such combinations, each active ingredient can be administered either in accordance with their usual dosage range or a dose below their usual dosage range.

The present invention further includes methods of treatment that involve inhibition of PDE4 enzymes. Thus, the present invention includes methods of selective inhibition of PDE4 enzymes in animals, e.g., mammals, especially humans, wherein such inhibition has a therapeutic effect, such as where such inhibition may relieve conditions involving neurological syndromes, such as the loss of memory, especially long-term memory. Such methods comprise administering to an animal in need thereof, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (Alzheimer's, Parkinson's disease, Pick's disease), vascular (Infarcts, Hemorrhage, Cardiac Disorders), mixed vascular and Alzheimer's, bacterial meningitis, Creutzfeld-Jacob Disease, and multiple sclerosis), traumatic (subdural hematoma or traumatic brain injury), infectious (HIV), toxic (heavy metals, alcohol, medications), metabolic (Vitamin $B_{12}$ or folate deficiency), CNS hypoxia, Cushing's disease, psychiatric (depression and schizophrenia) and hydrocephalus.

The present invention also includes methods for treating memory loss separate from dementias, including mild cognitive impairment (MCI) and age-related cognitive decline. The present invention includes methods of treatment for memory impairment as a result of disease including Huntington's disease and Down's syndrome. According to another aspect, the invention includes methods for treating memory loss from anesthetics, chemotherapy, radiation treatment, post-surgical trauma, post-traumatic stress disorder (PTSD), obesity, and diabetes.

The compounds of the invention can also be used to treat schizophrenia, bipolar or manic depression, major depression, and drug addiction. PDE4 inhibitors can be used to raise cAMP levels and prevent neurons from undergoing apoptosis. PDE4 inhibitors are also known to be anti-inflammatory. The combination of preventing neuronal apoptosis and inhibiting inflammatory responses make these compounds useful to treat neurodegeneration resulting from any disease or injury, including stroke, Alzheimer's disease, multiple sclerosis, amyolaterosclerosis (ALS), and multiple systems atrophy (MSA), as well as spinal injury.

PDE4 inhibitors have been shown to produce antidepressant effects in humans and antidepressant-like effects in animal models of depression. Clinical studies in humans suffering from major depression have demonstrated efficacy of the PDE4 inhibitor, rolipram, with comparable results in some of these studies to those of desipramine [Bobon D, Breulet M, Gerard-Vandenhove M A, Guito-Goffioul F, Plomteux G, Satre-Hemandez M, Schratzer M, Troisfontaines B, von Frenckell R, Wachtel H (1988) Is Phosphodiesterase Inhibition a New Mechanism of Antidepressant Action? Eur Arch Psychiatr Neurol Sci. 238:2-6; Meya U, Wachtel H, Sastre-Hemandez M (1991) Inhibition of Phosphodiesterase as an Antidepressive Mechanism: Clinical Properties of Rolipram. In Ansseau M, von Frenckell, Franck G (eds) Biological Markers of Depression: State of the art. Elsevier Science Publishers B.V., Pp. 209-213; Zhu J, Mix E, Winblad B (2001) The Antidepressant and Anti-inflammatory Effects of Rolipram in the Central Nervous System. CNS Drug Reviews 7:387-398]. Rolipram was active in a number of biochemical and behavioral preclinical models of antidepressant activity [Wachtel H (1983) Potential Antidepressant Activity of Rolipram and other Selective Cyclic Adenosine 3',5'-Monophosphate Phosphodiesterase Inhibitors. Neuropharmacology 22: 267-272; and Wachtel H., Schneider HH (1986) Rolipram, a novel antidepressant drug, reverses the hypothermia and hypokinesia of monoamine-depleted mice by an action beyond postsynaptic monoamine receptors. Neuropharmacology 25:1119-1126]. More recently, studies with rolipram have demonstrated efficacy of this compound in the tail suspension and forced swimming models of antidepressant activity; these effects were eliminated in animals transgenically modified to lack the PDE4D subtype suggesting that the antidepressant effects of rolipram are mediated by its inhibition of the PDE4 enzyme, specifically the PDE4D subtype [Zhang H-T, Huang Y, Jin S-L, Frith S A, Suvarna N, Conti M, O'Donnell J M (2002) Antidepressant-like Profile and Reduced Sensitivity to Rolipram in Mice Deficient in the PDE4D Phosphodiesterase Enzyme. Neuropsychopharmacology 27:587-595].

Thus, in accordance with a preferred embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I, II, III, IV, V, VI, VIA or VIII or a pharmaceutically acceptable salt thereof.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amunt of a compound according to Formulas I, II, III, IV, V, VI, VIA or VIII or a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, emphysema, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia greata, hypertrophic scars, discoid lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases, osteoporosis, and the like. The compounds can also be used in a method of treating patients suffering from disease states characterized by decreased NMDA function, such as schizophrenia. The compounds may also be used for neuronal regeneration. The compounds can also be used to treat psychosis characterized by elevated levels of PDE4, for example, various forms of depression, such as manic depression, major depression, and depression associated with psychiatric and neurological disorders. The compounds may additionally be used for neurogenesis.

The use of trisubstituted phenyl derivatives for treating asthma, chronic bronchitis, psoriasis, allergic rhinitis, and other inflammatory diseases, and for inhibiting tumor necrosis factor is known within the art. See, e.g., WO 98/58901, JP 11-189577, JP 10-072415, WO 93/25517, WO 94/14742, U.S. Pat. No. 5,814,651, and U.S. Pat. No. 5,935,978. These references describe 1,3,4-trisubstituted phenyl compounds said to exhibit PDE4 inhibition activity. They also describe assays for determining PDE4 inhibition activity, and methods for synthesizing such compounds. The entire disclosures of these documents are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury ($R^1$), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The invention is also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins are: dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 also called Machado-Joseph disease, MJD (ataxin-3); spinocerebellar ataxia type-6 (alpha 1a-voltage dependent calcium channel); spinocerebellar ataxia type-7 (ataxin-7); and spinal and bulbar muscular atrophy, SBMA, also known as Kennedy disease (androgen receptor).

Thus, in accordance with a further aspect of the invention, there is provided a method of treating a polyglutamine-repeat disease or CAG repeat expansion disease comprising administering to a patient, especially a human, a therapeutically effective amount of a compound according to Formulas I-VIII. In accordance with a further embodiment, there is provided a method of treating Huntington's disease (HD), dentatorubral-pallidoluysian atrophy (DRPLA), spinocerebellar ataxia type-1, spinocerebellar ataxia type-2, spinocerebellar ataxia type-3 (Machado-Joseph disease), spinocerebellar ataxia type-6, spinocerebellar ataxia type-7, or spinal and bulbar muscular atrophy, comprising administering to a patient, especially a human, a therapeutically effective amount of a compound according to Formulas I-VIII.

The compounds of the present invention can be administered as the sole active agent or in combination with other pharmaceutical agents such as other agents used in the treatment of cognitive impairment and/or in the treatment of psychosis, e.g., other PDE4 inhibitors, calcium channel blockers, choinergic drugs, adenosine receptor modulators, amphakines NMDA-R modulators, mGluR modulators, and cholinesterase inhibitors (e.g., donepezil, rivastigimine, and galanthamine). In such combinations, each active ingredient can be administered either in accordance with their usual dosage range or a dose below their usual dosage range.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of generally 0.001-100 mg/kg/day, for example, 0.01-100 mg/kg/day, preferably 0.1-70 mg/kg/day, especially 0.5-10 mg/kg/day. Unit dosage forms can contain generally 0.01-1000 mg of active compound, for example, 0.1-50 mg of active compound. For intravenous administration, the compounds can be administered, in single or multiple dosages, at a dosage level of, for example, 0.001-50 mg/kg/day, preferably 0.001-10 mg/kg/day, especially 0.01-1 mg/kg/day. Unit dosage forms can contain, for example, 0.1-10 mg of active compound.

In carrying out the procedures of the present invention, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. Provisional Application Ser. No. 60/463,725, filed Apr. 18, 2003, are hereby incorporated by reference in their entirety.

EXAMPLES

Example 1

Example 1A

Synthesis of 4-Methoxy-3-(3R)-tetrahydrofuryloxybenzaldehyde

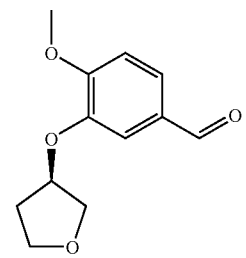

3-Hydroxy-4-methoxybenzaldehyde (7.6 g; 50 mmol) was dissolved in THF (200 mL) followed by addition of (S)-3-hydroxytetrahydrofuran (6.0 mL; 75 mmol) and triphenylphosphine (19.7 g; 75 mmol). The resulting solution was cooled to 5° C. and diisopropyl azodicarboxylate (14.8 mL; 75 mmol) was added dropwise over 10 minutes. The clear orange solution was stirred at ambient temperature for 16 hours. Thin layer chromatography analysis using a 1:1 mixture of hexane/ethyl acetate determined the reaction to be complete. The solvent was removed under reduced pressure and the residue was taken in ethyl acetate (60 mL) and extracted twice with 20% aqueous sodium bisulfite (150 mL/extraction). The extracts were pooled and washed with ethyl acetate (75 mL). The aqueous layer was basified with solid sodium hydroxide (26 g) and then extracted with 3×150 mL of ethyl acetate (150 mL/extraction). The organic extracts were pooled, washed with 40 mL of brine, dried (Na$_2$SO$_4$), and concentrated to afford 7.4 g (66%) of a pale yellow oil. $^1$H NMR (CDCl$_3$; 300 MHz) δ 2.2-2.4 (m, 2H); 3.8-4.1 (m, 7H); 5.0 (m, 1H); 7.0 (d, 1H); 7.4 (s, 1H); 7.5 (d, 1H); 9.9 (s, 1H). ES-MS [M+H]+=223.2

The following compounds were prepared in a similar fashion with different starting materials:

1-Bromo-4-methoxy-3-(3R)-tetrahydrofuranyloxybenzene.
4-Methoxy-3-(3S)-tetrahydrofuryloxybenzaldehyde.

Example 1B

Synthesis of 3-[4-Methoxy-3-(3R)-tetrahydrofuranyloxyphenyl]-1H-pyrazole

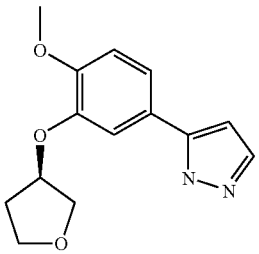

Sodium hydride (60% in mineral oil, 1.51 g, 37.7 mmol) was suspended in THF (20 mL) and cooled to 5° C. followed by addition of diethoxyphosphorylacetaldehyde tosylhydrazone (6.51 g, 18.7 mmol) in THF (20 mL) over 10 minutes. After stirring for 30 minutes at 5° C., the yellow suspension was treated with a solution of 4-methoxy-3-(3R)-tetrahydrofuryloxybenzaldehyde (2.84 g, 12.8 mmol) in THF (20 mL) and stirred for 1 hour at room temperature and 16 hours at 80° C. in an oil bath. After cooling to room temperature, the reaction was poured into 5% aqueous $NaH_2PO_4$ and extracted with ethyl acetate. The extract was washed with water and brine, dried over $Na_2SO_4$ and concentrated to afford a yellow solid. Recrystallization from ethyl acetate furnished 1.9 g (57%) of 3-[4-Methoxy-3-(3R)-tetrahydrofuranyloxyphenyl]-1H-pyrazole in two crops as light yellow solids. (mp 149-151° C.); $^1$H NMR ($CDCl_3$, 300 MHz) δ 2.23 (m, 2H), 3.85-4.10 (m, 4H), 3.89 (s, 3H), 5.02 (m, 1H), 6.54 (m, 1H), 6.92 (m, 1H), 7.25 (m, 2H), 7.60 (m, 1H); MS [M+H]=261.

The following compounds were prepared in a similar fashion with different starting materials:
A. 3-(3,4-Dimethoxyphenyl)-1H-pyrazole
B. 3-(3-Cyclopentyloxy-4-methoxyphenyl)-1H-pyrazole
C. 3-[3,4-Bis(difluoromethoxy)phenyl]-1H-pyrazole
D. 3-[4-Difluoromethoxy-3-(3R)-tetrahydrofuranyloxyphenyl]-1H-pyrazole
E. 3-(3-Benzyloxy-4-methoxyphenyl)pyrazole
F. 3-[3-(2,3-Difluorobenzyloxy)-4-methoxyphenyl]pyrazole

Example 2

Synthesis of 1-(2,3-difluorobenzyl)-3-[4-methoxy-3-(3R)-tetrahydrofuranyloxyphenyl]-1H-pyrazole

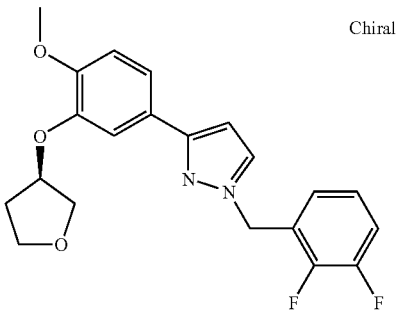

3-[4-Methoxy-3-(3R)tetrahydrofuranyloxyphenyl]-1H-pyrazole (243 mg, 0.96 mmol) was dissolved in DMF (8 mL) at room temperature and treated with sodium hydride (75 mg, 1.86 mmol) with stirring for 3 hours. The reaction mixture was treated with a solution of 2,3-difluorobenzyl bromide (0.35 mL, 2.79 mmol) in DMF (1 mL) and stirred at room temperature for 16 hours. The reaction was diluted with ethyl acetate and washed with water three times and brine once. The organic layer was dried over sodium sulfate and concentrated to an oil which was purified on a column of silica gel using a hexane/ethyl acetate gradient. Tubes containing the compound were pooled and evaporated under vacuum to afford 327 mg (90%) of 1-(2,3-difluorobenzyl)-3-[4-methoxy-3-(3R)-tetrahydrofuranyloxyphenyl]-1H-pyrazole as a colorless oil. MS [M+H]=387; $^1$H NMR ($CDCl_3$, 300 MHz) δ 2.23 (m, 2H), 3.8-4.1 (m, 4H), 3.92 (s, 3H), 5.1 (m, 1H), 5.4 (s, 2H), 6.5 (s, 1H), 6.9 (m, 2H), 6.95-7.11 (m, 2H), 7.3 (m, 2H), 7.45 (s, 1H). A minor product consisting of 1-(2,3-difluorobenzyl)-5-[4-methoxy-3-(3R)-tetrahydrofuranyloxyphenyl]-1H-pyrazole was also formed, which can be separated and isolated by preparative HPLC (see, e.g., Example 3).

The following compounds were prepared in a similar fashion with different starting materials (in some cases, the 5-regioisomer was also formed and could be separated by methods known in the art such as preparative HPLC):
A. 3-(3-Cyclopentyloxy-4-methoxyphenyl)-1-(2-methylbenzyl)-1H-pyrazole
B. 3-(3-Cyclopentyloxy-4-methoxyphenyl)-1-(2,3-difluorobenzyl)-1H-pyrazole
C. 3-(3-Cyclopentyloxy-4-methoxyphenyl)-1-(4-nitrobenzyl)-1H-pyrazole
D. 3-[4-Methoxy-3-(3R)-tetrahydrofuranyloxyphenyl]-1-(2-methylbenzyl)-1H-pyrazole
E. 1-(4-Aminobenzyl)-3-(3-cyclopentyloxy-4-methoxyphenyl)-1H-pyrazole
F. 3-[4-Methoxy-3-(3R)-tetrahydrofuranyloxyphenyl]-1-(4-nitrobenzyl)-1H-pyrazole
G. 1-(4-Aminobenzyl)-3-[4-methoxy-3-(3R)-tetrahydrofuranyloxyphenyl]-1H-pyrazole
H. 3-[4-Difluoromethoxy-3-(3R)-tetrahydrofuranyloxyphenyl]-1-(4-nitrobenzyl)-1H-pyrazole
I. 3-[4-Difluoromethoxy-3-(3R)-tetrahydrofuranyloxyphenyl]-1-(2-methylbenzyl)-1H-pyrazole
J. 1-(2,3-Difluorobenzyl)-3-[4-difluoromethoxy-3-(3R)-tetrahydrofuranyloxyphenyl]-1H-pyrazole
K. 1-(4-Aminobenzyl)-3-[4-difluoromethoxy-3-(3R)-tetrahydrofuranyloxyphenyl]-1H-pyrazole
L. 1-(2,3-Difluorobenzyl)-3-[4-methoxy-3-(3S)-tetrahydrofuranyloxyphenyl]-1H-pyrazole
M. 1-Cyclohexylmethyl-3-[4-methoxy-3-(3R)-tetrahydrofuranyloxyphenyl]-1H-pyrazole
N. 3-[4-Methoxy-3-(3R)-tetrahydrofuranyloxyphenyl]-1-(3-phenpropyl)-1H-pyrazole
O. 3-[4-Methoxy-3-(3R)-tetrahydrofuranyloxyphenyl]-1-(4-pyridylmethyl)-1H-pyrazole
P. 1-Ethylsulfonyl-3-[4-methoxy-3-(3R)-tetrahydrofuranyloxyphenyl]-1H-pyrazole
Q. 3-[4-Methoxy-3-(3R)-tetrahydrofuranyloxyphenyl]-1-(1-propyl)-1H-pyrazole
R. 1-Benzylsulfonyl-3-[4-Methoxy-3-(3R)-tetrahydrofuranyloxyphenyl]-1H-pyrazole
S. 3-[4-Methoxy-3-(3R)-tetrahydrofuranyloxyphenyl]-1-(2-pyridylmethyl)-1H-pyrazole
T. 3-(3-Benzyloxy-4-methoxyphenyl)-1-(2,3-difluorobenzyl)-1H-pyrazole
U. 3-[4-Methoxy-3-(3R)-tetrahydrofuranyloxyphenyl]-1-[N-(1,2,3,4-tetrahydroisoquinolyl)carbonylmethyl]-1H-pyrazole
V. 1-[N-(7-Azaindolyl)carbonylmethyl]-3-[4-Methoxy-3-(3R)-tetrahydrofuranyloxyphenyl]-1H-pyrazole
W. 1-(2,3-Difluorobenzyl)-3-[3-(2,3-difluorobenzyloxy)-4-methoxyphenyl]-1H-pyrazole X. 1-(2,3-Difluorobenzyl)-3-(3-hydroxy-4-methoxyphenyl)-1H-pyrazole
Y. 3-[4-Methoxy-3-(3R)-tetrahydrofuranyloxyphenyl]-1-(2-phenethyl)-1H-pyrazole
Z. 2-{3-[4-methoxy-3-(3R)-tetrahydrofuranyloxyphenyl]-pyrazol-1-yl}-1-phenyl-1-ethanone]
AA. 1-Benzyl-3-[4-Methoxy-3-(3R)-tetrahydrofuranyloxyphenyl]-1H-pyrazole
AB. 1-Cyclopentyl-3-[4-Methoxy-3-(3R)-tetrahydrofuranyloxyphenyl]-1H-pyrazole
AC. 3-[4-Methoxy-3-(3R)-tetrahydrofuranyloxyphenyl]-1-[2-(6-methylpyridyl)]-1H-pyrazole
AD. 1-Cyclohexylmethyl-3-(4-methoxy-3-(3S)-tetrahydrofuranyloxyphenyl)-1H-pyrazole
AE. 3-[4-Methoxy-3-(3R)-tetrahydrofuranyloxyphenyl]-1-(methylsulfonylbenzyl)-1H-pyrazole
AF. 3-(2-Acetyl-7-methoxybenzofuran-4-yl)-1-(2,3-difluorobenzyl)-1H-pyrazole
AGF. 3-(2-Acetyl-7-methoxybenzofuran-4-yl)-1-(4-methylsulfonylbenzyl)-1H-pyrazole
AH. 3-(2-Acetyl-7-methoxybenzofuran-4-yl)-1-(2-methylbenzyl)-1H-pyrazole
AI. 1-(2-Methoxyethyl)-5-[4-methoxy-3-(3R)-tetrahydrofuranyloxyphenyl]-1H-pyrazole
AJ. 1-(2-Cyclopropylmethoxyethyl)-5-[4-methoxy-3-(3R)-tetrahydrofuranyloxyphenyl]-1H-pyrazole Example 3

1-Cyclohexylmethyl-3-[4-methoxy-3-(3R)-tetrahydrofuranyloxyphenyl]-1H-pyrazole

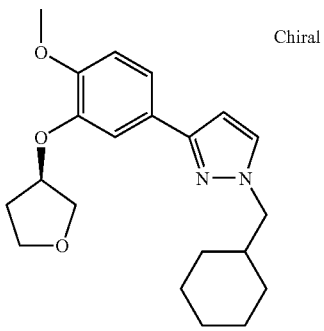

and 1-Cyclohexylmethyl-5-[4-methoxy-3-(3R)-tetrahydrofuranyloxyphenyl]-1H-pyrazole

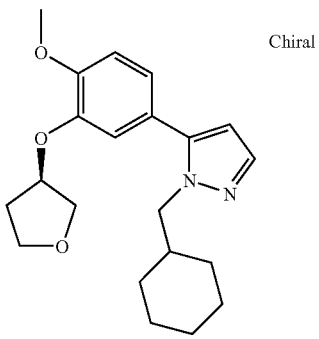

A solution of 3-[4-methoxy-3-(3R)-tetrahydrofuranyloxyphenyl]-1H-pyrazole (78 mg, 0.3 mmol) in DMF (2 mL) was treated with sodium hydride (60% in oil, 24 mg, 0.6 mmol) and stirred at room temperature for three hours. The reaction mixture was then treated with a solution of (bromomethyl)cyclohexane (0.13 mL, 0.9 mmol) in DMF (0.8 mL) and stirred at ambient temperature for 16 hours. The mixture was diluted with ethyl acetate (60 mL) and washed with water (2×20 mL) and brine (1×15 mL), dried ($Na_2SO_4$) and concentrated to 250 mg of an oil, which was chromatographed over silica gel using a 10-30% ethyl acetate/hexane gradient. Concentration of fractions afforded 92 mg of an oil consisting of a mixture of regioisomers in a ratio of 3.5:1 as deteremined by LCMS. The mixture of regioisomers was taken in 1 mL of acetonitrile/water (3:2 with 0.1% formic acid) and resolved by preparative hplc using a Waters C18, 5 um, 30×100 mm column with a flow rate of 45 mL/min. A gradient of 35-80% acetonitrile/water containing 0.1% formic acid over 6 minutes was employed and a Waters 2996 PDA detector was utilized to trigger collection at 248 nm. Baseline resolution was achieved with peak A eluting at 7.61 min and peak B eluting at 8.15 min. Tubes containing each regioisomer were concentrated on a Genevac HT4 Series II Evaporator supplying 14 mg of (peak A; retention time=7.61 minutes) 1-cyclohexylmethyl-5-[4-methoxy-3-(3R)-tetrahydrofuranyloxyphenyl]-1H-pyrazole and 54 mg of (peak B; retention time=8.15 minutes) 1-cyclohexylmethyl-3-[4-methoxy-3-(3R)-tetrahydrofuranyloxyphenyl]-1H-pyrazole, each as colorless oils. Both peaks exhibit [M+H]=357. $^1$H NMR for peak A (CDCl$_3$, 300 MHz) δ 0.80 (m, 2H), 1.1-1.3 (m, 3H), 1.4-1.7 (m, 5H), 1.9 (m, 1H), 2.2 (m, 2H), 3.8-4.2 (m, 9H), 4.97 (s, 1H), 6.22 (s, 1H), 6.82 (s, 1H), 6.96 (s, 2H), 7.55 (s, 1H).

$^1$H NMR of peak B (CDCl$_3$, 300 MHz) δ 0.80 (m, 2H), 1.1-1.3 (m, 3H), 1.4-1.7 (m, 5H), 1.9 (m, 1H), 2.2 (m, 2H), 3.8-4.2 (m, 9H), 5.08 (s, 1H), 6.44 (s, 1H), 6.9 (d, 1H), 7.35 (m, 3H).

The following compounds were prepared in a similar fashion with different starting materials:

A. 1-Cyclohexylmethyl-5-[4-methoxy-3-(3S)-tetrahydrofuranyloxyphenyl]-1H-pyrazole
B. Isopropyl 2-{5-[4-methoxy-3-(3R)-tetrahydrofuranylphenyl]-pyrazol-1-yl}acetate
C. 1-(2,3-Difluorobenzyl)-5-[4-methoxy-3-(3R)-tetrahydrofuranylphenyl]-1H-pyrazole Example 4

Intermediate B: Synthesis of 2-Acetyl-4-bromo-7-methoxybenzofuran

2-Acetyl-7-methoxybenzofuran (1.0 g, 5.3 mmol) was dissolved in glacial acetic acid (29 mL) followed by addition of sodium acetate (1.3 g, 15.8 mmol). The reaction was treated dropwise with a solution of bromine (0.26 mL, 5.26 mmol) in glacial acetic acid (10 mL) at room temperature followed by stirring for one hour. The solvent was removed under vacuum. The residue was dissolved in water and extracted three times with dichloromethane. The combined organic extracts were washed with 2% aqueous sodium bicarbonate, dried over sodium sulfate and concentrated under vacuum. The residue was purified on silica gel using a 50-100% dichloromethane/hexane gradient affording the product as a white solid. (1.00 g, 75%). $^1$H NMR (CDCl$_3$, 300 MHz) δ 7.44 (s, 1H), 7.32 (d, 1H), 6.80 (d, 1H), 4.0 (s, 3H), 2.62 (s, 3H).

Intermediate C: Synthesis of 4-bromo-7-methoxy-2-[2-methyl-(1,3-dioxolan)-2-yl]benzofuran A solution of 2-acetyl-4-bromo-7-methoxybenzofuran (0.50 g, 1.86 mmol), 5 mL of ethylene glycol, and PPTS (46 mg, 0.186 mmol) was refluxed overnight in benzene (37 mL) using a Dean Stark apparatus. The reaction was cooled to room temperature, washed with aqueous sodium bicarbonate, dried over sodium sulfate and evaporated under vacuum to afford 293 mg (50%) of 4-bromo-7-methoxy-2-[2-methyl-(1,3-dioxolan)-2-yl]benzofuran as an oil. $^1$H NMR (CDCl$_3$, 300 MHz) δ 7.28 (d, 1H), 6.74 (s, 1H), 6.69 (d, 1H), 4.04 (m, 4H), 1.84 (s, 3H).

Intermediate D: Synthesis of 7-methoxy-2-[2-methyl-(1,3-dioxolan)-2-yl]-benzofuran-4-carboxaldehyde 4-Bromo-7-methoxy-2-[2-methyl-(1,3-dioxolan)-2-yl]benzofuran (666 mg, 2.1 mmol) was dissolved in THF (21 mL), cooled to −60° C. under an argon atmosphere, and t-butyl lithium (2.6 mL, 1.7 M) was added with stirring at −60° C. The mixture was stirred at −60° C. for one hour, DMF (0.82 mL, 10.6 mmol) in THF (20 mL) was added, and the reaction was stirred at ambient temperature overnight. The reaction was poured into aqueous sodium bicarbonate and extracted three times with ethyl acetate. The combined extracts were washed once with water, once with brine, and dried over sodium sulfate. Evaporation of the solvent under reduced pressure followed by purification on silica gel using a 10-50% ethyl acetate/hexane gradient afforded 7-methoxy-2-[2-methyl-(1,3-dioxolan)-2-yl]-benzofuran-4-carboxaldehyde (399 mg; 72%) as an oil. $^1$H NMR (CDCl$_3$, 300 MHz) δ 10.01 (s, 1H), 7.66 (d, 1H), 7.45 (s, 1H), 6.88 (d, 1H), 4.08 (m, 7H), 1.84 (s, 3H).

Example 5

Synthesis of 3-(2-Acetyl-7-methoxybenzofuran-4-yl)pyrazole

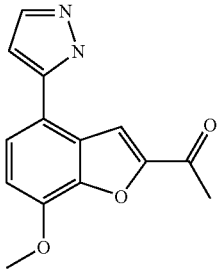

A suspension of sodium hydride (60% in oil, 174 mg, 4.36 mmol) in THF (5 mL) was cooled to 0° C. under argon, and then treated with a solution of diethoxyphosphorylacetaldehyde tosylhydrazone (759 mg, 2.2 mmol) in THF (7 mL). After stirring at 0° C. for 30 minutes a solution of 7-methoxy-2-(2-methyl-[1,3]dioxolan-2-yl)benzofuran-4-carboxaldehyde (381 mg, 1.45 mmol) in THF (5 mL) was added and the reaction stirred at room temperature overnight followed by stirring at 65° C. for 5 hours. After cooling to room temperature, the reaction was poured into 5% aqueous NaH$_2$PO$_4$ and extracted with ethyl acetate. The extract was washed with water, washed with brine, dried over Na$_2$SO$_4$, and concentrated. The residue was chromatographed on silica gel using a 25-50% ethyl acetate/hexane gradient to afford the dioxolane protected pyrazole (306 mg, 70%). The masked ketone (306 mg) was taken in 3M HCl in THF (10 mL) and stirred at room temperature for 2 hours. The solution was neutralized with sodium bicarbonate and extracted with ethyl acetate three times. The combined extracts were washed with water, washed with brine, dried over sodium sulfate and concentrated under vacuum. The residue was purified on silica gel using hexane/ethyl acetate (1:1; v/v) to isolate 3-(2-Acetyl-7-methoxybenzofuran-4-yl)pyrazole (192 mg, 74%) as a yellow solid.
$^1$H NMR (CDCl$_3$, 300 MHz) δ 8.09 (s, 1H), 7.70 (d, 1H), 7.53 (d, 1H), 6.98 (d, 1H), 6.70 (d, 1H), 4.07 (s, 3H), 2.65 (s, 3H).

Example 6

Intermediate E: Synthesis of 4-difluoromethoxy-3-hydroxybenzaldehyde 3,4-Dihydroxybenzaldehyde (20 g, 145 mmol), chlorodifluoroacetic acid sodium salt (55.19 g, 362 mmol) and sodium hydroxide (5.50 g, 138 mmol) were stirred in DMF (1200 mL) at 55° C. under nitrogen for 16 hours. The pH was adjusted to 1.0 by the addition of 10% aqueous HCl followed by extraction with ethyl acetate (3×500 mL). The combined extracts were evaporated under vacuum. The residue was purified on silica gel using a 10-20% ethyl acetate/hexane gradient. 4-difluoromethoxy-3-hydroxybenzaldehyde was isolated in 24% yield (6.62 g). $^1$H NMR (CDCl$_3$, 400 MHz) δ 6.1 (br s, 1H), 6.48-6.85 (t, 1H OCHF$_2$), 7.26 (d, 1H), 7.44 (d, 1H), 7.55 (s, 1H), 9.91 (s, 1H).

Intermediate F: Synthesis of tert-Butyl 2-{3-[4-difluoromethoxy-3-(3R)-tetrahydrofuranyloxyphenyl]pyrazol-1-yl}acetate 3-[4-Difluoromethoxy-3-(3R)-tetrahydrofuranyloxyphenyl]-1H-pyrazole (199 mg, 0.67 mmol) was dissolved in DMF (9 mL). Sodium hydride (60% in oil, 54 mg, 1.34 mmol) was added at room temperature and stirred for 1 hour followed by addition of tert-butyl bromoacetate (0.30 mL, 2.01 mmol) in DMF (1 mL). The reaction was stirred for 16 hours at room temperature, diluted with ethyl acetate, and washed with water twice and brine once. The solvent was dried over sodium sulfate and concentrated to 500 mg of a pale yellow oil, which was purified on silica gel using a 20-50% ethyl acetate/hexane gradient to afford tert-butyl 2-{3-[4-difluoromethoxy-3-(3R)-tetrahydrofuranyloxyphenyl]pyrazol-1-yl}acetate as a colorless oil (145 mg, 53%). MS [M+H]=411. $^1$H NMR (DMSO 300 MHz) δ 1.42 (s, 9H), 2.05 (m, 1H), 2.23 (m, 1H), 3.8-4.0 (m, 4H), 4.98 (s, 2H), 5.18 (br s, 1H), 6.78-7.28 (t, 1H OCHF$_2$), 6.80 (s, 1H), 7.21 (d, 1H), 7.38 (d, 1H), 7.45 (s, 1H), 7.77 (s, 1H).

Synthesis of 2-{3-[4-difluoromethoxy-3-(3R)-tetrahydrofuranyloxyphenyl]pyrazole-1-yl}acetic acid

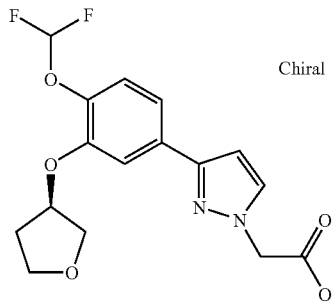

tert-Butyl 2-{3-[4-difluoromethoxy-3-(3R)-tetrahydrofuranyloxyphenyl]pyrazol-1-yl}acetate (762 mg, 1.85 mmol) was stirred in dichloromethane (11 mL) and treated with trifluoroacetic acid (11 mL) with stirring for 90 minutes. The solvent was removed under reduced pressure and partitioned between ethyl acetate/water. The organic layer was washed with water three times and brine once. After drying over sodium sulfate, the solvent was stripped to furnish 2-{3-[4-difluoromethoxy-3-(tetrahydrofuryloxy)phenyl] pyrazole-1-yl}acetic acid as a semisolid (657 mg, 100%) MS [M+H]=355. $^1$H NMR (CDCl$_3$ 300 MHz) δ 2.25 (m, 2H), 4.02 (m, 4H), 5.07 (m, 2H), 5.2 (br s, 1H), 6.31-6.81 (t, 1H OCHF$_2$), 6.61 (s, 1H), 7.19-7.28 (m, 3H), 7.29 (s, 1H), 7.52 (s, 1H).

2-{3-(4-Methoxy-3-(3R)-tetrahydrofuranyloxyphenyl)pyrazole-1-yl}acetic acid was synthesized in a similar manner with different starting materials.

Example 7

Synthesis of 2-{3-[4-Difluoromethoxy-3-(3R)-tetrahydrofuranyloxyphenyl]-pyrazol-1-yl}-N-(2,3-difluorophenyl)acetamide

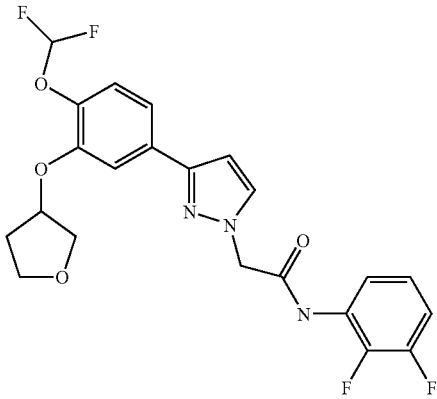

2-{3-[4-difluoromethoxy-3-(3R)-tetrahydrofuranyloxyphenyl]pyrazol-1-yl}acetic acid (84 mg, 0.23 mmol) was dissolved in dichloromethane (2 mL), cooled to 5° C. and treated the oxalyl chloride (2M in dichloromethane, 0.13 mL, 0.26 mmol) and stirred for 90 minutes. In a separate flask, 2,3-difluoroaniline (0.35 mL, 0.35 mmol) in THF (2 mL) was treated with sodium hydride (60% in oil, 22 mg, 0.56 mmol) and stirred for 90 minutes. The solvent from the initial flask was removed under reduced pressure. The residue was taken in THF (2 mL), cooled to 5° C. and treated with the difluoroaniline/hydride suspension followed by stirring at ambient temperature for 16 hours. The solvent was removed under vacuum and the residue was partitioned between ethyl acetate/water. The organic layer was washed with water and brine, dried over sodium sulfate and evaporated to afford 57 mg of a brown oil. This was adsorbed onto a preparative thin layer chromatography silica gel plate (20×20 cm, 2000 micron) using ethyl acetate/hexane (1:1 v/v) to elute. The product was isolated from the plate by scraping and suspending the silica gel in ethyl acetate following by filtering through a bed of Celite. Evaporation of the solvent afforded 2-{3-[4-difluoromethoxy-3-(3R)-tetrahydrofuranyloxyphenyl]-pyrazol-1-yl}-N-(2,3-difluorophenyl)acetamide as a white foam (15 mg, 14%) MS [M+H]=446; $^1$H NMR (CDCl$_3$, 300 MHz) δ 2.28 (m, 2H), 4.05 (m, 4H), 4.98 (s, 2H). 5.1 (s, 1H), 6.3-6.7 (t, 1H OCHF$_2$) 6.65 (s, 1H), 6.8 (m, 1H), 6.9 (m, 1H), 7.25 (m, 2H), 7.56 (s, 2H) 8.3 (t, 1H), 9.8 (s, 1H).

The following compounds were prepared in a similar fashion with different starting materials:

A. 2-{3-[3,4-Bis(difluoromethoxy)-phenyl]-pyrazol-1-yl}-N-(2-methylphenyl)acetamide]
B. 2-{3-[3,4-Bis(difluoromethoxy)-phenyl]-pyrazol-1-yl}-N-(2,3-difluorophenyl)acetamide
C. 1-N-(2-cyanophenyl)-2-{3-[4-difluoromethoxy-3-(3R)-tetrahydrofuranyloxyphenyl]-pyrazol-1-yl}acetamide
D. 2-{3-[4-Difluoromethoxy-3-(3R)-tetrahydrofuranyloxyphenyl]-pyrazol-1-yl}-N-[2-(6-methylpyridyl)]acetamide]

Example 8

Intermediate G: Methyl 3-ethyl-1H-indazol-6-yl-carboxylate

To a solution of 1.35 g (7.1 mmol) of 3-ethyl-1H-indazol-6-yl-carboxylic acid, [Marfat, A., et al., "Indazole Derivatives and Their Use as Inhibitors of Phosphodiesterase Type IV and the Production of Tumor Necrosis Factor TNF, U.S. Pat. No. 6,262,040], 2.9 mL (71 mmol) of methanol, and 0.95 g (7.8 mmol) of DMAP in 60 mL of CH$_2$Cl$_2$ was added 1.5 g (7.8 mmol) of EDCl—nHCl. This mixture was stirred at room temperature overnight, concentrated and the residue dissolved in 50 mL of ethyl acetate. The organic layer was successively washed with 40 mL of 1N HCl, 40 mL of water and 40 mL of brine, dried (Na$_2$SO$_4$), and concentrated. The residue was purified by chromatography over silica gel using a gradient of 35% to 50% ethyl acetate in hexanes over 20 minutes as eluant to yield 860 mg (4.2 mmol) of methyl 3-ethyl-1H-indazol-6-yl-carboxylate. $^1$H-NMR (CDCl$_3$) δ 11.7 (s, 1H), 8.18 (s, 1H), 7.73 (apparent q, 9.0 Hz, 2H), 3.94 (s, 3H), 3.03 (q, 7.5 Hz, 2H), 1.42 (t, 7.5 Hz, 3H).

Intermediate H: Methyl 1-Cyclopentyl-3-ethyl-1H-indazol-6-yl-carboxylate

To a flask containing 337 mg (8.4 mmol) of NaH (60% in mineral oil), 1.7 mL (8.4 mmol) of 15-crown-5 and 42 mL of DMF was added 860 mg (4.2 mmol) of methyl 3-ethyl-1H-indazol-6-yl-carboxylate. This mixture was stirred at room temperature for 3 hours and then 1.35 mL (12.6 mmol) of cyclopentyl bromide was added and the reaction was stirred at room temperature overnight. The solvent was removed and the residue was dissolved in 40 mL ethyl acetate, washed with 30 mL of water and 30 mL of brine, dried (Na$_2$SO$_4$), and concentrated. The residue was purified by column chromatography over SiO$_2$ using a step gradient of 10% ethyl acetate in hexanes until the first compound eluted and then 50% ethyl acetate in hexanes to provide 662 mg (2.4 mmol) of methyl 1-cyclopentyl-3-ethyl-1H-indazol-6-yl-carboxylate as a clear oil along with 144 mg (0.53 mmol) methyl 2-(cyclopentyl-3-ethyl)-2H-indazol-6-yl-carboxylate as a yellow oil. $^1$H-NMR (CDCl$_3$) δ 8.17 (s, 1H), 7.71 (dd, J1=8.4 Hz, J2=6.7 Hz, 2H), 5.0 (p, J=7.5 Hz, 1H), 3.97 (s, 3H), 3.00 (q, J=7.5 Hz, 2H), 2.16 (m, 4H), 1.92 (m, 2H), 1.74 (m, 2H), 1.39 (t, J=7.6 Hz, 3H).

Intermediate I: 1-Cyclopentyl-3-ethyl-6-hydroxymethyl-1H-indazole

DIBAL (10 mL, 1M in toluene) was slowly added with stirring at −50° C. to a solution of 886 mg (3.25 mmol) of methyl 1-cyclopentyl-3-ethyl-1H-indazol-6-yl-carboxylate in 32 mL of CH$_2$Cl$_2$. The reaction stirred at −50° C. for 1 hour and was quenched by the slow addition of 4 mL of MeOH and then, with stirring, poured into a saturated Rochelle's salt and ethyl acetate mixture (60 ml each). Stirring continued at room temperature until both layers were clear. The organic layer was separated and the aqueous layer was extracted with 3×40 mL of ethyl acetate. The organic fractions were combined, dried (Na$_2$SO$_4$), and concentrated. The compound was purified via column chromatography over SiO$_2$ using a 1:4 solution of EtOAc in hexanes as eluant to yield 427 mg (1.75 mmol) of 1-cyclopentyl-3-ethyl-6-hydroxymethanol-1H-indazole as a clear oil. ¹H-NMR (CDCl₃) δ 7.66 (d, J=8.2 Hz, 1H), 7.42 (s, 1H), 7.07 (d, J=8.2 Hz), 4.92 (p, J=7.7 Hz, 1H), 4.84 (d, J=5.5 Hz, 2H), 2.99 (q, J=7.6 Hz, 2H), 2.15 (m, 4H), 2.04 (m, 2H), 1.73 (m, 2H), 1.38 (t, J=7.6 Hz, 3H).

Intermediate J: 1-Cyclopentyl-3-ethyl-1H-indazol-6-yl-carboxaldehyde

To a solution of 427 mg (1.75 mmol) 1-cyclopentyl-3-ethyl-6-hydroxymethanol-1H-indazole in 58 mL of CHCl₃ was added 2.1 g (24.1 mmol) of MnO₂. The reaction was stirred at room temperature for 6 hours, the solids were removed by filtration and the filtrate was concentrated. The residue was purified via column chromatography over SiO₂ using 3% ethyl acetate in hexanes as eluant to give 332 mg (1.37 mmol) of 1-cyclopentyl-3-ethyl-1H-indazol-6-yl-carboxaldehyde as a clear oil. ¹H-NMR (CDCl₃) δ 10.13 (s, 1H), 7.94 (s, 1H), 7.78 (d, J=8.2 Hz, 1H), 7.61 (d, J=8.2 Hz, 1H), 5.02 (p, J=7.4 Hz, 1H), 3.02 (q, J=7.5 Hz, 2H), 2.19 (m, 4H), 2.02 (m, 2H), 1.76 (m, 2H), 1.40 (t, J=7.5 Hz, 3H).

3-[(1-Cyclopentyl-3-ethylindazol)-6-yl]-1H-pyrazole

A flask containing 165 mg (4.12 mmol) of NaH (60% in mineral oil) and 4 mL of THF was placed under Ar and cooled to 0° C. A solution of 716 mg (2.06 mmol) of diethoxyphosphorylacetaldehyde tosylhydrazone in 7 mL of THF was added over 5 minutes. The reaction stirred at 0° C. for 30 minutes followed by the addition of a solution of 332 mg (1.37 mmol) of 1-cyclopentyl-3-ethyl-1H-indazol-6-yl-carboxaldehyde in 4.5 mL THF. The ice bath was removed and the solution was stirred at room temperature for 4 hours, and then heated to 65° C. overnight. The reaction mixture was cooled to room temperature, poured into 50 mL of 5% NaH₂PO₄ and extracted with 3×25 mL of ethyl acetate. The organic layers were combined, dried over Na₂SO₄, concentrated, and purified by column chromatography over SiO₂ using a gradient from 10% to 50% ethyl acetate in hexanes over 20 minutes to yield 185 mg (0.66 mmol) of 1-cyclopentyl-3-ethyl-6-(1H-pyrazol-3-yl)-1H-indazole as a white foam. ¹H-NMR (CDCl₃) δ 7.80 (s, 1H), 7.69 (d, J=8.3 Hz, 1H), 7.65 (s, 1H), 7.5 (d, J=8.3 Hz, 1H), 6.7 (s, 1H) 4.90 (p, J=7.5 Hz, 1H), 3.00 (q, J=7.5 Hz, 2H), 2.13 (m, 4H), 2.00 (m, 2H), 1.71 (m, 2H), 1.40 (t, J=7.5, 3H).

Example 9

3-[(1-Cyclopentyl-3-ethylindazol)-6-yl]-1-(2,3-difluorobenzyl)-1H-pyrazole

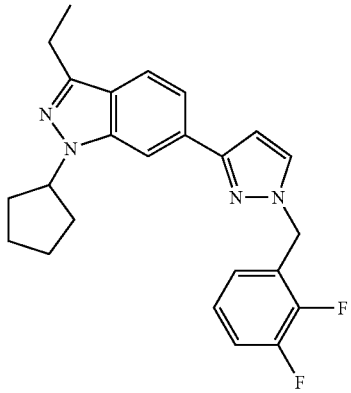

A solution of 31.8 mg (0.11 mmol) of 3-[(1-cyclopentyl-3-ethylindazol)-6-yl]-1H-pyrazole in 1 mL of DMF was added to a flask containing 12.9 mg (0.32 mmol) of NaH (60% in mineral oil) and 1 mL of DMF. This was stirred at room temperature for 3 hours. Then, a solution of 43 μL (0.33 mmol) of 2,3-difluorobenzyl bromide in 1 mL of DMF was added and the reaction was stirred at room temperature overnight. The mixture was poured into a mixture of 10 mL of water and 10 mL of ethyl acetate. The organic layer was washed with 2×10 mL of water and 1×10 mL of brine. The organic layer was then dried over Na₂SO₄, filtered and the solvent was removed under reduced pressure. Purification via column chromatography over 4 g of silica using 5% ethyl acetate in hexanes to 10% ethyl acetate in hexanes gradient over 10 minutes to give 24 mg (0.06 mmol, 52% yield) of 3-[(1-cyclopentyl-3-ethylindazol)-6-yl]-1-(2,3-difluorobenzyl)-1H-pyrazole as a clear oil. ¹H-NMR (CDCl₃) δ 7.84 (s, 1H), 7.69 (d, J=8.3 Hz, 1H), 7.54 (d, J=8.3 Hz, 1H), 7.50 (s, 1H), 7.15-7.04 (m, 3H), 6.68 (s, 1H), 5.48 (s, 2H), 4.99 (p, J=7.6 Hz, 1H), 3.01 (q, J=7.4 Hz, 2H), 2.12 (s, 4H), 1.98 (s, 2H), 1.75-1.72 (m, 2H), 1.40 (t, 7.4 Hz, 3H).

The following compounds were synthesized in a similar manner with different starting materials:

A. 3-[(1-Cyclopentyl-3-ethylindazol)-6-yl]-1-(2,3-difluorophenyl)-1H-pyrazole

B. 3-[(1-Cyclopentyl-3-ethylindazol)-6-yl])-1-(2-methylbenzyl)-1H-pyrazole

C. 3-[(1-Cyclopentyl-3-ethylindazol)-6-yl])-1-(4-methylsulfonylbenzyl)-1H-pyrazole D. 3-[(1-Cyclopentyl-3-ethylindazol)-6-yl])-1-(2-pyridylmethyl)-1H-pyrazole Example 10

Synthesis of 2-[4-Methoxy-3-(3R)-tetrahydrofuranyloxyphenyl]-1,3-dithiane

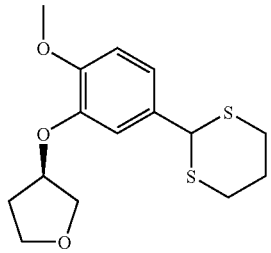

4-Methoxy-3-(3R)-tetrahydrofuranyloxybenzaldehyde (8.37 g; 37.6 mmol) was dissolved in dichloromethane (120 mL) followed by addition of 1,3-propanedithiol (11.3 mL; 113 mmol) and boron trifluoride etherate (0.6 mL). The reaction mixture became mildly exothermic and turbid. Reaction monitoring by LC-MS showed complete conversion taking place in 90 minutes. The reaction was washed with 30 mL of water and 30 mL of brine, dried over anhydrous sodium sulfate and concentrated. Trituration of the residue with ether produced a white solid that was collected by filtration and dried yielding 9.09 g (77%) of 2-[4-methoxy-3-(3R)-tetrahydrofuranyloxyphenyl]-1,3-dithiane.

¹H NMR (CDCl₃; 300 MHz) δ 1.85-2.25 (m, 4H); 2.85-2.95 (m, 2H); 3.0-3.1 (m, 2H); 3.85 (s, 3H); 3.9-4.1 (m, 4H); 4.95-5.00 (m, 1H); 5.1 (s, 1H); 6.85 (d, 1H); 7.00 (d, 1H); 7.05 (d, 1H). ES-MS [M+H]+=313.2

Example 11

Synthesis of 2-{2-[4-Methoxy-3-(3R)-tetrahydro-furanyloxyphenyl]-1,3-dithian-2-yl}propanol

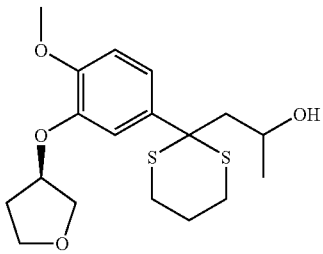

Solid 2-[4-methoxy-3-(3R)-tetrahydrofuranyloxyphenyl]-1,3-dithiane (2.5 g; 8 mmol) was added to an oven-dried flask equipped with a stir bar, septum and an inert gas line. Dry tetrahydrofuran (40 mL) was added and stirred at −40° C. using an acetonitrile/dry ice bath. To the resulting solution was added n-butyl lithium (2.5M in hexanes; 4.2 mL; 10.4 mmol) via syringe over 15 minutes. After stirring at −40° C. for thirty minutes, HMPA (1.4 mL; 8 mmol) was injected over two minutes and stirred for 10 minutes followed by rapid addition of propylene oxide (0.62 mL; 8.8 mmol). After stirring at −40° C. for 1 hour, the reaction was quenched with aqueous ammonium chloride (5 mL), diluted with water (30 mL) and extracted with ethyl acetate (70 mL). The organic layer was washed with 25 mL of water and 25 mL of brine, dried over anhydrous sodium sulfate and evaporated to yield 3.5 g of a viscous yellow oil. The crude alcohol was purified by flash chromatography on silica gel using a 20-60% ethyl acetate/hexane gradient affording the product as a colorless, viscous oil (2.7 g; 91%). $^1$H NMR (CDCl$_3$; 300 MHz) δ 1.1(d, 3H); 2.0-2.5 (m, 7H); 2.75 (m, 4H); 3.8 (s, 3H); 3.9-4.1 (m, 5H); 5.0 (m, 1H) 6.9 (d, 1H); 7.5 (m, 2H). ES-MS [M+H]+=371.2

The following compounds were synthesized in a similar manner with different starting materials:
1-{2-[4-Methoxy-3-(3R)-tetrahydrofuranyloxyphenyl]-1,3-dithian-2-yl}butan-2-ol.

Example 12

Synthesis of 1-{2-[4-Methoxy-3-(3R)-tetrahydro-furanyloxyphenyl]-1,3-dithian-2-yl}propan-2-one

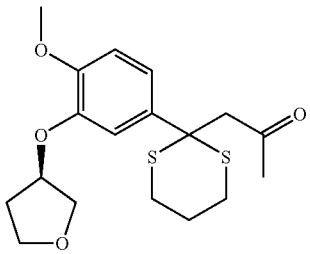

1-{2-[4-Methoxy-3-(3R)-tetrahydrofuranyloxyphenyl]-1,3-dithian-2-yl}propan-2-ol (158 mg; 0.42 mmol) was stirred in dichloromethane (5 mL) and treated with Dess Martin periodinane (15% solution in dichloromethane; 356 mg; 0.84 mmol) and stirred at room temperature for 15 minutes. The solvent was concentrated under reduced pressure and the residue was loaded onto a column of silica gel and eluted with a 20-60% ethyl acetate/hexane gradient. The product was isolated as an oil (23 mg; 15%). $^1$H NMR (CDCl$_3$; 300 MHz) δ 2.0(s, 3H); 2.1-2.5 (m, 4H); 2.8 (m, 4H); 3.2 (s, 2H); 3.8-4.2 (m, 7H); 5.0 (m, 1H); 6.9 (m, 1H); 7.5 (m, 2H). ES-MS [M+H]+=369.1

The following compounds were synthesized in a similar manner with different starting materials:
1-{2-[4-Methoxy-3-(3R)-tetrahydrofuranyloxyphenyl]-1,3-dithian-2-yl}butan-2-one.

Alternative Method for Example 12.

1-{2-[4-Methoxy-3-(3R)-tetrahydrofuranyloxyphenyl]-1,3-dithian-2-yl}propan-2-ol (119 mg; 0.32 mmol) was stirred in dichloromethane (5 mL) and treated with Dess-Martin periodinane (15% solution in dichloromethane; 173 mg; 0.41 mmol) and stirred at room temperature for 10 minutes. Upon formation of a precipitate, thin layer chromatography analysis using hexane/ethyl acetate (1:1 v/v) determined the reaction to be complete. The reaction was diluted with dichloromethane (40 mL) and washed with 20 mL portions of aqueous sodium bicarbonate and brine. The organic layer was dried over anhydrous sodium sulfate and evaporated to a crude solid, which was used as such in Example 7.

Example 13

Synthesis of 1-(2-Methoxybenzyl)-5-[4-methoxy-3-(3R)-tetrahydrofuranyloxyphenyl]-3-methyl-1H-pyrazole

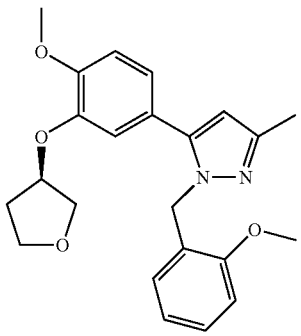

1-{2-[4-Methoxy-3-(3R)-tetrahydrofuranyloxyphenyl]-1,3-dithian-2-yl}propan-2-one (115 mg, 0.32 mmol) was reconstituted in toluene (5 mL) and treated with 2-methoxybenzyl hydrazine dihydrochloride (144 mg; 0.64 mmol) and molecular sieves (4A; 500 mg). The reaction was heated at 100° C. for two hours and cooled to room temperature. Molecular sieves were removed via filtration and the filtrate was diluted with ethyl acetate (50 mL), washed with 20 mL portions of water and brine. The organic layer was dried over anhydrous sodium sulfate and concentrated to an oil. The product was isolated by flash chromatography on silica gel using a 20-50% ethyl acetate/hexane gradient to afford 57 mg (45%) of 1-(2-methoxybenzyl)-5-[4-methoxy-3-(3R)-tetrahydrofuranyloxyphenyl]-3-methyl-1H-pyrazole as a yellow foam. $^1$H NMR (CDCl$_3$; 300 MHz) δ 1.7-2.0 (m, 2H); 2.3 (s, 3H); 3.6-4.0 (m, 10H); 4.5 (m, 1H); 5.3 (s, 2H); 6.2 (s, 1H); 6.6 (m, 1H); 6.7 (d, 1H); 6.8-7.0 (m, 4H); 7.2 (d, 1H). ES-MS [M+H]+=395.3

The following compounds were synthesized in a similar manner with different starting materials:
1-Benzyl-5-[4-methoxy-3-(3R)-tetrahydrofuranyloxyphenyl]-3-methyl-1H-pyrazole;
5-[4-Methoxy-3-(3R)-tetrahydrofuranyloxyphenyl]-3-methyl-1-phenyl-1H-pyrazole;
1-Cyclohexyl-5-[4-methoxy-3-(3R)-tetrahydrofuranyloxyphenyl]-3-methyl-1H-pyrazole;
1-(1-Butyl)-5-[4-methoxy-3-(3R)-tetrahydrofuranyloxyphenyl]-3-methyl-1H-pyrazole;
1-(2-Fluorophenyl)-5-[4-methoxy-3-(3R)-tetrahydrofuranyloxyphenyl]-3-methyl-1H-pyrazole;

1-(4-Chlorophenyl)-5-[4-methoxy-3-(3R)-tetrahydrofuranyloxyphenyl]-3-methyl-1H-pyrazole;
3-Ethyl-1-(2-methoxybenzyl)-5-[4-methoxy-3-(3R)-tetrahydrofuranyloxyphenyl]-1H-pyrazole;
1-Cyclohexyl-3-ethyl-5-[4-methoxy-3-(3R)-tetrahydrofuranyloxyphenyl]-1H-pyrazole;
1-Benzyl-3-ethyl-5-[4-methoxy-3-(3R)-tetrahydrofuranyloxyphenyl]-1H-pyrazole;
Ethyl 3-ethyl-[5-(4-methoxy-3-(3R)-tetrahydrofuranyloxyphenyl)-1H-pyrazol-1-yl]acetate;
1-(2,3-Dimethylphenyl)-3-ethyl-5-[4-methoxy-3-(3R)-tetrahydrofuranyloxyphenyl]-1H-pyrazole;
1-(3,4-Dimethylphenyl)-3-ethyl-5-[4-methoxy-3-(3R)-tetrahydrofuranyloxyphenyl]-1H-pyrazole;
3-Ethyl-5-[4-methoxy-3-(3R)-tetrahydrofuranyloxyphenyl]-1-(2-methylphenyl)-1H-pyrazole;
1-(2-Benzothiazolyl)-5-[4-methoxy-3-(3R)-tetrahydrofuranyloxyphenyl]-3-methyl-1H-pyrazole;
1-(3,4-Dimethylphenyl)-5-[4-methoxy-3-(3R)-tetrahydrofuranyloxyphenyl]-3-methyl-1H-pyrazole;
1-(2,3-Dimethylphenyl)-5-[4-methoxy-3-(3R)-tetrahydrofuranyloxyphenyl]-3-methyl-1H-pyrazole;
5-[4-Methoxy-3-(3R)-tetrahydrofuranyloxyphenyl]-3-methyl-1-(3-nitrophenyl)-1H-pyrazole;
5-[4-Methoxy-3-(3R)-tetrahydrofuranyloxyphenyl]-3-methyl-1-(2-methylphenyl)-1H-pyrazole;
5-[4-Methoxy-3-(3R)-tetrahydrofuranyloxyphenyl]-3-methyl-1-(2-phenylethyl)-1H-pyrazole;
5-[4-Methoxy-3-(3R)-tetrahydrofuranyloxyphenyl]-3-methyl-1-(4-trifluoromethoxyphenyl)-1H-pyrazole;
5-[4-Methoxy-3-(3R)-tetrahydrofuranyloxyphenyl]-3-methyl-1-(2-quinoxalinyl)-1H-pyrazole;
5-[4-Methoxy-3-(3R)-tetrahydrofuranyloxyphenyl]-1-(4-methoxyphenyl)-3-methyl-1H-pyrazole;
5-[4-Methoxy-3-(3R)-tetrahydrofuranyloxyphenyl]-1-(2-methoxycarbonyl-3-thienyl)-3-methyl-1H-pyrazole;
1-[2-(6-Fluoropyridyl)]-5-[4-methoxy-3-(3R)-tetrahydrofuranyloxyphenyl]-3-methyl-1H-pyrazole;
5-[4-Methoxy-3-(3R)-tetrahydrofuranyloxyphenyl]-3-methyl-1-(2-pyridyl)-1H-pyrazole;
1-[2-(6-Chloropyridyl)]-5-[4-methoxy-3-(3R)-tetrahydrofuranyloxyphenyl]-3-methyl-1H-pyrazole.

Example 14

Synthesis of 1-(3,4-Difluorobenzyl)-5-[4-methoxy-3-(3R)-tetrahydrofuranyloxyphenyl]-1H-pyrazole

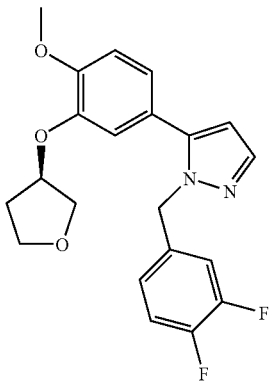

2-{4-Methoxy-3-(3R)-tetrahydrofuranyloxyphenyl}-5,5-dimethyl-[1,3,2]dioxaborinane (87 mg, 0.28 mmol), 5-bromo-1-(3,4-difluorobenzyl)-1H-pyrazole (65 mg, 0.23 mmol), Pd(PPh$_3$)$_2$Cl$_2$ (37 mg. 0.004 mmol), 2 M Na$_2$CO$_3$ aqueous solution (0.2 mL) and 3 mL of a solvent mixture which consisted of 7:3:2::DME:H$_2$O:EtOH was placed into a 2.0-5.0 mL Smith Process vial. This was sealed and placed into a Personal Chemistry Emrys Optimizer, stirred for 30 seconds, and then heated to 140° C. for 120 seconds. The solution was then diluted with 10 mL water and 10 mL ethyl acetate. The organic layer was separated, dried over Na$_2$SO$_4$, filtered and the solvent was removed. Purification by silica gel column chromatography using a gradient elution from 10% to 50% ethyl acetate in hexanes provided 72 mg (79%) of 1-(3,4-difluorobenzyl)-5-[4-methoxy-3-(3R)-tetrahydrofuranyloxyphenyl]-1H-pyrazole as a clear oil. $^1$H-NMR (CDCl$_3$, 300 MHz) δ 7.6 (d, 1H), 7.1-6.8 (m, 5H), 6.7 (d, 1H), 6.3 (d, 1H), 5.3 (s, 2H), 4.8 (m, 1H), 4.0-3.8 (m, 7H), 2.1-2.0 (m, 2H). (M+1)=387.2

The following compounds were synthesized in a similar manner with different starting materials:
1-(2,3-Difluorobenzyl)-5-(3,4-dimethoxyphenyl)-1H-pyrazole;
5-[4-Methoxy-3-(3R)-tetrahydrofuranyloxyphenyl]-1-(4-methybenzyl)-1H-pyrazole;
1-(4-tert-Butylbenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-trifluoromethylbenzyl)-1H-pyrazole;
1-(3,4-Difluorobenzyl)-5-[4-methoxy-3-(3R)-tetrahydrofuranyloxyphenyl]-1H-pyrazole;
1-(2-Fluorobenzyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(3-nitrobenzyl)-1H-pyrazole;
5-[4-Methoxy-3-(3R)-tetrahydrofuranyloxyphenyl]-1-(4-methoxycarbonylbenzyl)-1H-pyrazole;
1-(3-Fluorobenzyl)-5-[4-methoxy-3-(3R)-tetrahydrofuranyloxyphenyl]-1H-pyrazole;
1-(3,5-Dimethoxybenzyl)-5-[4-methoxy-3-(3R)-tetrahydrofuranyloxyphenyl]-1H-pyrazole;
1-Benzyl-5-[4-methoxy-3-(3R)-tetrahydrofuranyloxyphenyl]-1H-pyrazole;
1-(3-Methoxybenzyl)-5-[4-methoxy-3-(3R)-tetrahydrofuranyloxyphenyl]-1H-pyrazole;
1-(4-Fluorobenzyl)-5-[4-methoxy-3-(3R)-tetrahydrofuranyloxyphenyl]-1H-pyrazole;
1-(3,4-Difluorobenzyl)-5-(3-fluoro-4-methoxyphenyl)-1H-pyrazole;
5-(3-Fluoro-4-methoxyphenyl) 1-(4-methoxycarbonylbenzyl)-1H-pyrazole;
1-(2,6-Difluorobenzyl)-5-[4-methoxy-3-(3R)-tetrahydrofuranyloxyphenyl]-1H-pyrazole;
1-(4-Fluorobenzyl)-5-(3-fluoro-4-methoxyphenyl)-1H-pyrazole.

Example 15

Synthesis of 2-[4-Methoxy-3-(3R)-tetrahydrofuranyloxyphenyl]-5,5-dimethyl-[1,3,2]dioxaborinane

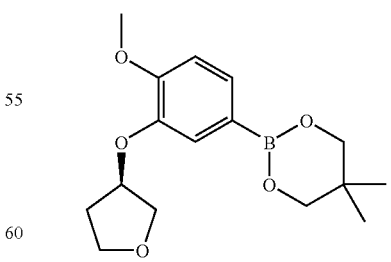

1-Bromo-4-methoxy-3-(3R)-tetrahydrofuranyloxybenzene (500 mg, 1.83 mmol) was added to a flask containing 10 mL of THF. This was cooled to −78° C. under argon and butyllithium (1.5 mL, 2.5 M) was slowly added. After stirring at −78° C. for 1.5 hours, trimethyl borate (0.41 mL, 3.7 mmol) in 10 mL of THF was added and the mixture was allowed to warm to room temperature overnight. The reaction was quenched by the addition of 20 mL of an aqueous saturated solution of NH₄Cl and 20 mL of diethyl ether. The organic layer was washed with 10 mL of water, 10 mL of brine, dried over Na₂SO₄, and concentrated. The residue was dissolved in 18 mL of toluene and 270 mg of (2.6 mmol) 2,2-dimethylpropane-1,3-diol was added. This was heated to reflux for 4 hours, concentrated, and diluted with hexanes. The insoluble material was washed three times with hexanes. The combined organic layer was removed and the product was purified using column chromatography using a gradient elution from 10% to 100% ethyl acetate in hexanes to give 198 mg (35%) of 2-[4-methoxy-3-(3R)-tetrahydrofuranyloxyphenyl]-5,5-dimethyl-[1,3,2]dioxaborinane as a clear oil. ¹H-NMR (CDCl₃, 300 MHz) δ 7.4 (d, 1H), 7.3 (d, 1H), 6.9 (d, 1H), 5.0 (m, 1H), 4.0 (m, 3H), 3.9-3.8 (m, 4H), 3.7, (s, 4H), 2.1 (m, 2H), 1.0 (s, 6H).

Example 16

Synthesis of 1-[4-Methoxy-3-(3R)-tetrahydrofuranyloxyphenyl]ethanol

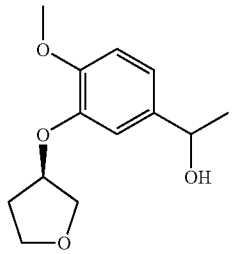

A flask containing 1.7 g (7.5 mmol) of 4-methoxy-3-(3R)-tetrahydrofuranyloxybenzaldehyde and 75 mL of THF was cooled to −78° C. under argon and 5.0 mL (3 M) of MeMgCl was slowly added. The reaction was stirred at room temperature for 12 hours and was quenched by the addition of 100 mL of saturated aqueous NH₄Cl. The aqueous layer was extracted with 3×50 mL of ethyl acetate and the combined organic extracts were dried over Na₂SO₄, filtered and concentrated. Purification by silica gel column chromatography using a gradient elution from 50% to 100% ethyl acetate in hexanes yielded 1.46 g (80%) of 1-[4-methoxy-3-(3R)-tetrahydrofuranyloxyphenyl]-ethanol as a white solid. ¹H-NMR (CDCl₃, 300 MHz) δ 6.9 (m, 3H), 5.0 (m, 1H), 4.8 (m, 1H), 4.0-3.8 (m, 4H), 3.8 (s, 3H), 2.1 (m, 2H), 1.4 (d, 3H). (M−H₂O+1)=221.2

Example 17

Synthesis of 1-[4-Methoxy-3-(3R)-tetrahydrofuranyloxyphenyl]ethanone

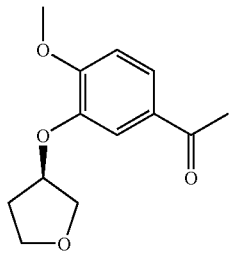

Pyridium chlorochromate (2.8 g; 12.3 mmol) was added to a flask containing 1.46 g (6.1 mmol) of 1-[4-methoxy-3-(3R)-tetrahydrofuranyloxyphenyl]ethanol and 65 mL of CH₂Cl₂. The mixture was stirred at room temperature for one hour and the solids were filtered through silica gel, rinsing with 200 mL ethyl acetate. The solvent was removed and the residue was purified by column chromatography using a gradient elution from 20% to 50% ethyl acetate in hexanes to give 1.2 g (83%) of 1-[4-methoxy-3-(3R)-tetrahydrofuranyloxyphenyl]ethanone as a white solid. ¹H-NMR (CDCl₃, 300 MHz) δ 7.5 (d, 1H), 7.4 (d, 1H), 6.8 (d, 1H), 4.9 (m, 1H), 4.0-3.9 (m, 3H), 3.8 (m, 4H), 2.5 (s, 3H), 2.1 (m, 2H). (M+1)=237.2

Example 18

Synthesis of 3-[4-Methoxy-3-(3R)-tetrahydrofuranyloxyphenyl]-3-oxopropionaldehyde

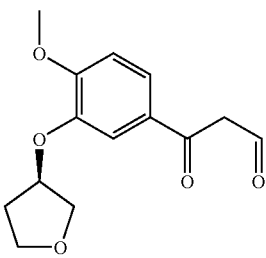

A suspension of sodium hydride (60% suspension in mineral oil, 210 mg, 5.25 mmol) in 4 mL of THF under argon was treated sequentially with 0.4 mL (4.77 mmol) of ethyl formate and a solution of 939 mg (3.98 mmol) of 1-[4-methoxy-3-(3R)-tetrahydrofuranyloxyphenyl]ethanone in 2 mL of THF. The resulting mixture was stirred at room temperature for 4 hours, and then acidified with 0.5 N HCl to pH 2 and extracted with 3×10 mL of ethyl acetate. The organic layer was dried over Na₂SO₄, filtered and the solvent removed. Purification by column chromatography on silica gel using a gradient elution from 20% to 50% ethyl acetate in hexanes furnished 218 mg (21%) of 3-[4-methoxy-3-(3R)-tetrahydrofuranyloxyphenyl]-3-oxopropionaldehyde as a yellow solid. ¹H-NMR (CDCl₃, 300 MHz) δ 8.0 (s, 1H), 7.6-7.5 (m, 2H), 7.4 (d, 1H), 6.1 (d, 1H), 5.0 (m, 1H), 4.0 (m, 4H), 3.9 (s, 3H), 2.2 (m, 2H). (M+1)=265.2

The following compounds were synthesized in a similar manner with different starting materials:
4,4,4-trifluoro-1-{4-methoxy-3-[(3R)-tetrahydrofuran-3-yloxy]phenyl}butane-1,3-dione;
Ethyl 1-[4-methoxy-3-(3R)-tetrahydrofuranyloxyphenyl]-1,3-dionebutanoate.

Example 19

Synthesis of 3-Dimethylamino-1-[4-methoxy-3-(3R)-tetrahydrofuranyloxyphenyl]propenone

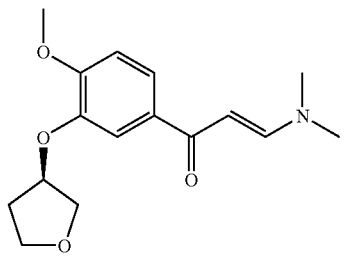

To a solution of 440 mg (1.86 mmol) of 1-[4-methoxy-3-(3R)-tetrahydrofuranyloxyphenyl]-ethanone in 15 mL of DMF was added 0.30 mL (2.24 mmol) of N,N-dimethylformamide dimethyl acetal. The resulting mixture was heated to 140° C. for 16 hours, then cooled to room temperature and quenched by the addition of 25 mL of water. The mixture was extracted with 4×25 mL of ethyl acetate and the combined organic fractions were dried over Na$_2$SO$_4$, filtered and concentrated. Purification by column chromatography over silica gel using a gradient elution from 100% CH$_2$Cl$_2$ to 90:10:5:CH$_2$Cl$_2$:MeOH:NH$_4$OH provided 257 mg (56%) of 3-dimethylamino-1-[4-methoxy-3-(3R)-tetrahydrofuranyloxyphenyl]propenone as a yellow oil and 115 mg of the starting ketone. $^1$H-NMR (CDCl$_3$, 300 MHz) δ 8.0 (s, 1H), 7.7 (d, 1H), 7.5 (m, 2H), 6.9 (d, 1H), 5.7 (d, 1H), 5.1 (m, 1H), 4.0 (m, 3H), 3.9 (s, 4H), 2.9 (s, 3H), 2.8 (s, 3H), 2.2 (m, 2H). (M+1)=292.1

Example 20

Synthesis of 1-(4-Methoxyphenyl)-5-[4-methoxy-3-(3R)-tetrahydrofuranyloxyphenyl]-1H-pyrazole

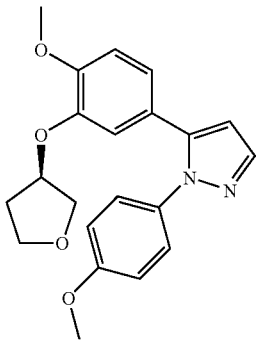

3-[4-Methoxy-3-(3R)-tetrahydrofuranyloxyphenyl]-3-oxopropionaldehyde (45 mg, 0.17 mmol), 4-methoxyphenyl hydrazine hydrochloride (36 mg, 0.20 mmol) and 1.7 mL of ethanol were combined in a 0.5-2.0 mL Smith Process Vial. The vial was sealed and heated to 140° C. for 300 seconds using a Personal Chemistry Emrys Optimizer. The solvent was removed and purification by silica gel column chromatography using a gradient elution from 20% to 100% ethyl acetate in hexanes provided 40 mg (65%) of 1-(4-methoxyphenyl)-5-[4-methoxy-3-(3R)-tetrahydrofuranyloxyphenyl]-1H-pyrazole as a brown solid. $^1$H-NMR (CDCl$_3$, 300 MHz) δ 7.6 (d, 1H), 7.2 (m, 2H), 6.9 (m, 4H), 6.5 (d, 1H), 6.4 (d, 1H), 4.6 (m, 1H), 3.9-3.7 (m, 10H), 1.9 (m, 2H). (M+1)=367.2

The following compounds were synthesized in a similar manner with different starting materials:
Ethyl 1-Benzyl-5-[4-methoxy-3-(3R)-tetrahydrofuranyloxyphenyl]-1H-pyrazole-3-carboxylate;
1-Benzyl-5-[4-methoxy-3-(3R)-tetrahydrofuranyloxyphenyl]-3-trifluoromethyl-1H-pyrazole;
5-[4-Methoxy-3-(3R)-tetrahydrofuranyloxyphenyl]-1-phenyl-3-trifluoromethyl-1H-pyrazole;
Ethyl[5-(4-methoxy-3-(3R)-tetrahydrofuranyloxyphenyl)-3-trifluoromethyl-1H-pyrazol-1-yl]acetate;
[5-(4-Methoxy-3-(3R)-tetrahydrofuranyloxyphenyl)-3-trifluoromethyl-1H-pyrazol-1-yl]acetic acid;
Isopropyl[5-(4-methoxy-3-(3R)-tetrahydrofuranyloxyphenyl)-3-trifluoromethyl-1H-pyrazol-1-yl]acetate;
1-(3-Fluorobenzyl)-5-[4-methoxy-3-(3R)-tetrahydrofuranyloxyphenyl]-3-trifluoromethyl-1H-pyrazole;
5-[4-Methoxy-3-(3R)-tetrahydrofuranyloxyphenyl]-1-phenyl-1H-pyrazole;
1-Cyclohexyl-5-[4-methoxy-3-(3R)-tetrahydrofuranyloxyphenyl]-1H-pyrazole;
Ethyl 1-Benzyl-5-[4-methoxy-3-(3R)-tetrahydrofuranyloxyphenyl]-1H-pyrazole-3-carboxylate;
1-(4-Methoxyphenyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(2-phenylethyl)-1H-pyrazole;
1-(4-Fluorophenyl)-5-[4-methoxy-3-(3R)-tetrahydrofuranyloxyphenyl]-1H-pyrazole;
1-(4-Bromophenyl)-5-[4-methoxy-3-(3R)-tetrahydrofuranyloxyphenyl]-1H-pyrazole;
5-[4-Methoxy-3-(3R)-tetrahydrofuranyloxyphenyl]-1-(4-trifluoromethoxyphenyl)-1H-pyrazole;
5-[4-Methoxy-3-(3R)-tetrahydrofuranyloxyphenyl]-1-(2-pyridyl)-1H-pyrazole;
1-(2-Benzothiazolyl)-5-[4-methoxy-3-(3R)-tetrahydrofuranyloxyphenyl]-1H-pyrazole;
5-(3-Fluoro-4-methoxyphenyl)-1-(4-methoxyphenyl)-1H-pyrazole;
1-(2-Methoxyphenyl)-5-[4-methoxy-3-(3R)-tetrahydrofuranyloxyphenyl]-1H-pyrazole;
1-[2-(6-Fluoropyridyl)]-5-[4-methoxy-3-(3R)-tetrahydrofuranyloxyphenyl]-1H-pyrazole.

Example 21

Synthesis of 1-(4-Methoxyphenyl)-5-[4-methoxy-3-(3R)-tetrahydrofuranyloxyphenyl]-1H-pyrazole

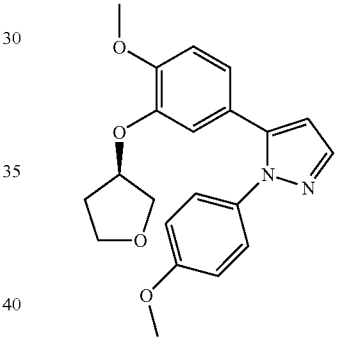

3-Dimethylamino-1-[4-methoxy-3-(3R)-tetrahydrofuranyloxyphenyl]propenone, (461 mg, 1.6 mmol), 4-methoxyphenyl hydrazine hydrochloride (304 mg, 1.74 mmol), and 5 mL of ethanol were combined in a 2.0-5.0 mL Smith Process Vial. The vial was sealed and heated to 140° C. for 300 seconds, quenched with 10 mL of water, and the aqueous layer was extracted with 3×10 mL of ethyl acetate. The combined organic fractions were dried over Na$_2$SO$_4$, filtered and concentrated. Purification by silica gel column chromatography using a gradient elution from 20% to 100% ethyl acetate in hexanes provided 436 mg (75%) of 1-(4-methoxyphenyl)-5-[4-methoxy-3-(3R)-tetrahydrofuranyloxyphenyl]-1H-pyrazole as a brown solid. $^1$H-NMR (CDCl$_3$, 300 MHz) δ 7.6 (d, 1H), 7.2 (m, 2H), 6.9 (m, 4H), 6.5 (d, 1H), 6.4 (d, 1H), 4.6 (m, 1H), 3.9-3.7 (m, 10H), 1.9 (m, 2H). (M+1)=367.2

The following compounds were synthesized in a similar manner with different starting materials:
1-Benzyl-5-(3-fluoro-4-methoxyphenyl)-1H-pyrazole;
Ethyl 2-{5-[4-methoxy-3-(3R)-tetrahydrofuranyloxyphenyl]pyrazol-1-yl}acetate;
5-(3,4-Dimethoxyphenyl)-1-(4-fluorobenzyl)-1H-pyrazole;
5-(3,4-Dimethoxyphenyl)-1-(4-methoxyphenyl)-1H-pyrazole;
3-[(1-Cyclopentyl-3-ethylindazol)-6-yl]-1-(4-carboxyphenyl)-1H-pyrazole;

3-[(1-Cyclopentyl-3-ethylindazol)-6-yl]-1-(4-methoxyphenyl)-1H-pyrazole;

5-[4-Methoxy-3-(3R)-tetrahydrofuranyloxyphenyl]-1-[4-(4-morpholinyl)phenyl]-1H-pyrazole;

1-(4-Carboxyphenyl)-5-[4-methoxy-3-(3R)-tetrahydrofuranyloxyphenyl]-1H-pyrazole.

Example 22

Synthesis of 5-(3-Cyclopentyloxy-4-methoxyphenyl)-3-methyl-1-phenyl-1H-pyrazole.

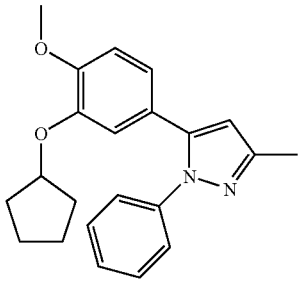

A solution of 5-chloro-3-methyl-1-phenyl-1H-pyrazole (61.8 mg, 0.32 mmol) in 5 mL of THF was cooled to −78° C. and t-butyllithium (0.47 mL, 1.7 M in heptane) was slowly added. The mixture was stirred at −78° C. for 1.5 hours and then zinc chloride (1.56 mL, 0.5 M) was added and after stirring at −78° C. for 15 minutes was warmed to room temperature. A solution containing 4-bromo-2-cyclopentyloxy-1-methoxybenzene (148 mg, 0.54 mmol) and Pd(PPh$_3$)$_4$ (35 mg, 0.03 mmol) in 1 mL of THF was added and the reaction was heated to 60° C. for 12 hours. The mixture was diluted with 20 mL of ethyl acetate and the organic layer was washed with 10 mL of a saturated ammonium chloride solution, 20 mL of water and 20 mL of brine. The organic layer was dried over sodium sulfate, filtered and concentrated. Purification by silica gel column chromatography using a gradient elution from 20% to 50% ethyl acetate in hexanes yielded 31 mg of 5-(3-cyclopentyloxy-4-methoxyphenyl)-3-methyl-1-phenyl-1H-pyrazole.
$^1$H-NMR (CDCl$_3$, 300 MHz) δ 7.3 (m, 5H), 6.8 (m, 2H), 6.6 (d, 1H), 6.3 (s, 1H), 4.4 (m, 1H), 3.8 (s, 3H). 2.4 (s, 3H), 1.7-1.5 (m, 8H). (M+1)=349.1

The following compounds were synthesized in a similar manner with different starting materials:

5-[4-Methoxy-3-(3R)-tetrahydrofuranyloxyphenyl]-1-(4-trifluoromethoxybenzyl)-1H-pyrazole.

Example 23

Synthesis of {5-[4-Methoxy-3-(3R)-tetrahydrofuranyloxyphenyl]-3-trifluoromethyl-1H-pyrazol-1-yl}acetic acid

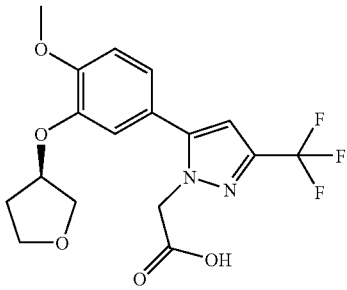

{5-[4-Methoxy-3-(3R)-tetrahydrofuranyloxyphenyl]-3-trifluoromethyl-pyrazol-1-yl}-acetic acid ethyl ester (239 mg, 0.58 mmol) was dissolved in 5 mL of a solution made of 35 g KOH in 25 mL water. The reaction mixture was diluted with 100 mL of methanol, heated to 100° C. for 1 hour, and cooled to room temperature. Acidification with 1N HCl resulted in the formation of a white solid, which was isolated by filtration to give 100 mg of {5-[4-methoxy-3-(3R)-tetrahydrofuranyloxyphenyl]-3-trifluoromethyl-1H-pyrazol-1-yl}acetic acid. $^1$H-NMR (CDCl$_3$, 300 MHz) δ 6.9 (s, 2H), 6.8 (s, 1H), 6.5 (s, 1H), 4.9 (m, 4H), 4.0 (s, 4H), 3.9 (s, 3H), 2.2 (s, 2H). (M+1)

The following compounds were synthesized in a similar manner with different starting materials:

1-Benzyl-5-[4-methoxy-3-(3R)-tetrahydrofuranyloxyphenyl]-1H-pyrazole-3-carboxylic acid;

1-(4-Carboxybenzyl)-5-[4-methoxy-3-(3R)-tetrahydrofuranyloxyphenyl]-1H-pyrazole;

1-(4-Carboxybenzyl)-5-(3-fluoro-4-methoxyphenyl)-1H-pyrazole.

Example 24

Synthesis of N-(3-Fluorophenyl)-2-{5-[4-methoxy-3-(3R)-tetrahydrofuranyloxyphenyl]-3-trifluoromethylpyrazol-1-yl}acetamide

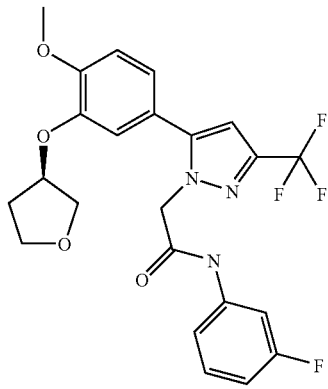

A solution of {5-[4-methoxy-3-(3R)-tetrahydrofuranyloxyphenyl]-3-trifluoromethyl-1H-pyrazol-1-yl}acetic acid (50 mg, 0.13 mmol) in 2 mL of DMF was treated with HOBt (33 mg, 0.22 mmol), diisopropylethylamine (38 uL, 0.22 mmol), 3-fluoroaniline (21 uL, 0.22 mmol), and EDCI (38 uL, 0.22 mmol) and was then stirred at room temperature for 16 h. The reaction was diluted with 10 mL of ethyl acetate; the organic layer was separated and sequentially washed with 10 mL of water, 10 mL of 1N HCl, 10 mL of saturated NaHCO$_3$, and 10 mL of brine, dried (Na$_2$SO$_4$) and concentrated. Purification by silica gel column chromatography using 10% ethyl acetate in hexanes provided 21 mg of N-(3-fluorophenyl)-2-{5-[4-methoxy-3-(3R)-tetrahydrofuranyloxyphenyl]-3-trifluoromethyl-pyrazol-1-yl}acetamide as a white solid.

$^1$H-NMR (CDCl$_3$, 300 MHz) δ 8.6 (s, 1H), 7.5 (d, 1H), 7.3 (m, 1H), 7.1-7.0 (m, 3H), 7.0-6.8 (m, 2H), 6.6 (s, 1H), 5.0 (m, 1H), 4.9 (s, 2H), 4.0-3.9 (m, 7H), 2.2 (m, 2H).

The following compounds were synthesized in a similar manner with different starting materials:

N-Cyclopropyl-2-{5-[4-methoxy-3-(3R)-tetrahydrofuranyloxyphenyl]-pyrazol 1-yl}acetamide;

N-Isopropyl-2-{5-[4-methoxy-3-(3R)-tetrahydrofuranyloxyphenyl]-pyrazol-1-yl}acetamide;

N-Phenyl-2-{5-[4-methoxy-3-(3R)-tetrahydrofuranyloxyphenyl]-pyrazol-1-yl}acetamide;

N,N-Diethyl-2-{5-[4-methoxy-3-(3R)-tetrahydrofuranyloxyphenyl]-pyrazol-1-yl}acetamide.

Example 25

Synthesis of 2-{1-Benzyl-5-[4-methoxy-3-(3R)-tetrahydrofuranyloxyphenyl]-1H-pyrazol-3-yl}propan-2-ol and 1-{1-Benzyl-5-[4-methoxy-3-(3R)-tetrahydrofuranyloxyphenyl]-1H-pyrazol-3-yl}ethanone

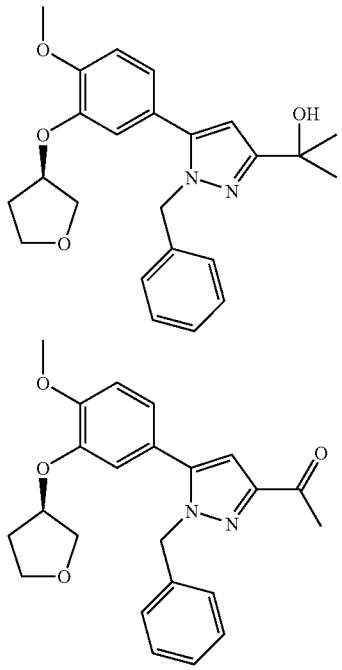

A solution of 1-benzyl-5-[4-methoxy-3-(3R)-tetrahydrofuranyloxyphenyl]-1H-pyrazole-3-carboxylic acid ethyl ester (144 mg, 0.34 mmol) in 3 mL of THF was cooled to −78° C. under argon and MeMgCl (0.34 mL, 3.0 M) was added slowly. The solution was warmed to room temperature over 2 hours and then 10 mL of saturated aqueous NH$_4$Cl was added. The mixture was extracted with 3×10 mL of ethyl acetate and the combined organic fractions were dried over Na$_2$SO$_4$, filtered and concentrated. Purification by silica gel column chromatography using a gradient elution from 20% to 50% ethyl acetate in hexanes yielded 55 mg of 2-{1-benzyl-5-[4-methoxy-3-(3R)-tetrahydrofuranloxyphenyl]-1H-pyrazol-3-yl}propan-2-ol A as a clear oil and 20 mg of 1-{1-benzyl-5-[4-methoxy-3-(3R)-tetrahydrofuranyloxyphenyl]-1H-pyrazol-3-yl}ethanone B as a clear oil. $^1$H-NMR (CDCl$_3$, 300 MHz) A δ 7.3 (m, 3H), 7.0 (d, 2H), 6.9 (m, 2H), 6.6 (d, 1H), 6.2 (s, 1H), 5.3 (s, 2H), 4.6 (m, 1H), 4.0-3.7 (m, 7H), 2.0 (m, 2H), 1.6 (s, 6H). $^1$H-NMR (CDCl$_3$, 300 MHz) B δ 7.3 (m, 3H), 7.0 (d, 2H), 6.9 (s, 2H), 6.8 (s, 1H), 6.6 (s, 1H), 5.3 (s, 2H), 4.6 (m, 1H), 4.0-3.7 (m, 7H), 2.6 (s, 3H), 1.9 (m, 2H), (M+1) A 409.2 B 393.2

Example 26

Synthesis of {1-Benzyl-5-[4-methoxy-3-(3R)-tetrahydrofuranyloxyphenyl]-1H-pyrazol-3-yl}methanol

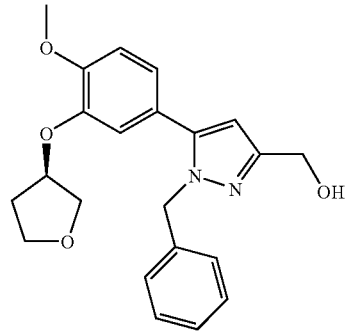

A solution of 1-benzyl-5-[4-methoxy-3-(3R)-tetrahydrofuranyloxyphenyl]-1H-pyrazole-3-carboxylic acid ethyl ester (62 mg, 0.15 mmol) in 3 mL THF was cooled to 0° C. under argon. LAH (0.25 mL, 1M) was added and after stirring for 1 hour the reaction was quenched by the slow addition of 5 mL of methanol and 5 mL of 0.1 N HCl. The aqueous layer was extracted with 2×10 mL of ethyl acetate and the combined organic fractions were concentrated. Purification by silica gel column chromatography using a gradient elution from 50% to 100% ethyl acetate in hexanes yielded 20 mg of {1-Benzyl-5-[4-methoxy-3-(3R)-tetrahydrofuranyloxyphenyl]-1H-pyrazol-3-yl}methanol as a clear oil. $^1$H-NMR (CDCl$_3$, 300 MHz) δ 7.3 (m, 3H), 7.0 (d, 2H), 6.9 (m, 2H), 6.6 (d, 1H), 6.3 (s, 1H), 5.3 (s, 2H), 4.7 (s, 2H), 4.6 (m, 1H), 3.9-3.7 (m, 7H), 2.5 (s, 1H), 2.0-1.4 (m, 2H). (M+1)=381.2

The following compounds were synthesized in a similar manner with different starting materials:

1-(2-Hydroxyethyl)-5-[4-methoxy-3-(3R)-tetrahydrofuranyloxyphenyl]-1H-pyrazole.

Example 27

Synthesis of 5-Bromo-1-(2,6-difluorobenzyl)-1H-pyrazole

Step 1:
2-(2,6-Difluorobenzyl)-1-hydroxy-1H-pyrazole

1-Hydroxypyrazole (49.3 mg, 0.59 mmol, 1.0 eq) was mixed with 165.8 mg (0.80 mmol, 1.36 eq) of 2,6-difluorobenzyl bromide in ~1-2 mL of anhydrous CHCl$_3$ under argon. The mixture was heated at 80° C. for 18 h under inert atmosphere in a sealed flask without condenser. The residue was partitioned between 37 weight percent aqueous HCl and toluene. The aqueous layer was collected and the toluene fraction extracted again with 37 weight percent aqueous HCl. The combined aqueous HCL fractions were neutralized with 5N aqueous NaOH to pH~11-12 and then back-extracted with 3×30 mL of CHCl$_3$. The organic layers were combined, washed with brine, dried over Na$_2$SO$_4$ and concentrated under reduced pressure to yield 86.3 mg (70.1% yield) of 2-(2,6-difluorobenzyl)-1-hydroxy-1H-pyrazole as a tan brown solid. $^1$H NMR (CDCl$_3$ 300 MHz) δ 7.37 (m, 1H), 7.18 (d, 1H), 6.95 (t, 2H), 6.85 (d, 1H), 6.11 (t, 1H), 5.43 (s, 2.00 H). LC/MS (ES) M+1=211.2

Step 2.
5-Bromo-1-(2,6-difluorobenzyl)-1H-pyrazole 2-(2,6-Difluorobenzyl)-1-hydroxy-1H-pyrazole (81.2 mg, 0.386 mmol, 1.0 eq) and 5 ml of anhydrous $CHCl_3$ were combined in a flame-dried 25 mL round-bottom flask under argon and cooled in an ice/water bath. A solution of $POBr_3$ (398.1 mg, 1.39 mmol, 3.60 eq) in 3 mL of $CHCl_3$ was added using a syringe in aliquots over an hour period with stirring. The reaction solution was warmed to room temperature and stirred for 16 hours. The $CHCl_3$ was removed in vacuo and the resulting orange mixture was neutralized with saturated aqueous $NaHCO_3$ and extracted with 3×30 mL of diethyl ether. The combined ether fractions were washed with brine, dried over $Na_2SO_4$ and concentrated in vacuo to yield 101.5 mg (96.7% yield) of 5-bromo-1-(2,6-difluorobenzyl)-1H-pyrazole as a hygroscopic orange-tan colored solid. $^1$H NMR ($CDCl_3$ 300 MHz) δ 7.51 (d, 1H), 7.34 (m, 1H), 6.94 (t, 2H), 6.29 (d, 1H), 5.50 (s, 2H). LC/MS (ES) M+1=273.1, 275.1

The following compounds were synthesized in a similar manner with different starting materials:
5-Bromo-1-(4-trifluoromethoxybenzyl)-1H-pyrazole;
5-Bromo-1-(2,3-difluorobenzyl)-1H-pyrazole;
5-Bromo-1-(4-methylbenzyl)-1H-pyrazole;
5-Bromo-1-(4-tert-butylbenzyl)-1H-pyrazole;
5-Bromo-1-(4-trifluoromethylbenzyl)-1H-pyrazole;
5-Bromo-1-(3,4-difluorobenzyl)-1H-pyrazole;
5-Bromo-1-(2-fluorobenzyl)-1H-pyrazole;
5-Bromo-1-(3-nitrobenzyl)-1H-pyrazole;
5-Bromo-1-(4-methoxycarbonylbenzyl)-1H-pyrazole;
5-Bromo-1-(3-fluorobenzyl)-1H-pyrazole;
5-Bromo-1-(3,5-dimethoxybenzyl)-1H-pyrazole;
1-Benzyl-5-bromo-1H-pyrazole;
5-Bromo-1-(3-methoxybenzyl)-1H-pyrazole;
5-Bromo-1-(4-fluorobenzyl)-1H-pyrazole;
5-Bromo-1-(2,6-difluorobenzyl)-1H-pyrazole.

Example 28

In Vitro Measurement of Type 4 Phosphodiesterase

Enzyme Preparation:

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 µl) expressing hPDE-4D6 were combined with 50 µl of assay mix and 10 µl of inhibitors and incubated for 12 min at room temperature. Final concentrations of assay components were: 0.4 µg enzyme, 10 mM Tris-HCl (pH 7.5), 10 mM $MgCl_2$, 3 uM cAMP, 0.002 U 5'-nucleotidase, and $3×10^4$ cpm of [3H]cAMP. The reaction was stopped by adding 100 µl of boiling 5 mM HCl. An aliquot of 75 µl of reaction mixture was transferred from each well to alumina columns (Multiplate; Millipore). Labeled adenosine was eluted into an OptiPlate by spinning at 2000 rpm for 2 min; 150 µl per well of scintillation fluid was added to the OptiPlate. The plate was sealed, shaken for about 30 min, and cpm of [$^3$H]adenosine was determined using a Packard Topcount 96 counter.

All test compounds were dissolved in 100% DMSO and diluted into the assay such that the final concentration of DMSO is 0.1%. DMSO does not affect enzyme activity at this concentration. A decrease in adenosine concentration is indicative of inhibition of PDE activity. This procedure may be used to screen compounds of the present invention for their ability to inhibit PDE4. $pIC_{50}$ values may be determined by screening 6 to 12 concentrations of compound ranging from 0.1 nM to 10,000 nM and then plotting drug concentration versus $^3$H-adenosine concentration. Prism® may be used to estimate $pIC_{50}$ values.

Compounds of the invention show activity in the range of 10 nM-5000 nM IC50 in the assay.

Example 29

Passive Avoidance in Rats, an In Vivo Test for Learning and Memory

The test may be performed as previously described [Zhang, H.-T., Crissman, A. M., Dorairaj, N. R., Chandler, L. J., and O'Donnell, J. M., *Neuropsychopharmacology*, 2000, 23, 198-204]. The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock may be delivered from a constant current source. All experimental groups may be first habituated to the apparatus the day before the start of the experiment. During the training, the rat (Male Spraque-Dawley (Harlan) weighing 250 to 350 g) may be placed in the illuminated compartment facing away from the closed guillotine door for 1 minute before the door was raised. The latency for entering the darkened compartment may be recorded. After the rat enters the darkened compartment, the door may be closed and a 0.5 mA electric shock was administered for 3 seconds. Twenty-four hours later, the rat may be administered 0.1 mg/kg of the test compound or saline, 30 minutes prior to the injection of saline or test compound (dosed from 0.1 to 2.5 mg/kg, i.p.), which was 30 minutes before the retention test starts. The rat may be again placed in the illuminated compartment with the guillotine door open. The latency for entering the darkened compartment may be recorded for up to 180 seconds, at which time the trial was terminated.

All data may be analyzed by analyses of variance (ANOVA); individual comparisons were made using Kewman-Keuls tests. Naïve rats required less than 30 seconds, on average, to cross from the illuminated compartment to the darkened compartment.

Example 30

Radial Arm Maze Task in Rats, an In Vivo Test for Learning and Memory

The test may be performed as previously described [Zhang, H.-T., Crissman, A. M., Dorairaj, N. R., Chandler, L. J., and O'Donnell, J. M., *Neuropsychopharmacology*, 2000, 23, 198-204.]. Five days after initial housing, rats (male Sprague-Dawley (Harlan) weighing 250 to 350 g) may be placed in the eight-arm radial maze (each arm was 60×10×12 cm high; the maze was elevated 70 cm above the floor) for acclimation for two days. Rats may be then placed individually in the center of the maze for 5 minutes with food pellets placed close to the food wells, and then, the next day, in the wells at the end of the arms; 2 sessions a day may be conducted. Next, four randomly selected arms may be then baited with one pellet of food each. The rat may be restricted to the center platform (26 cm in diameter) for 15 seconds and then allowed to move freely throughout the maze until it collected all pellets of food or 10 minutes passed, whichever came first. Four parameters may be recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error is zero and the average reference memory error is less than one in five successive trials, the rats may begin the drug tests. The test compound or saline may be injected 15 minutes prior to vehicle or test agent, which may be given 45 minutes before the test. Experiments are performed in a lighted room, which contained several extra-maze visual cues.

All data may be analyzed by analyses of variance (ANOVA); individual comparisons were made using Kewman-Keuls tests.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention. Upon further study of the specification, further aspects, objects and advantages of this invention will become apparent to those skilled in the art.

We claim:

1. A compound according to Formulas III or VI:

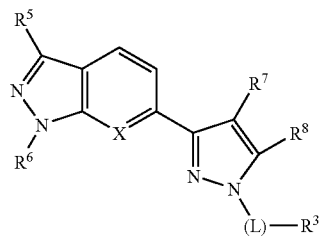

III

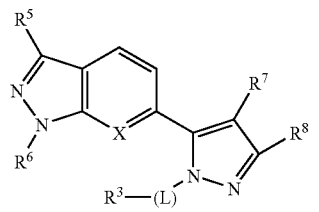

VI wherein
X is CH or N;
L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen, hydroxy, cyano or combinations thereof; $(CH_2)_nCONH$; $(CH_2)_nCON(C_{1-6}$-alkyl); $(CH_2)_nNHCO$; $(CH_2)_nCONHSO_2$; $(CH_2)_nSO_2NH$; $(CH_2)_nSO_2$; or $(CH_2)_nCO_2$;
n is 0 to 3;
$R^3$ is H,
  alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups,
  cycloalkyl having 3 to 8 carbon atoms, which is unsubstituted or substituted one or more times by halogen, oxo, alkyl, or combinations thereof,
  aryl having 6 to 14 carbon atoms, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, acylamido, imidazolyl, pyridinyl, morpholinyl, piperadinyl, piperazinyl, tetrazolyl, alkylsulphonimide, arylsulphonimide or combinations thereof,
  heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, tetrazolyl, alkylsulphonimide, arylsulphonimide, aryl, oxo, acylamido, or combinations thereof,
  arylalkyl having 7 to 16 carbon atoms, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, acylamido, tetrazolyl, alkylsulphonimide, arylsulphonimide, or combinations thereof and/or substituted in the alkyl portion by halogen, oxo, cyano, or combinations thereof,
  a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, arylsulphinyl, arylsulphonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof, cycloalkylalkyl having 4 to 16 carbon atoms, which is unsubstituted or substituted one or more times by halogen, oxo, alkyl or combinations thereof, or alkoxyalkyl having 3 to 8 carbon atoms;

$R^5$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups;

$R^6$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms, which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido, and acyloxy, or combinations thereof, arylalkyl having 7 to 16 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido, and acyloxy, or combinations thereof, a heterocyclic group, which is saturated, partially saturated or fully unsaturated, having 5 to 10 ring atoms in which at least 1 ring atom is an N, O or S atom which is unsubstituted or substituted one or more times by halogen, aryl, alkyl, alkoxy, alkoxycarbonyl, cyano, halogenated alkyl, nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen; and $R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl, carboxy, alkoxycarbonyl having 2 to 6 carbon atoms, —CO-alkyl having 2 to 6 carbon atoms, or phenyl;

or a pharmaceutically acceptable salt thereof, wherein said compound can be in the form of a mixture of enantiomers such as the racemate, or a mixture of diastereomers, or can be in the form of a single enantiomer or a single diastereomer.

2. A compound according to claim 1, wherein said compound is selected from Formulas III and VI:

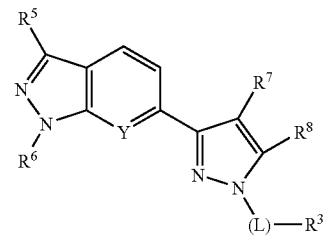

III

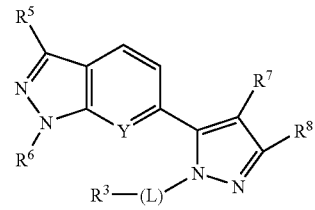

VI wherein

Y is CH or N;

L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen, hydroxy, cyano or combinations thereof; $(CH_2)_n$CONH; $(CH_2)_n$NHCO; $(CH_2)_n$CONHSO$_2$; $(CH_2)_n$SO$_2$NH; $(CH_2)_n$SO$_2$; or $(CH_2)_n$CO$_2$;

n is 0 to 3;

$R^3$ is H, alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, aryl having 6 to 14 carbon atoms, which is unsubstituted or substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy, or combinations thereof, heterocyclic group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof, arylalkyl having 7 to 16 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido, and acyloxy, or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof, cycloalkylalkyl having 4 to 16 carbon atoms, which is unsubstituted or substituted one or more times by halogen, oxo, alkyl or combinations thereof, or alkoxyalkyl having 3 to 8 carbon atoms;

$R^5$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups;

$R^6$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, cycloalkylalkyl having 4 to 16 carbon atoms, which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido, and acyloxy, or combinations thereof, arylalkyl having 7 to 16 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, acylamido, and acyloxy, or combinations thereof, a heterocyclic group, which is saturated, partially saturated or fully unsaturated, having 5 to 10 ring atoms in which at least 1 ring atom is an N, O or S atom, which is unsubstituted or substituted one or more times by halogen, aryl, alkyl, alkoxy, alkoxycarbonyl, cyano, halogenated alkyl, nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

or a pharmaceutically acceptable salt thereof, wherein said compound can be in the form of a mixture of enantiomers such as the racemate, or a mixture of diastereomers, or can be in the form of a single enantiomer or a single diastereomer.

3. A compound according to claim 1, wherein said compound is selected from Formula III.

4. A compound according to claim 1, wherein said compound is selected from Formula VI.

5. A compound according to claim 1, wherein $R^3$ is phenyl, bromophenyl, nitrophenyl, fluorophenyl, trifluoromethoxyphenyl, methoxyphenyl, carboxyphenyl, dimethylphenyl, or methylpyridyl.

6. A compound according to claim 1, wherein $R^3$ is 4-carboxyphenyl, 2,3-difluorophenyl, 4-methylphenyl, 4-tert-butylphenyl, 4-methoxyphenyl, 3,4-difluorophenyl, or 4-fluorophenyl.

7. A compound according to claim 1, wherein $R^3$ is cyclohexyl or cyclopentyl.

8. A compound according to claim 1, wherein $R^3$ is ethyl, $CH(CH_3)_2$, n-propyl, n-butyl, or t-butyl.

9. A compound according to claim 1, wherein $R^3$ is thiazolyl or benzothiazolyl.

10. A compound according to claim 1, wherein $R^3$ is benzyl or phenethyl, which in each case is substituted or unsubstituted.

11. A compound according to claim 1, wherein $R^3$ is benzyl, methylbenzyl, t.-butylbenzyl, methoxybenzyl, dimethoxybenzyl, carboxybenzyl, fluorobenzyl, difluorobenzyl, trifluoromethylbenzyl, trifluoromethoxybenzyl, chlorobenzyl, nitrobenzyl, methoxycarbonylbenzyl, or phenethyl.

12. A compound according to claim 1, wherein $R^5$ is $CH_3$ or $CH_2CH_3$.

13. A compound according to claim 1, wherein $R^6$ is cyclopentyl.

14. A compound according to claim 1, wherein X is CH.

15. A compound according to claim 1, wherein X is N.

16. A compound according to claim 1, wherein L is a bond, $CH_2$, $CH_2CH_2$, $CH_2CO$, $CH_2CO_2$, or $CH_2CONH$.

17. A compound according to claim 1, wherein subscript n is 0 or 1.

18. A compound according to claim 1, wherein $R^7$ is H, and $R^8$ is H, $CH_3$, $C_2H_5$, $CF_3$, hydroxymethyl, 2-(2-hydroxy)propyl), carboxy, ethoxycarbonyl, $CH_3CO$, or phenyl.

19. A compound according to claim 1, wherein $R^3$ is aryl, heterocyclic, alkyl, or cycloalkyl.

20. A compound according to claim 1, $R^5$ is alkyl having 1 to 3 carbon atoms.

21. A compound according to claim 1, wherein $R^6$ is cycloalkyl having 4 to 7 carbon atoms.

22. A compound according to claim 1, wherein $R^3$ is aryl, heterocyclic, alkyl, or cycloalkyl, $R^5$ is $CH_2CH_3$ and $R^6$ is cyclopentyl.

23. A compound according to claim 1, wherein $R^3$ is aryl, heterocyclic, alkyl, or cycloalkyl, $R^5$ is $CH_2CH_3$, $R^6$ is cyclopentyl, Y is CH, and L is $CH_2$, $CH_2CH_2$, $CH_2CH_2CH_2$, $CH_2CO$, $CH_2CO_2$, $SO_2CH_2CONH$.

24. A compound according to claim 1, wherein $R^7$ and $R^8$ are each H.

25. A compound according to claim 1, wherein said compound is selected from:
3-[(1-Cyclopentyl-3-ethylindazol)-6-yl]-1H-pyrazole;
3[(1-Cyclopentyl-3-ethylindazol)-6-yl]-1-(2,3-difluorobenzyl)-1H-pyrazole;
3[(1-Cyclopentyl-3-ethylindazol)-6-yl]-1-(4-carboxyphenyl)-1H-pyrazole;
3[(1-Cyclopentyl-3-ethylindazol)-6-yl]-1-(4-methoxyphenyl)-1H-pyrazole;
3[(1-Cyclopentyl-3-ethylindazol)-6-yl])-1-(2-methylbenzyl)-1H-pyrazole;
3[(1-Cyclopentyl-3-ethylindazol)-6-yl])-1-(4-methylsulfonylbenzyl)-1H-pyrazole;
3[(1-Cyclopentyl-3-ethylindazol)-6-yl])-1-(2-pyridylmethyl)-1H-pyrazole;
5[(1-Cyclopentyl-3-ethylindazol)-6-yl])-1-(2-pyridylmethyl)-1H-pyrazole;
and pharmaceutically acceptable salts thereof, wherein in each case the compound can be in the form of a mixture of enantiomers such as the racemate, or a mixture of diastereomers, or can be in the form of a single enantiomer or a single diastereomer.

26. A compound according to claim 1, wherein said compound is selected from:
3-[(1-Cyclopentyl-3-ethylindazole)-6-yl]-1-(2,3-difluorophenyl)pyrazole,
3-[(1-Cyclopentyl-3-ethylindazole)-6-yl])-1-(2-methylbenzyl)pyrazole,
3-[(1-Cyclopentyl-3-ethylindazole)-6-yl])-1-(4-methylsulfonylbenzyl)pyrazole,
3-[(1-Cyclopentyl-3-ethylindazole)-6-yl])-1-(2-pyridylmethyl)pyrazole,
and pharmaceutically acceptable salts thereof, wherein in each case the compound can be in the form of a mixture of enantiomers such as the racemate or a mixture of diastereomers, or can be in the form of a single enantiomer or a single diastereomer.

27. A compound according to claim 1, wherein said compound is selected from:
3-[(1-Cyclopentyl-3-ethylindazole)-6-yl]pyrazole,
3-[(1-Cyclopentyl-3-ethylindazole)-6-yl]-1-(2,3-difluorophenyl)pyrazole,
3-[(1-Cyclopentyl-3-ethylindazole)-6-yl])-1-(4-methylsulfonylbenzyl)pyrazole,
3-[(1-Cyclopentyl-3-ethylindazole)-6-yl])-1-(2-pyridylmethyl)pyrazole,
and pharmaceutically acceptable salts thereof, wherein in each case the compound can be in the form of a mixture of enantiomers such as the racemate, or a mixture of diastereomers, or can be in the form of a single enantiomer or a single diastereomer.

28. A pharmaceutical composition comprising a compound according to claim 1 and a pharmaceutically acceptable carrier.

29. A composition of claim 28, wherein the compound is provided in a unit dosage of 0.1-50 mg.

30. A method for treating a patient suffering from memory impairment due to Alzheimer's disease, schizophrenia, Parkinson's disease, Huntington's disease, Pick's disease, Creutzfeldt-Jakob disease, depression, aging, head trauma, stroke, CNS hypoxia, cerebral senility, multiinfarct dementia, an acute neuronal disease, HIV, a cardiovascular disease, dementia, or age-related cognitive decline, comprising administering to said patient an effective amount of a compound according to claim 1.

31. A method according to claim 30, wherein said compound is administered in an amount of 0.01-100 mg/kg of body weight/day.

32. A method according to claim 30, wherein said patient is a human.

33. A method according to claim 30, wherein said patient is suffering from memory impairment due to Alzheimer's disease, schizophrenia, Parkinson's disease, Huntington's disease, Pick's disease, Creutzfeld-Jakob disease, HIV, cardiovascular disease, head trauma or age-related cognitive decline.

34. A method according to claim 30, wherein said patient is suffering from memory impairment due to dementia.

35. A method according to claim 30, wherein said patient is suffering from schizophrenia.

36. A method according to claim 30, wherein said patient is suffering from memory impairment due to Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia, an acute neuronal disease, HIV or a cardiovascular disease.

37. A method for treating a patient suffering from drug addiction or morphine dependence, comprising administering to said patient an effective amount of a compound according to claim 1.

* * * * *

UNITED STATES PATENT AND TRADEMARK OFFICE
CERTIFICATE OF CORRECTION

PATENT NO. : 7,226,930 B2
APPLICATION NO. : 10/825611
DATED : June 5, 2007
INVENTOR(S) : Allen T. Hopper It is certified that error appears in the above-identified patent and that said Letters Patent is hereby corrected as shown below:

On the Title Page, Item (73), Assignee: reads "Pharmaceutical" should read
-- Pharmaceuticals --
Column 89, line 5, reads "heterocyclic, alkyl," should read -- heterocyclic alkyl, --
Column 89, line 6, reads "claim 1, $R^5$" should read -- claim 1, wherein $R^5$ --
Column 89, line 11, reads "heterocyclic, alkyl," should read -- heterocyclic alkyl, --
Column 89, line 14, reads "heterocyclic, alkyl," should read -- heterocyclic alkyl, --
Column 89, line 16, reads "$SO_2CH_2CONH$." should read -- $SO_2$ or $CH_2CONH$. --
Column 89, line 22, reads "3[(1-Cyclopenyl..." should read -- 3-[(1-Cyclopenyl... --
Column 89, line 24, reads "3[(1-Cyclopenyl..." should read -- 3-[(1-Cyclopenyl... --
Column 89, line 26, reads "3[(1-Cyclopenyl..." should read -- 3-[(1-Cyclopenyl... --
Column 89, line 28, reads "3[(1-Cyclopenyl..." should read -- 3-[(1-Cyclopenyl... --
Column 89, line 30, reads "3[(1-Cyclopenyl..." should read -- 3-[(1-Cyclopenyl... --
Column 89, line 32, reads "3[(1-Cyclopenyl..." should read -- 3-[(1-Cyclopenyl... --
Column 89, line 34, reads "5[(1-Cyclopenyl..." should read -- 5-[(1-Cyclopenyl... --
Column 89, claim 26, after "selected from:" insert the following compound:
    -- 3-[(1-Cyclopentyl-3-ethylindazole)-6-yl]pyrazole, --

Signed and Sealed this

Twenty-ninth Day of July, 2008

JON W. DUDAS
*Director of the United States Patent and Trademark Office*

UNITED STATES PATENT AND TRADEMARK OFFICE
CERTIFICATE OF CORRECTION

PATENT NO.       : 7,226,930 B2  
APPLICATION NO.  : 10/825611  
DATED            : June 5, 2007  
INVENTOR(S)      : Allen T. Hopper It is certified that error appears in the above-identified patent and that said Letters Patent is hereby corrected as shown below:

On the Title Page, Item (73), Assignee: reads "Pharmaceutical" should read
-- Pharmaceuticals --
Column 89, line 5, reads "heterocyclic, alkyl," should read -- heterocyclic alkyl, --
Column 89, line 6, reads "claim 1, $R^5$" should read -- claim 1, wherein $R^5$ --
Column 89, line 11, reads "heterocyclic, alkyl," should read -- heterocyclic alkyl, --
Column 89, line 14, reads "heterocyclic, alkyl," should read -- heterocyclic alkyl, --
Column 89, line 16, reads "$SO_2CH_2CONH$." should read -- $SO_2$ or $CH_2CONH$. --
Column 89, line 22, reads "3[(1-Cyclopenyl..." should read -- 3-[(1-Cyclopenyl... --
Column 89, line 24, reads "3[(1-Cyclopenyl..." should read -- 3-[(1-Cyclopenyl... --
Column 89, line 26, reads "3[(1-Cyclopenyl..." should read -- 3-[(1-Cyclopenyl... --
Column 89, line 28, reads "3[(1-Cyclopenyl..." should read -- 3-[(1-Cyclopenyl... --
Column 89, line 30, reads "3[(1-Cyclopenyl..." should read -- 3-[(1-Cyclopenyl... --
Column 89, line 32, reads "3[(1-Cyclopenyl..." should read -- 3-[(1-Cyclopenyl... --
Column 89, line 34, reads "5[(1-Cyclopenyl..." should read -- 5-[(1-Cyclopenyl... --
Column 89, claim 26, line 42 after "selected from:" insert the following compound:
      -- 3-[(1-Cyclopentyl-3-ethylindazole)-6-yl]pyrazole, --

This certificate supersedes the Certificate of Correction issued July 29, 2008.

Signed and Sealed this

Twenty-sixth Day of August, 2008

JON W. DUDAS  
*Director of the United States Patent and Trademark Office*